US008816058B2

(12) United States Patent
Smith et al.

(10) Patent No.: US 8,816,058 B2
(45) Date of Patent: Aug. 26, 2014

(54) POLYNUCLEOTIDES ENCODING ANTI-CD100 ANTIBODIES OR ANTIGEN-BINDING FRAGMENTS THEREOF

(75) Inventors: Ernest S. Smith, Ontario, NY (US); Terrence Lee Fisher, Rochester, NY (US)

(73) Assignee: Vaccinex, Inc., Rochester, NY (US)

( * ) Notice: Subject to any disclaimer, the term of this patent is extended or adjusted under 35 U.S.C. 154(b) by 0 days.

(21) Appl. No.: 13/517,807

(22) Filed: Jun. 14, 2012

(65) Prior Publication Data
US 2012/0270268 A1 Oct. 25, 2012

Related U.S. Application Data

(62) Division of application No. 12/776,187, filed on May 7, 2010, now Pat. No. 8,496,938.

(60) Provisional application No. 61/325,213, filed on Apr. 16, 2010, provisional application No. 61/176,826, filed on May 8, 2009.

(51) Int. Cl.
*C07H 21/04* (2006.01)
*C12N 1/20* (2006.01)

(52) U.S. Cl.
USPC .................................. 536/23.53; 435/252.3

(58) Field of Classification Search
None
See application file for complete search history.

(56) References Cited

U.S. PATENT DOCUMENTS

| | | | |
|---|---|---|---|
| 5,070,192 A | 12/1991 | Earnshaw et al. | |
| 6,576,754 B2 | 6/2003 | Hall et al. | |
| 7,351,803 B2 | 4/2008 | Johnson et al. | |
| 7,700,102 B2 | 4/2010 | Hall et al. | |
| 7,919,246 B2 | 4/2011 | Lai et al. | |
| 7,919,594 B2 | 4/2011 | Smith et al. | |
| 8,067,247 B2 | 11/2011 | Belin et al. | |
| 2010/0285036 A1 | 11/2010 | Smith et al. | |

FOREIGN PATENT DOCUMENTS

| | | |
|---|---|---|
| WO | WO 93/14125 A1 | 7/1993 |
| WO | WO 95/07706 A1 | 3/1995 |
| WO | WO 97/17368 A1 | 5/1997 |
| WO | WO 03/010041 A1 | 4/2003 |
| WO | WO 2004/067034 A1 | 8/2004 |
| WO | WO 2006/110594 A2 | 10/2006 |

OTHER PUBLICATIONS

Basile, J. R., et al., "Semaphorin 4D provides a link between axon guidance processes and tumor-induced angiogenesis," *PNAS* 103(24):9017-9022, The National Academy of Sciences of the USA, United States (2006).

Billard, C., et al., "Switch in the protein tyrosine phosphatase associated with human CD100 semaphorin at terminal B-cell differentiation stage," *Blood* 95(3):965-972, The American Society of Hematology, United States (2000).

Bleck, G. T., "An Alternative Method for the Rapid Generation of Stable, High-Expressing Mammalian Cell Lins," *BioProcessing Journal* 5(4):36-42, International Society for BioProcess Technology, United States (2005).

Bougeret, C., et al., "Increased Surface Expression of a Newly Identified 150-kDa Dimer Early After Human T Lymphocyte Activation," *The Journal of Immunology* 148(2):318-323, The American Association of Immunologists, United States (1992).

Brand, D. D., et al., "Collagen-induced arthritis," *Nature Protocols* 2(5):1269-1275, Nature Publishing Group, England (2007).

Burgess, W. H., et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *The Journal of Cell Biology* 111:2129-2138, The Rockefeller University Press, United States (1990).

Chabbert-De Ponnat, I., et al., "Soluble CD100 functions on human monocytes and immature dendritic cells require plexin C1 and plexin B1, respectively," *International Immunology* 17(4):439-447, The Japanese Society for Immunology, Japan (2005).

Chen, C., et al., "Generation and Analysis of Random Point Mutations in an Antibody CDR2 Sequence: Many Mutated Antibodies Lose Their Ability to Bind Antigen," *J. Exp. Med.* 176:855-866, The Rockefeller University Press, United States (1992).

Claesson-Welsh, L., "Novel paths to blood vessel formation," *Blood* 105(11):4153-4154, The American Society of Hematology, United States (2005).

Conrotto, P., et al., "Sema4D induces angiogenesis through Met Recruitment by Plexin B1," *Blood* 105(11):4321-4329, The American Society of Hematology, United States (2005).

De Pascalis, R., et al., "Grafting of 'Abbreviated' Complementarity-Determining Regions Containing Specificity-Determining Residues Essential for Ligand Contact to Engineer a Less Immunogenic Humanized Monoclonal Antibody" *The Journal of Immunology* 169(6):3076-3084. The American Association of Immunologists, Inc., United States (2002).

Deaglio, S., et al., "CD38 and CD100 lead a network of surface receptors relaying positive signals for B-CLL growth and survival," *Blood* 105(8):3042-3050, The American Society of Hematology, United States (2005).

(Continued)

*Primary Examiner* — Gerald R Ewoldt
(74) *Attorney, Agent, or Firm* — Thompson Coburn LLP; Betsy Haanes

(57) ABSTRACT

Isolated polynucleotides are provided which encode antibody VH and VL polypeptides, and anti-CD100 antibodies and antigen-binding fragments thereof. In another aspect, the invention provides a vector comprising a polynucleotide of the invention. In another aspect, the invention provides a host cell comprising the vector of the invention. In another aspect, the invention provides a method of producing an antibody of the invention, e.g., for treating diseases associated with CD100, including certain autoimmune diseases, inflammatory diseases, and cancers.

24 Claims, 23 Drawing Sheets

(56) References Cited

OTHER PUBLICATIONS

Figure 1:
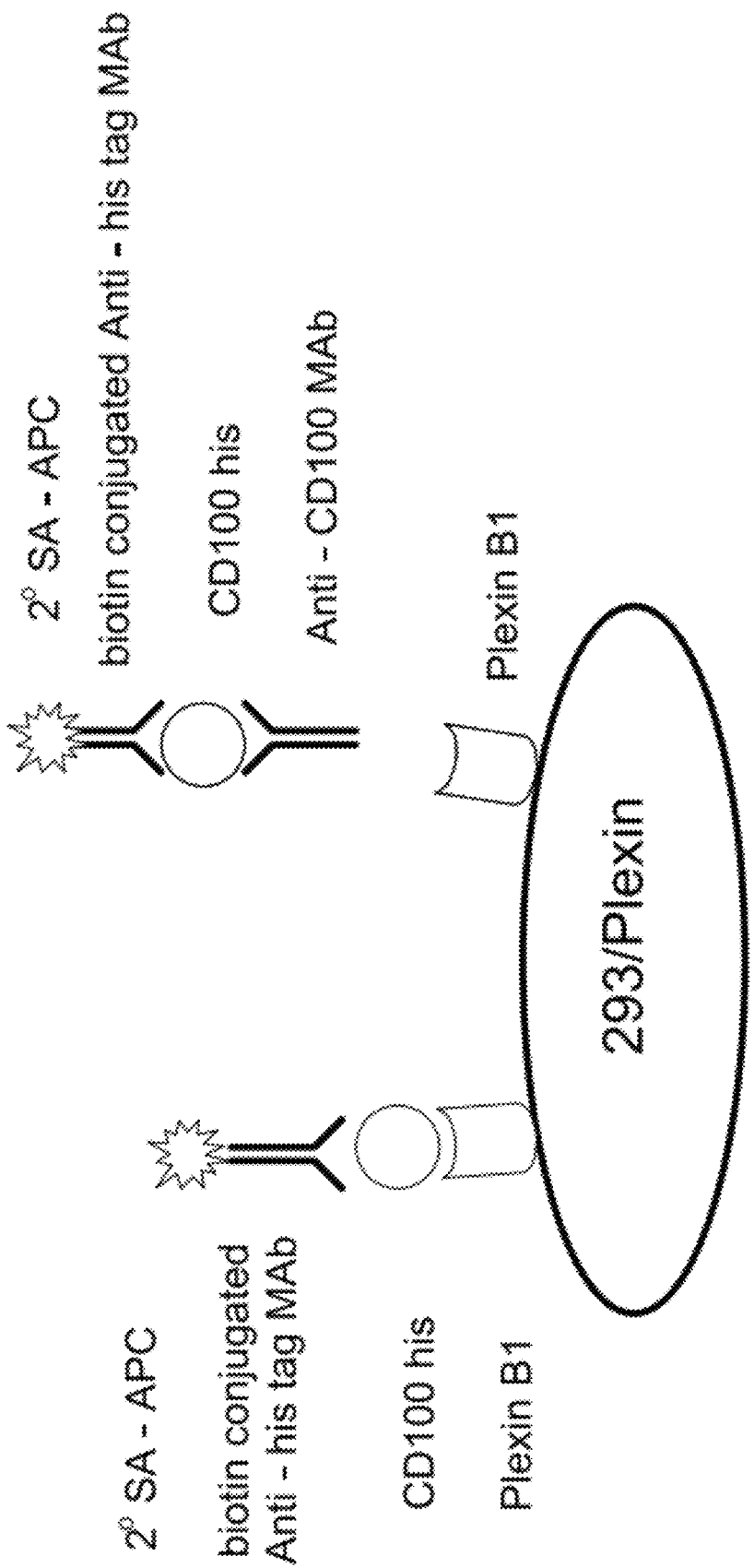

Delaire, S., et al., "Biological Activity of Soluble CD100. II. Soluble CD100, Similarly to H-SemaIII, Inhibits Immune Cell Migration," *The Journal of Immunology* 166(7):4348-4354, The American Association of Immunologists, United States (2001).

Elhabazi, A., et al., "Biological Activity of Soluble CD100. I. The Extracelluar Region of CD100 is Released from the Surface of T Lymphocytes by Regulated Proteolysis," *The Journal of Immunology* 166:4341-4347, The American Association of Immunologists, United States (2001).

Elhabazi, A., et al., "Structure and Function of the Immune Semaphorin CD100/SEMA4D" *Critical Reviews™ in Immunology*, 23(1&2):65-81, Begell House Inc., United States (2003).

Elhabazi, A., et al., "The Human Semaphorin-like Leukocyte Cell Surface Molecule CD100 Associates with a Serine Kinase Activity," *The Journal of Biological Chemistry* 272(38):23515-23520, The American Society for Biochemistry and Molecular Biology, Inc., United States (1997).

Fishwild, D. M., et al., "High-avidity human IgGκ monoclonal antibodies from a novel strain of minilocus transgenic mice," *Nature Biotechnology* 14:845-851,Nature Publishing Group, United States (1996).

Gauld, S. B., et al., "B Cell Antigen Receptor Signaling: Roles in Cell Development and Disease," *Science* 296:1641-1642, The American Association for the Advancement of Science, United States (2002).

Giordano, S., et al., "The Semaphorin 4D receptor controls invasive growth by coupling with Met," *Nature Cell Biology* 4:720-724, Nature Publishing Group, England (2002).

Giraudon, P., et al., "Semaphorin CD100 from Activated T Lymphocytes Induces Process Extension Collapse in Oligodendrocytes and Death of Immature Neural Cells," *The Journal of Immunology*, 172(2):1246-1255, The American Association of Immunologists, Inc., United States (2004).

Giraudon, P., et aL, "T-cells in Neuronal Injury and Repair: Semaphorins and Related T-cell Signals," *NeuroMolecular Medicine* 7:207-216, Humana Press Inc., United States (2005).

Goldsby, R. A., et al., "Autoimmunity," in *Kuby Immunology* 4e: pp. 502-504, W.H. Freeman and Company, United States (2000).

Gouttefangeas, C., et al., "Differential proliferative responses in subsets of human CD28+ cells delineated by BB27 mAb," *International Immunology* 6(3):423-430, The Japanese Society for Immunology, Japan (1993).

Hall, K. T., et al., "Human CD100, a novel leukocyte semaphorin that promotes B-Cell aggregation and differentiation, " *Proc. Natl. Acad. Sci* 93:11780-11785, National Academy of Sciences, United States (1996).

Herold, C., et al., "Activation signals are delivered through two distinct epitopes of CD100, a unique 150 kDa human lymphocyte surface structure previously defined by BB18 mAb," *International Immunology* 7(1):1-8, The Japanese Society for Immunology, Japan (1994).

Herold, C., et al., "CD100 defines a newly identified 150-kDa human lymphocyte surface structure," *T-cell antigens—papers* T1:50-51 (1994).

Ishida, I., et al., "Involvement of CD100, A lymphocyte semaphorin, in the activation of the human immune system via CD72: implications for the regulation of immune and inflammatory responses," *International Immunology* 15(8):1027-1034, The Japanese Society for Immunology (2003).

Kikutani, H., and Kumanogoh, A., "Semaphorins in Interactions Between T Cells and Antigen-Presenting Cells," *Nature Reviews Immunology* 3:159-167, Nature Publishing Group, England (2003).

Kornbluth, et al., "Novel Tyrosine Kinase Identified by Phosphotyrosine Antibody Screening of cDNA Libraries," *Molecular and Cellular Biology* 8(12):5541-5544, American Society for Microbiology, United States (1988).

Kruger, R. P., et al., "Semaphorins Command Cells to Move," *Nature Reviews Molecular Cell Biology* 6:789-800, Nature Publishing Group, England (2005).

Kumanogoh, A., and Kikutani, H., "Immune semaphorins: a new area of semaphorin research," *Journal of Cell Science* 116:3463-3470, The Company of Biologists Ltd, England (2003).

Kumanogoh, A., and Kikutani, H., "The CD100-CD72 interaction: a novel mechanism of immune regulation," *TRENDS in Immunology* 22(12):670-676, Elsevier Science Ltd., England (2001).

Kumanogoh, A., et al., "Class IV semaphorin Sema4A enhances T-Cell activation and interacts with Tim-2," *Nature* 419:629-633, Nature Publishing Group, England (2002).

Kumanogoh, A., et al., "Identification of CD72 as a Lymphocyte Receptor for the Class IV Semaphorin CD100: a Novel Mechanism for Regulating B Cell Signaling," *Immunity* 13:621-631, Cell Press, United States (2000).

Kumanogoh, A., et al., "Requirement for CD100-CD72 interactions in fine-tuning of B-Cell antigen receptor signaling and homeostatic maintenance of the B-cell compartment," *International Immunology* 17(10):1277-1282, The Japanese Society for Immunology, Japan (2005).

Kumanogoh, A., et al., "Requirement for the Lymphocyte Semaphorin, CD100, in the Induction of Antigen-Specific T Cells and the Maturation of Dendritic Cells," *The Journal of Immunology* 169(3):1175-1181, The American Association of Immunologists, Inc., United States (2002).

Lamminmaki, U., and Kankare, J. A., "Crystal Structure of a Recombinant Anti-estradiol Fab Fragment in Complex with 17β-Estradiol," *The Journal of Biological Chemistry* 276(39):36687-36694, The American Society for Biochemistry and Molecular Biology, Inc., United States (2001).

Lazar, E., et al., "Transforming Growth Factor α: Mutation of Aspartic Acid 47 and Leucine 48 Results in Different Biological Activites," *Molecular and Cellular Biology* 8(3):1247-1252, American Society for Microbiology, United States (1988).

Levin, M. C., et al., "Molecular Mimicry to Neurons Results in Neurological Disease," *Abstract Viewer and Itinerary Planner*: Program No. 415.3., Society for Neuroscience, United States (2002) (Abstract).

Li, D. H., et al., "CD72 Down-Modulates BCR-Induced Signal Transduction and Diminishes Survival in Primary Mature B Lymphocytes," *The Journal of Immunology* 176:5321-5328, The American Association of Immunologists, Inc., United States (2006).

Li, D. H-H., et al., "Modulation of Peripheral B Cell Tolerance by CD72 in a Murine Model," *Arthritis & Rheumatism* 58(10):3192-3904, American College of Rheumatology, United States (2008).

Moreau-Fauvarque, C. et al., "The Transmembrane Semaphorin Sema4D/CD100, an Inhibitor of Axonal Growth, is Expressed on Oligodendrocytes and Upregulated after CNS Lesion," *The Journal of Neuroscience* 23(27):9229-9239, Society for Neuroscience, United States (2003).

Okuno, T., et al., "Roles of Sema4D-Plexin-B1 Interactions in the Central Nervous System for Pathogenesis of Experimental Autoimmune Encephalomyelitis," *The Journal of Immunology* 184(3):1499-1506, The American Association of Immunologists, Inc., United States (2010).

Pasterkamp, R. J., "R-Ras fills another GAP in semaphorin signaling," *Trends in Cell Biology* 15(2):61-64, Elsevier Ltd, England (2005).

Rudikoff, S., et al., "Single amino acid substitution altering antigen-binding specificity," *Proc. Natl. Acad. Sci. USA* 79:1979-1983, National Academy of Sciences, United States (1982).

Shi, W., "The Class IV Semaphorin CD100 Plays Nonredundant Roles in the Immune System: Defective B and T Cell Activation in CD100-Deficient Mice," *Immunity* 13:633-642, Cell Press, United States (2000).

Sierra, J. R. et al., "Tumor angiogenesis and progression are enhanced by Sema4D produced by tumor-associated macrophages," *J. Exp. Med.* 205(7):1673-1685, The Rockefeller University Press, United States (2008).

Skolnick, J., and Fetrow, J. S., "From genes to protein structure and function: novel applications of computational approaches in the genomic era," *TIBTECH* 18:34-39, Elsevier Science Ltd., England (2000).

(56) References Cited

OTHER PUBLICATIONS

Suzuki, K., et al., "Semaphorins and their receptors in immune cell interactions," *Nat Immunology* 9(1):17-23, Nature Publishing Group, England (2008).

Swiercz, J. M., et al., "ErbB-2 and Met Reciprocally Regulate Cellular Signaling via Plexin-B1," *The Journal of Biological Chemistry* 283(4): 1893-1901, The American Society for Biochemistry and Molecular Biology, Inc., United States (2008).

Tamagnone, L., et al., "Plexins Are a Large Family of Receptors for Transmembrane, Secreted, and GPI-Anchored Semaphorins in Vertebrates," *Cell* 99:71-80, Cell Press, United States (1999).

Taniguchi, Y., et al., "Sema4D deficiency results in an increase in the number of oligodendrocytes in healthy and injured mouse brains," *Journal of Neuroscience Research* 87(13):2833-2841, Wiley-Liss, Inc., United States (2009).

Turner, L. J., and Hall A., "Plexin-Induced Collapse Assay in COS Cells," *Methods in Enzymology* 406:665-676, Elsevier Inc., United States (2006).

Voet, D., and Voet, J. G., *Biochemistry*, pp. 126-128 and 228-234, John Wiley & Sons, New York, United States (1990).

Wang, X., et al., "Functional soluble CD100/Sema4D released from activated lymphocytes: possible role in normal and pathologic immune responses," *Blood* 97(11):3498-3504, The American Society of Hematology, United States (2001).

Watanabe, C., et al., "Enhanced Immune Responses in Transgenic Mice Expressing a Truncated Form of the Lymphocyte Semaphorin CD100," *The Journal of Immunology* 167(8):4321-4328, The American Association of Immunologists, United States (2001).

Young R. A., and Davis, R. W., "Efficient isolation of genes by using antibody probes," *Proc. Natl. Acad. Sci. USA* 80:1194-1198, National Academy of Sciences, United States (1983).

Zhu, L., et al., "Semaphorin 4D (CD100) is Expressed on the Surface of Human Platelets and Protrolytically Shed During Platelet Activation," *Blood* 102(11):Poster Session 155-I, The American Society of Hematology, United States (2003) (Abstract).

NCBI Entrez, GenBank Report, Accession No. X85991, Adams, R. H., Entry Date Jun. 1995.

NCBI Entrez, GenBank Report, Accession No. AA394007, Wilson, R. K, Entry Date Apr. 1997.

NCBI Entrez, GenBank Report, Accession No. AA262446, Strausberg, R., Entry Date Jan. 1997.

Unverified, machine-generated English language translation of the French Patent Publication No. FR 2686087 A1 (corresponds to International Patent Application No. WO 93/14125 A1), European Patent Office, espacenet database—Worldwide (1993) (equivalent of document FP1cited on the accompanying form PTO/SB/08A).

SEQUENCE LISTING

```
<160> NUMBER OF SEQ ID NOS: 40

<210> SEQ ID NO 1
<211> LENGTH: 862
<212> TYPE: PRT
<213> ORGANISM: Homo sapiens

<400> SEQUENCE: 1

Met Arg Met Cys Thr Pro Ile Arg Gly Leu Leu Met Ala Leu Ala Val
1               5                   10                  15

Met Phe Gly Thr Ala Met Ala Phe Ala Pro Ile Pro Arg Ile Thr Trp
                20                  25                  30

Glu His Arg Glu Val His Leu Val Gln Phe His Glu Pro Asp Ile Tyr
            35                  40                  45

Asn Tyr Ser Ala Leu Leu Leu Ser Glu Asp Lys Asp Thr Leu Tyr Ile
        50                  55                  60

Gly Ala Arg Glu Ala Val Phe Ala Val Asn Ala Leu Asn Ile Ser Glu
65                  70                  75                  80

Lys Gln His Glu Val Tyr Trp Lys Val Ser Glu Asp Lys Lys Ala Lys
                85                  90                  95

Cys Ala Glu Lys Gly Lys Ser Lys Gln Thr Glu Cys Leu Asn Tyr Ile
                100                 105                 110

Arg Val Leu Gln Pro Leu Ser Ala Thr Ser Leu Tyr Val Cys Gly Thr
            115                 120                 125

Asn Ala Phe Gln Pro Ala Cys Asp His Leu Asn Leu Thr Ser Phe Lys
        130                 135                 140
```

```
Phe Leu Gly Lys Asn Glu Asp Gly Lys Gly Arg Cys Pro Phe Asp Pro
145                 150                 155                 160

Ala His Ser Tyr Thr Ser Val Met Val Asp Gly Glu Leu Tyr Ser Gly
            165                 170                 175

Thr Ser Tyr Asn Phe Leu Gly Ser Glu Pro Ile Ile Ser Arg Asn Ser
            180                 185                 190

Ser His Ser Pro Leu Arg Thr Glu Tyr Ala Ile Pro Trp Leu Asn Glu
        195                 200                 205

Pro Ser Phe Val Phe Ala Asp Val Ile Arg Lys Ser Pro Asp Ser Pro
210                 215                 220

Asp Gly Glu Asp Arg Val Tyr Phe Phe Thr Glu Val Ser Val
225                 230                 235                 240

Glu Tyr Glu Phe Val Phe Arg Val Leu Ile Pro Arg Ile Ala Arg Val
                    245                 250                 255

Cys Lys Gly Asp Gln Gly Gly Leu Arg Thr Leu Gln Lys Lys Trp Thr
                260                 265                 270

Ser Phe Leu Lys Ala Arg Leu Ile Cys Ser Arg Pro Asp Ser Gly Leu
            275                 280                 285

Val Phe Asn Val Leu Arg Asp Val Phe Val Leu Arg Ser Pro Gly Leu
        290                 295                 300

Lys Val Pro Val Phe Tyr Ala Leu Phe Thr Pro Gln Leu Asn Asn Val
305                 310                 315                 320

Gly Leu Ser Ala Val Cys Ala Tyr Asn Leu Ser Thr Ala Glu Glu Val
                    325                 330                 335

Phe Ser His Gly Lys Tyr Met Gln Ser Thr Thr Val Glu Gln Ser His
                340                 345                 350

Thr Lys Trp Val Arg Tyr Asn Gly Pro Val Pro Lys Pro Arg Pro Gly
            355                 360                 365

Ala Cys Ile Asp Ser Glu Ala Arg Ala Ala Asn Tyr Thr Ser Ser Leu
        370                 375                 380

Asn Leu Pro Asp Lys Thr Leu Gln Phe Val Lys Asp His Pro Leu Met
385                 390                 395                 400

Asp Asp Ser Val Thr Pro Ile Asp Asn Arg Pro Arg Leu Ile Lys Lys
                    405                 410                 415

Asp Val Asn Tyr Thr Gln Ile Val Val Asp Arg Thr Gln Ala Leu Asp
                420                 425                 430

Gly Thr Val Tyr Asp Val Met Phe Val Ser Thr Asp Arg Gly Ala Leu
            435                 440                 445

His Lys Ala Ile Ser Leu Glu His Ala Val His Ile Ile Glu Glu Thr
        450                 455                 460

Gln Leu Phe Gln Asp Phe Glu Pro Val Gln Thr Leu Leu Leu Ser Ser
465                 470                 475                 480

Lys Lys Gly Asn Arg Phe Val Tyr Ala Gly Ser Asn Ser Gly Val Val
                    485                 490                 495

Gln Ala Pro Leu Ala Phe Cys Gly Lys His Gly Thr Cys Glu Asp Cys
                500                 505                 510

Val Leu Ala Arg Asp Pro Tyr Cys Ala Trp Ser Pro Pro Thr Ala Thr
            515                 520                 525

Cys Val Ala Leu His Gln Thr Glu Ser Pro Ser Arg Gly Leu Ile Gln
        530                 535                 540

Glu Met Ser Gly Asp Ala Ser Val Cys Pro Asp Lys Ser Lys Gly Ser
545                 550                 555                 560
```

Tyr Arg Gln His Phe Lys His Gly Gly Thr Ala Glu Leu Lys Cys
565                         570                         575

Ser Gln Lys Ser Asn Leu Ala Arg Val Phe Trp Lys Phe Gln Asn Gly
        580                         585                         590

Val Leu Lys Ala Glu Ser Pro Lys Tyr Gly Leu Met Gly Arg Lys Asn
            595                         600                         605

Leu Leu Ile Phe Asn Leu Ser Glu Gly Asp Ser Gly Val Tyr Gln Cys
610                         615                         620

Leu Ser Glu Glu Arg Val Lys Asn Lys Thr Val Phe Gln Val Val Ala
625                         630                         635                         640

Lys His Val Leu Glu Val Lys Val Val Pro Lys Pro Val Ala Pro
                        645                         650                         655

Thr Leu Ser Val Val Gln Thr Glu Gly Ser Arg Ile Ala Thr Lys Val
                660                         665                         670

Leu Val Ala Ser Thr Gln Gly Ser Pro Pro Thr Pro Ala Val Gln
                    675                         680                         685

Ala Thr Ser Ser Gly Ala Ile Thr Leu Pro Pro Lys Pro Ala Pro Thr
                690                         695                         700

Gly Thr Ser Cys Glu Pro Lys Ile Val Ile Asn Thr Val Pro Gln Leu
705                         710                         715                         720

His Ser Glu Lys Thr Met Tyr Leu Lys Ser Ser Asp Asn Arg Leu Leu
                    725                         730                         735

Met Ser Leu Phe Leu Phe Phe Val Leu Phe Leu Cys Leu Phe Phe
                740                         745                         750

Tyr Asn Cys Tyr Lys Gly Tyr Leu Pro Arg Gln Cys Leu Lys Phe Arg
                755                         760                         765

Ser Ala Leu Leu Ile Gly Lys Lys Pro Lys Ser Asp Phe Cys Asp
                770                         775                         780

Arg Glu Gln Ser Leu Lys Glu Thr Leu Val Glu Pro Gly Ser Phe Ser
785                         790                         795                         800

Gln Gln Asn Gly Glu His Pro Lys Pro Ala Leu Asp Thr Gly Tyr Glu
                    805                         810                         815

Thr Glu Gln Asp Thr Ile Thr Ser Lys Val Pro Thr Ala Arg Glu Asp
                820                         825                         830

Ser Gln Arg Ile Asp Asp Leu Ser Ala Arg Asp Lys Pro Phe Asp Val
                835                         840                         845

Lys Cys Glu Leu Lys Phe Ala Asp Ser Asp Ala Asp Gly Asp
850                         855                         860

<210> SEQ ID NO 2
<211> LENGTH: 861
<212> TYPE: PRT
<213> ORGANISM: Murine sp.

<400> SEQUENCE: 2

Met Arg Met Cys Ala Pro Val Arg Gly Leu Phe Leu Ala Leu Val Val
1               5                   10                  15

Val Leu Arg Thr Ala Val Ala Phe Ala Pro Val Pro Arg Leu Thr Trp
                20                  25                  30

Glu His Gly Glu Val Gly Leu Val Gln Phe His Lys Pro Gly Ile Phe
            35                  40                  45

Asn Tyr Ser Ala Leu Leu Met Ser Glu Asp Lys Asp Thr Leu Tyr Val
        50                  55                  60

Gly Ala Arg Glu Ala Val Phe Ala Val Asn Ala Leu Asn Ile Ser Glu
65                  70                  75                  80

```
Lys Gln His Glu Val Tyr Trp Lys Val Ser Glu Asp Lys Lys Ser Lys
                85                  90                  95
Cys Ala Glu Lys Gly Lys Ser Lys Gln Thr Glu Cys Leu Asn Tyr Ile
            100                 105                 110
Arg Val Leu Gln Pro Leu Ser Ser Thr Ser Leu Tyr Val Cys Gly Thr
        115                 120                 125
Asn Ala Phe Gln Pro Thr Cys Asp His Leu Asn Leu Thr Ser Phe Lys
130                 135                 140
Phe Leu Gly Lys Ser Glu Asp Gly Lys Gly Arg Cys Pro Phe Asp Pro
145                 150                 155                 160
Ala His Ser Tyr Thr Ser Val Met Val Gly Gly Glu Leu Tyr Ser Gly
                165                 170                 175
Thr Ser Tyr Asn Phe Leu Gly Ser Glu Pro Ile Ile Ser Arg Asn Ser
            180                 185                 190
Ser His Ser Pro Leu Arg Thr Glu Tyr Ala Ile Pro Trp Leu Asn Glu
        195                 200                 205
Pro Ser Phe Val Phe Ala Asp Val Ile Gln Lys Ser Pro Asp Gly Pro
210                 215                 220
Glu Gly Glu Asp Asp Lys Val Tyr Phe Phe Thr Glu Val Ser Val
225                 230                 235                 240
Glu Tyr Glu Phe Val Phe Lys Leu Met Ile Pro Arg Val Ala Arg Val
                245                 250                 255
Cys Lys Gly Asp Gln Gly Gly Leu Arg Thr Leu Gln Lys Lys Trp Thr
            260                 265                 270
Ser Phe Leu Lys Ala Arg Leu Ile Cys Ser Lys Pro Asp Ser Gly Leu
        275                 280                 285
Val Phe Asn Ile Leu Gln Asp Val Phe Val Leu Arg Ala Pro Gly Leu
290                 295                 300
Lys Glu Pro Val Phe Tyr Ala Val Phe Thr Pro Gln Leu Asn Asn Val
305                 310                 315                 320
Gly Leu Ser Ala Val Cys Ala Tyr Thr Leu Ala Thr Val Glu Ala Val
                325                 330                 335
Phe Ser Arg Gly Lys Tyr Met Gln Ser Ala Thr Val Glu Gln Ser His
            340                 345                 350
Thr Lys Trp Val Arg Tyr Asn Gly Pro Val Pro Thr Pro Arg Pro Gly
        355                 360                 365
Ala Cys Ile Asp Ser Glu Ala Arg Ala Ala Asn Tyr Thr Ser Ser Leu
        370                 375                 380
Asn Leu Pro Asp Lys Thr Leu Gln Phe Val Lys Asp His Pro Leu Met
385                 390                 395                 400
Asp Asp Ser Val Thr Pro Ile Asp Asn Arg Pro Lys Leu Ile Lys Lys
                405                 410                 415
Asp Val Asn Tyr Thr Gln Ile Val Val Asp Arg Thr Gln Ala Leu Asp
            420                 425                 430
Gly Thr Phe Tyr Asp Val Met Phe Ile Ser Thr Asp Arg Gly Ala Leu
        435                 440                 445
His Lys Ala Val Ile Leu Thr Lys Glu Val His Val Ile Glu Glu Thr
450                 455                 460
Gln Leu Phe Arg Asp Ser Glu Pro Val Leu Thr Leu Leu Leu Ser Ser
465                 470                 475                 480
Lys Lys Gly Arg Lys Phe Val Tyr Ala Gly Ser Asn Ser Gly Val Val
                485                 490                 495
```

```
Gln Ala Pro Leu Ala Phe Cys Glu Lys His Gly Ser Cys Glu Asp Cys
            500                 505                 510
Val Leu Ala Arg Asp Pro Tyr Cys Ala Trp Ser Pro Ala Ile Lys Ala
        515                 520                 525
Cys Val Thr Leu His Gln Glu Ala Ser Ser Arg Gly Trp Ile Gln
        530                 535                 540
Asp Met Ser Gly Asp Thr Ser Ser Cys Leu Asp Lys Ser Lys Glu Ser
545                 550                 555                 560
Phe Asn Gln His Phe Lys His Gly Gly Thr Ala Glu Leu Lys Cys
                565                 570                 575
Phe Gln Lys Ser Asn Leu Ala Arg Val Val Trp Lys Phe Gln Asn Gly
            580                 585                 590
Glu Leu Lys Ala Ala Ser Pro Lys Tyr Gly Phe Val Gly Arg Lys His
            595                 600                 605
Leu Leu Ile Phe Asn Leu Ser Asp Gly Asp Ser Gly Val Tyr Gln Cys
        610                 615                 620
Leu Ser Glu Glu Arg Val Arg Asn Lys Thr Val Ser Gln Leu Leu Ala
625                 630                 635                 640
Lys His Val Leu Glu Val Lys Met Val Pro Arg Thr Pro Ser Pro
                645                 650                 655
Thr Ser Glu Asp Ala Gln Thr Glu Gly Ser Lys Ile Thr Ser Lys Met
            660                 665                 670
Pro Val Ala Ser Thr Gln Gly Ser Pro Thr Pro Ala Leu Trp
                675                 680                 685
Ala Thr Ser Pro Arg Ala Ala Thr Leu Pro Pro Lys Ser Ser Ser Gly
690                 695                 700
Thr Ser Cys Glu Pro Lys Met Val Ile Asn Thr Val Pro Gln Leu His
705                 710                 715                 720
Ser Glu Lys Thr Val Tyr Leu Lys Ser Ser Asp Asn Arg Leu Leu Met
                725                 730                 735
Ser Leu Leu Leu Phe Ile Phe Val Leu Phe Leu Cys Leu Phe Ser Tyr
            740                 745                 750
Asn Cys Tyr Lys Gly Tyr Leu Pro Gly Gln Cys Leu Lys Phe Arg Ser
            755                 760                 765
Ala Leu Leu Leu Gly Lys Lys Thr Pro Lys Ser Asp Phe Ser Asp Leu
            770                 775                 780
Glu Gln Ser Val Lys Glu Thr Leu Val Glu Pro Gly Ser Phe Ser Gln
785                 790                 795                 800
Gln Asn Gly Asp His Pro Lys Pro Ala Leu Asp Thr Gly Tyr Glu Thr
                805                 810                 815
Glu Gln Asp Thr Ile Thr Ser Lys Val Pro Thr Asp Arg Glu Asp Ser
            820                 825                 830
Gln Arg Ile Asp Glu Leu Ser Ala Arg Asp Lys Pro Phe Asp Val Lys
            835                 840                 845
Cys Glu Leu Lys Phe Ala Asp Ser Asp Ala Asp Gly Asp
        850                 855                 860

<210> SEQ ID NO 3
<211> LENGTH: 30
<212> TYPE: DNA
<213> ORGANISM: Artificial
<220> FEATURE:
<223> OTHER INFORMATION: Polynucleotide anti-CD100 VH CDR1

<400> SEQUENCE: 3
```

-continued ggctacagct tcagcgacta ctacatgcac                                          30

<210> SEQ ID NO 4
<211> LENGTH: 51
<212> TYPE: DNA
<213> ORGANISM: Artificial
<220> FEATURE:
<223> OTHER INFORMATION: Polynucleotide anti-CD100 VH CDR2

<400> SEQUENCE: 4
cagattaatc ctaccactgg cggcgctagc tacaaccaga agttcaaggg c                  51

<210> SEQ ID NO 5
<211> LENGTH: 27
<212> TYPE: DNA
<213> ORGANISM: Artificial
<220> FEATURE:
<223> OTHER INFORMATION: Polynucleotide anti-CD100 VH CDR3

<400> SEQUENCE: 5
tattactacg gcagacactt cgatgtc                                             27

<210> SEQ ID NO 6
<211> LENGTH: 10
<212> TYPE: PRT
<213> ORGANISM: Artificial
<220> FEATURE:
<223> OTHER INFORMATION: Polypeptide anti-CD100 VH CDR1

<400> SEQUENCE: 6

Gly Tyr Ser Phe Ser Asp Tyr Tyr Met His
1               5                   10

<210> SEQ ID NO 7
<211> LENGTH: 17
<212> TYPE: PRT
<213> ORGANISM: Artificial
<220> FEATURE:
<223> OTHER INFORMATION: Polypeptide anti-CD100 VH CDR2

<400> SEQUENCE: 7

Gln Ile Asn Pro Thr Thr Gly Gly Ala Ser Tyr Asn Gln Lys Phe Lys
1               5                   10                  15
Gly

<210> SEQ ID NO 8
<211> LENGTH: 9
<212> TYPE: PRT
<213> ORGANISM: Artificial
<220> FEATURE:
<223> OTHER INFORMATION: Polypeptide anti-CD100 VH CDR3

<400> SEQUENCE: 8

Tyr Tyr Tyr Gly Arg His Phe Asp Val
1               5

<210> SEQ ID NO 9
<211> LENGTH: 118
<212> TYPE: PRT
<213> ORGANISM: Artificial
<220> FEATURE:
<223> OTHER INFORMATION: Polypeptide anti-CD100 VH 2503

<400> SEQUENCE: 9

Gln Val Gln Leu Val Gln Ser Gly Ala Glu Val Lys Lys Pro Gly Ser
1               5                   10                  15

```
Ser Val Lys Val Ser Cys Lys Ala Ser Gly Tyr Ser Phe Ser Asp Tyr
        20                  25                  30

Tyr Met His Trp Val Arg Gln Ala Pro Gly Gln Gly Leu Glu Trp Met
            35                  40                  45

Gly Gln Ile Asn Pro Thr Thr Gly Gly Ala Ser Tyr Asn Gln Lys Phe
    50                  55                  60

Lys Gly Lys Ala Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Tyr Gly Arg His Phe Asp Val Trp Gly Gln Gly Thr
            100                 105                 110

Thr Val Thr Val Ser Ser
        115

<210> SEQ ID NO 10
<211> LENGTH: 118
<212> TYPE: PRT
<213> ORGANISM: Artificial
<220> FEATURE:
<223> OTHER INFORMATION: Polypeptide anti-CD100 VH 67

<400> SEQUENCE: 10

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Ser Asp Tyr
        20                  25                  30

Tyr Met His Trp Val Lys Gln Ser Pro Glu Asn Ser Leu Glu Trp Ile
            35                  40                  45

Gly Gln Ile Asn Pro Thr Thr Gly Gly Ala Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Lys Ser Leu Thr Ser Glu Glu Ser Ala Val Tyr Tyr Cys
                85                  90                  95

Thr Arg Tyr Tyr Tyr Gly Arg His Phe Asp Val Trp Gly Gln Gly Thr
            100                 105                 110

Thr Val Thr Val Ser Ser
        115

<210> SEQ ID NO 11
<211> LENGTH: 45
<212> TYPE: DNA
<213> ORGANISM: Artificial
<220> FEATURE:
<223> OTHER INFORMATION: Polynucleotide anti-CD100 VL CDR1

<400> SEQUENCE: 11
aaggccagcc aaagcgtgga ttatgatggc gatagctata tgaac          45

<210> SEQ ID NO 12
<211> LENGTH: 21
<212> TYPE: DNA
<213> ORGANISM: Artificial
<220> FEATURE:
<223> OTHER INFORMATION: Polynucleotide anti-CD100 VL CDR2

<400> SEQUENCE: 12
gctgcatcca atctggaaag c                                    21
```

<210> SEQ ID NO 13
<211> LENGTH: 27
<212> TYPE: DNA
<213> ORGANISM: Artificial
<220> FEATURE:
<223> OTHER INFORMATION: Polynucleotide anti-CD100 VL CDR3

<400> SEQUENCE: 13
cagcaaagca atgaggatcc ctacacc                                              27

<210> SEQ ID NO 14
<211> LENGTH: 15
<212> TYPE: PRT
<213> ORGANISM: Artificial
<220> FEATURE:
<223> OTHER INFORMATION: Polypeptide anti-CD100 VL CDR1

<400> SEQUENCE: 14

Lys Ala Ser Gln Ser Val Asp Tyr Asp Gly Asp Ser Tyr Met Asn
1               5                   10                  15

<210> SEQ ID NO 15
<211> LENGTH: 7
<212> TYPE: PRT
<213> ORGANISM: Artificial
<220> FEATURE:
<223> OTHER INFORMATION: Polypeptide anti-CD100 VL CDR2

<400> SEQUENCE: 15

Ala Ala Ser Asn Leu Glu Ser
1               5

<210> SEQ ID NO 16
<211> LENGTH: 9
<212> TYPE: PRT
<213> ORGANISM: Artificial
<220> FEATURE:
<223> OTHER INFORMATION: Polypeptide anti-CD100 VL CDR3

<400> SEQUENCE: 16

Gln Gln Ser Asn Glu Asp Pro Tyr Thr
1               5

<210> SEQ ID NO 17
<211> LENGTH: 111
<212> TYPE: PRT
<213> ORGANISM: Artificial
<220> FEATURE:
<223> OTHER INFORMATION: Polypeptide anti-CD100 VL 2503

<400> SEQUENCE: 17

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

```
Glu Asp Pro Tyr Thr Phe Gly Gln Gly Thr Lys Leu Glu Ile Lys
            100                 105                 110

<210> SEQ ID NO 18
<211> LENGTH: 111
<212> TYPE: PRT
<213> ORGANISM: Artificial
<220> FEATURE:
<223> OTHER INFORMATION: Polypeptide anti-CD100 VL 67

<400> SEQUENCE: 18

Asp Ile Val Met Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Tyr Thr Phe Gly Gly Gly Thr Lys Leu Glu Ile Lys
            100                 105                 110

<210> SEQ ID NO 19
<211> LENGTH: 354
<212> TYPE: DNA
<213> ORGANISM: Artificial
<220> FEATURE:
<223> OTHER INFORMATION: Polynucleotide anti-CD100 VH 2503

<400> SEQUENCE: 19
caggtgcagc tggtgcagag cggcgctgag gtgaagaagc ctggcagcag cgtgaaggtc      60
tcctgcaagg ctagcggcta cagcttcagc gactactaca tgcactgggt gagacaggcc     120
cctggccaag gcctggagtg gatgggccag attaatccta ccactggcgg cgctagctac     180
aaccagaagt tcaagggcaa ggccaccatt accgtggaca aaagcaccag cacagcctac     240
atggagctga gcagcctgag aagcgaggac accgccgtgt attactgtgc cagatattac     300
tacggcagac acttcgatgt ctggggccaa ggcaccacgg tcaccgtctc ttca           354

<210> SEQ ID NO 20
<211> LENGTH: 354
<212> TYPE: DNA
<213> ORGANISM: Artificial
<220> FEATURE:
<223> OTHER INFORMATION: Polynucleotide anti-CD100 VH 67

<400> SEQUENCE: 20
caggtccagc tgcagcagtc tggacctgag ctggtgaagc ctggggcttc agtgaagata      60
tcctgcaagg cttctggtta ctcattcagt gactactaca tgcactgggt gaagcaaagt     120
cctgaaaata gtcttgagtg gattggacag attaatccta ccactggggg tgctagctac     180
aaccagaagt tcaagggcaa ggccacatta actgtagata atcctccag cacagcctac      240 atgcagctca agagcctgac atctgaagag tctgcagtct attactgtac aagatattac     300
tacggtagac acttcgatgt ctggggccaa gggaccacgg tcaccgtttc ctca           354
```

<210> SEQ ID NO 21
<211> LENGTH: 333
<212> TYPE: DNA
<213> ORGANISM: Artificial
<220> FEATURE:
<223> OTHER INFORMATION: Polynucleotide anti-CD100 VL 2503

<400> SEQUENCE: 21

| gacatcgtga tgacccagag cccagacagc ctggctgtga gcctgggcga gagggccacc | 60 |
| atcaactgca aggccagcca aagcgtggat tatgatggcg atagctatat gaactggtac | 120 |
| cagcagaaac caggccagcc tcctaagctg ctgatttacg ctgcatccaa tctggaaagc | 180 |
| ggcgtgcctg acagattcag cggcagcggc agcggcacag atttcactct gaccatcagc | 240 |
| agcctgcagg ctgaagatgt ggcagtgtat tactgtcagc aaagcaatga ggatccctac | 300 |
| accttcggcc aagggaccaa gctcgagatc aaa | 333 |

<210> SEQ ID NO 22
<211> LENGTH: 333
<212> TYPE: DNA
<213> ORGANISM: Artificial
<220> FEATURE:
<223> OTHER INFORMATION: Polynucleotide anti-CD100 VL 67

<400> SEQUENCE: 22

| gacattgtga tgacccagtc tccagcttct ttggctgtgt ctctagggca gagggccacc | 60 |
| atctcctgca aggccagcca aagtgttgat tatgatggtg atagtttatat gaactggtac | 120 |
| caacagaaac caggacagcc acccaaactc ctcatctatg ctgcatccaa tctagaatct | 180 |
| gggatcccag ccaggtttag tggcagtggg tctgggacag acttcaccct caacatccat | 240 |
| cctgtggagg aggaggatgc tgcaacctat tactgtcagc aaagtaatga ggatccgtac | 300 |
| acgttcggag gggggaccaa gctcgagatc aaa | 333 |

<210> SEQ ID NO 23
<211> LENGTH: 2586
<212> TYPE: DNA
<213> ORGANISM: Homo sapiens

<400> SEQUENCE: 23

| atgaggatgt gcacccccat taggggggctg ctcatggccc ttgcagtgat gtttgggaca | 60 |
| gcgatggcat ttgcacccat accccggatc acctgggagc acagagaggt gcacctggtg | 120 |
| cagtttcatg agccagacat ctacaactac tcagccttgc tgctgagcga ggacaaggac | 180 |
| accttgtaca taggtgcccg ggaggcggtc ttcgctgtga acgcactcaa catctccgag | 240 |
| aagcagcatg aggtgtattg gaaggtctca aagacaaaa aagcaaaatg tgcagaaaag | 300 |
| gggaaatcaa aacagacaga gtgcctcaac tacatccggg tgctgcagcc actcagcgcc | 360 |
| acttcccttt acgtgtgtgg gaccaacgca ttccagccgg cctgtgacca cctgaactta | 420 |
| acatccttta gtttctgggg aaaaatgaa gatggcaaag aagatgtgcc ctttgaccca | 480 |
| gcacacagct acatccgt catggttgat ggagaacttt attcggggac gtcgtataat | 540 |
| ttttggga gtgaacccat catctcccga aattcttccc acagtcctct gaggacagaa | 600 |
| tatgcaatcc cttggctgaa cgagcctagt ttcgtgtttg ctgacgtgat ccgaaaaagc | 660 |
| ccagacagcc ccgacggcga ggatgacagg gtctacttct ccttcacgga ggtgtctgtg | 720 |
| gagtatgagt ttgtgttcag ggtgctgatc ccacggatag caagagtgtg caaggggggac | 780 |
| cagggcggcc tgaggacctt gcagaagaaa tggaccttcct tcctgaaagc ccgactcatc | 840 |

```
tgctcccggc cagacagcgg cttggtcttc aatgtgctgc gggatgtctt cgtgctcagg      900
tccccgggcc tgaaggtgcc tgtgttctat gcactcttca ccccacagct gaacaacgtg      960
gggctgtcgg cagtgtgcgc ctacaacctg tccacagccg aggaggtctt ctcccacggg     1020
aagtacatgc agagccaccac agtggagcag tcccacacca gtgggtgcg ctataatggc      1080 ccggtaccca agccgcggcc tggagcgtgc atcgacagcg aggcacgggc cgccaactac     1140
accagctcct tgaatttgcc agacaagacg ctgcagttcg ttaaagacca cccctttgatg    1200 gatgactcgg taaccccaat agacaacagg cccaggttaa tcaagaaaga tgtgaactac     1260
acccagatcg tggtggaccg gacccaggcc tggatgggaa ctgtctatga tgtcatgttt     1320
gtcagcacag accggggagc tctgcacaaa gccatcagcc tcgagcacgc tgttcacatc     1380
atcgaggaga cccagctctt ccaggacttt gagccagtcc agaccctgct gctgtcttca     1440
aagaagggca caggtttgt ctatgctggc tctaactcgg gcgtggtcca ggccccgctg      1500
gccttctgtg gaagcacgg cacctgcgag gactgtgtgc tggcgcggga ccctactgc       1560 gcctggagcc cgcccacagc gacctgcgtg gctctgcacc agaccgagag ccccagcagg     1620
ggtttgattc aggagatgag cggcgatgct tctgtgtgcc cggataaaag taaggaagt     1680 taccggcagc attttttcaa gcacggtggc acagcggaac tgaaatgctc ccaaaaatcc     1740
aacctggccc gggtcttttg gaagttccag aatggcgtgt gaaggccga gagccccaag     1800 tacggtctta tgggcagaaa aaacttgctc atcttcaact tgtcagaagg agacagtggg    1860
gtgtaccagt gcctgtcaga ggagagggtt aagaacaaaa cggtcttcca agtggtcgcc    1920
aagcacgtcc tggaagtgaa ggtggttcca aagcccgtag tggcccccac cttgtcagtt    1980
gttcagacag aaggtagtag gattgccacc aaagtgttgg tggcatccac ccaagggtct    2040
tctcccccaa ccccagccgt gcaggccacc tcctccgggg ccatcaccct tcctcccaag    2100
cctgcgccca ccggcacatc ctgcgaacca agatcgtca tcaacacggt ccccagctc      2160 cactcggaga aaaccatgta tcttaagtcc agcgacaacc gcctcctcat gtccctcttc   2220
ctcttcttct ttgttctctt cctctgcctc tttttctaca actgctataa gggatacctg   2280
cccagacagt gcttgaaatt ccgctcggcc ctactaattg ggaagaagaa gcccaagtca   2340
gatttctgtg accgtgagca gagcctgaag gagacgttag tagagccagg gagcttctcc   2400
cagcagaatg gggagcaccc caagccagcc ctggacaccg gctatgagac cgagcaagac   2460
accatcacca gcaaagtccc cacggatagg gaggactcac agaggatcga cgacctttct   2520
gccagggaca agcccttcga cgtcaagtgt gagctgaagt tcgctgactc agacgcagat   2580
ggagac                                                               2586
```

<210> SEQ ID NO 24
<211> LENGTH: 13
<212> TYPE: PRT
<213> ORGANISM: Artificial
<220> FEATURE:
<223> OTHER INFORMATION: Peptide epitope of proteolipid protein
      PLP(139-151)

<400> SEQUENCE: 24

His Ser Leu Gly Lys Trp Leu Gly His Pro Asp Lys Phe
1               5                   10

<210> SEQ ID NO 25
<211> LENGTH: 118
<212> TYPE: PRT

```
<213> ORGANISM: Artificial
<220> FEATURE:
<223> OTHER INFORMATION: Polypeptide anti-CD100 VH 76

<400> SEQUENCE: 25

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Arg Tyr
                20                  25                  30

Trp Met His Trp Val Lys Gln Arg Pro Gly Gln Gly Leu Glu Trp Ile
            35                  40                  45

Gly Tyr Ile Asn Pro Ser Thr Gly Tyr Ser Asp Tyr Asn Gln Lys Phe
        50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Pro Tyr Gly Trp Thr Met Asp Ser Trp Gly Gln Gly Thr
            100                 105                 110

Leu Val Thr Val Ser Ser
        115

<210> SEQ ID NO 26
<211> LENGTH: 10
<212> TYPE: PRT
<213> ORGANISM: Artificial
<220> FEATURE:
<223> OTHER INFORMATION: Polypeptide anti-CD100 VH 76 CDR1

<400> SEQUENCE: 26

Gly Tyr Thr Phe Thr Arg Tyr Trp Met His
1               5                   10

<210> SEQ ID NO 27
<211> LENGTH: 17
<212> TYPE: PRT
<213> ORGANISM: Artificial
<220> FEATURE:
<223> OTHER INFORMATION: Polypeptide anti-CD100 VH 76 CDR2

<400> SEQUENCE: 27

Tyr Ile Asn Pro Ser Thr Gly Tyr Ser Asp Tyr Asn Gln Lys Phe Lys
1               5                   10                  15

Asp

<210> SEQ ID NO 28
<211> LENGTH: 9
<212> TYPE: PRT
<213> ORGANISM: Artificial
<220> FEATURE:
<223> OTHER INFORMATION: Polypeptide anti-CD100 VH 76 CDR3

<400> SEQUENCE: 28

Asp Pro Tyr Gly Trp Thr Met Asp Ser
1               5

<210> SEQ ID NO 29
<211> LENGTH: 107
<212> TYPE: PRT
<213> ORGANISM: Artificial
<220> FEATURE:
<223> OTHER INFORMATION: Polypeptide anti-CD100 VL 76
```

<400> SEQUENCE: 29

Asp Ile Gln Met Thr Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
            20                  25                  30

Leu Ser Trp Tyr Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Tyr
                85                  90                  95

Thr Phe Gly Gly Gly Thr Lys Leu Glu Ile Lys
            100                 105

<210> SEQ ID NO 30
<211> LENGTH: 11
<212> TYPE: PRT
<213> ORGANISM: Artificial
<220> FEATURE:
<223> OTHER INFORMATION: Polypeptide anti-CD100 VL 76 CDR1

<400> SEQUENCE: 30

His Ala Ser Gln Asn Ile Asn Val Trp Leu Ser
1               5                   10

<210> SEQ ID NO 31
<211> LENGTH: 7
<212> TYPE: PRT
<213> ORGANISM: Artificial
<220> FEATURE:
<223> OTHER INFORMATION: Polypeptide anti-CD100 VL 76 CDR2

<400> SEQUENCE: 31

Lys Ala Ser Asn Leu His Thr
1               5

<210> SEQ ID NO 32
<211> LENGTH: 9
<212> TYPE: PRT
<213> ORGANISM: Artificial
<220> FEATURE:
<223> OTHER INFORMATION: Polypeptide anti-CD100 VL 76 CDR3

<400> SEQUENCE: 32

Gln Gln Gly Gln Ser Tyr Pro Tyr Thr
1               5

<210> SEQ ID NO 33
<211> LENGTH: 354
<212> TYPE: DNA
<213> ORGANISM: Artificial
<220> FEATURE:
<223> OTHER INFORMATION: Polynucleotide anti-CD100 VH 76

<400> SEQUENCE: 33
caggtccagc tgcagcagtc tggggctgaa ctggcaaaac ctggggcctc agtgaagatg      60
tcctgcaagg cttctggcta cacctttact aggtactgga tgcactgggt aaaacagagg     120
cctggacagg gtctggaatg gattggatac attaatccta gcactggtta ttctgattac     180
aatcagaagt tcaaggacaa ggccacattg actgcagaca atcctccag cacagcctac     240

```
atgcaactga gcagcctgac atctgaggac tctgcagtct attactgtgc aagagacccc      300
tacggctgga ctatggactc ctggggccaa gggactctgg tcaccgtctc ctca            354
```

<210> SEQ ID NO 34
<211> LENGTH: 30
<212> TYPE: DNA
<213> ORGANISM: Artificial
<220> FEATURE:
<223> OTHER INFORMATION: Polynucleotide anti-CD100 VH 76 CDR1

<400> SEQUENCE: 34

```
ggctacacct ttactaggta ctggatgcac                                        30
```

<210> SEQ ID NO 35
<211> LENGTH: 51
<212> TYPE: DNA
<213> ORGANISM: Artificial
<220> FEATURE:
<223> OTHER INFORMATION: Polynucleotide anti-CD100 VH 76 CDR2

<400> SEQUENCE: 35

```
tacattaatc ctagcactgg ttattctgat tacaatcaga agttcaagga c               51
```

<210> SEQ ID NO 36
<211> LENGTH: 27
<212> TYPE: DNA
<213> ORGANISM: Artificial
<220> FEATURE:
<223> OTHER INFORMATION: Polynucleotide anti-CD100 VH 76 CDR3

<400> SEQUENCE: 36

```
gacccctacg gctggactat ggactcc                                           27
```

<210> SEQ ID NO 37
<211> LENGTH: 321
<212> TYPE: DNA
<213> ORGANISM: Artificial
<220> FEATURE:
<223> OTHER INFORMATION: Polynucleotide anti-CD100 VL 76

<400> SEQUENCE: 37

```
gacatccaga tgacccagtc tccatccagt ctgtctgcat cccttggaga cacaattacc      60
atcacttgcc atgccagtca gaacattaat gtttggttaa gctggtacca gcagaaacca     120
ggaaatattc ctaaactatt gatctataag gcttccaact tgcacacagg cgtcccatca     180
aggtttagtg gcagtggatc tggaacaggt ttcacattaa ccatcagcag cctgcagcct     240
gaagacattg ccacttacta ctgtcaacag ggtcaaagtt atccgtacac gttcggaggg     300
gggaccaagc tcgagatcaa a                                                321
```

<210> SEQ ID NO 38
<211> LENGTH: 33
<212> TYPE: DNA
<213> ORGANISM: Artificial
<220> FEATURE:
<223> OTHER INFORMATION: Polynucleotide anti-CD100 VL 76 CDR1

<400> SEQUENCE: 38

```
catgccagtc agaacattaa tgtttggtta agc                                    33
```

<210> SEQ ID NO 39
<211> LENGTH: 21
<212> TYPE: DNA

```
<213> ORGANISM: Artificial
<220> FEATURE:
<223> OTHER INFORMATION: Polynucleotide anti-CD100 VL 76 CDR2

<400> SEQUENCE: 39
aaggcttcca acttgcacac a                                               21

<210> SEQ ID NO 40
<211> LENGTH: 27
<212> TYPE: DNA
<213> ORGANISM: Artificial
<220> FEATURE:
<223> OTHER INFORMATION: Polynucleotide anti-CD100 VL 76 CDR3

<400> SEQUENCE: 40
caacagggtc aaagttatcc gtacacg                                         27
```

POLYNUCLEOTIDES ENCODING
ANTI-CD100 ANTIBODIES OR
ANTIGEN-BINDING FRAGMENTS THEREOF

CROSS REFERENCE TO RELATED
APPLICATIONS

This application is a divisional of U.S. application Ser. No. 12/776,187 filed on May 7, 2010, which claims priority benefit to U.S. Provisional Appl. No. 61/325,213, filed on Apr. 16, 2010, and U.S. Provisional Appl. No. 61/176,826, filed on May 8, 2009, the entire contents of which are hereby incorporated by reference in their entirety.

REFERENCE TO A SEQUENCE LISTING
SUBMITTED ELECTRONICALLY

The content of the electronically submitted sequence listing in ASCII text file (Name SubstituteSEQIDListing.ascii; Size: 33,935 bytes; and Date of Creation: Jul. 17, 2013 is incorporated herein by reference in its entirety.

BACKGROUND OF THE INVENTION

CD100, also known as semaphorin 4D (SEMA4D), is a transmembrane protein (e.g., SEQ ID NO: 1 (human); SEQ ID NO: 2 (murine)) that belongs to the semaphorin gene family. CD100 is expressed on the cell surface as a homodimer, but upon cell activation CD100 can be released from the cell surface via proteolytic cleavage to generate active sCD100, a soluble form of the protein. See Suzuki et al. *Nature Rev. Immunol.* 3:159-167 (2003); Kukutani et al., *Nature Immunol.* 9:17-23 (2008).

CD100 was first identified by generating two mouse monoclonal antibodies, BD16 and BB18, against activated human T cell clones (Herold et al., *Int. Immunol.* 7:1-8 (1994)). CD100 was the first example of a semaphorin expressed in the immune system. CD100 is expressed abundantly on the surface of resting T cells, and weakly on resting B cells, monocytes, and professional antigen-presenting cells, such as dendritic cells (DCs). Cellular activation can stimulate up-regulation of surface expression of CD100 on B cells and DCs, as well as the generation of sCD100. CD100 is thought to function as both a receptor, which signals through its cytoplasmic domain, and as a ligand (Hall et al., *PNAS* 93:11780-11785 (1996)). One of the receptors identified for CD100 is Plexin-B1. Plexin-B1 is expressed in non-lymphoid tissues and is a high affinity (1 nM) receptor for CD100 (Tamagnone et al., *Cell* 99:71-80 (1999)).

CD100 is an important mediator of T cell and B cell activation. CD100 knockout (CD100−/−) mice have reduced antibody responses to T-dependent antigens and impaired T cell priming. Both of these functions are restored upon the administration of sCD100 (Shi et al., *Immunity* 13:633-642 (2000)).

In addition to the demonstrated effects of CD100 on immune cells, CD100 also appears to play a direct role in the demyelination and axonal degeneration seen in neuroinflammatory diseases. The pathogenesis of inflammatory demyelinating diseases, such as MS, includes both an inflammatory phase involving immune cells as well as phases of selective demyelination and neurodegeneration. CD100 is expressed in central nervous system (CNS) oligodendrocytes and is an inhibitor of axonal regeneration. CD100 expression is up-regulated in oligodendrocytes at the periphery of spinal cord lesions (Moreau-Fauvarque et al., *J. Neuroscience* 23:9229-9239 (2003)). Culturing chronically activated T cells expressing sCD100 with human multipotent neural precursors or primary oligodendrocytes from rat brain induces apoptosis and process extension collapse (Giraudon et al., *J. Immunol.* 172:1246-1255 (2004); Giraudon et al., *NeuroMolecular Med.* 7:207-216 (2005)). CD100 induced apoptosis of neural precursors can be inhibited by the BD16 anti-CD100 antibody.

CD100 knockout mice are resistant to the development of experimental allergic encephalomyelitis (EAE), which is a mouse model for human multiple sclerosis (MS) (Kumanogoh et al., *J. Immulol.* 169:1175-1181 (2002)).

A number of other studies have demonstrated that CD100 induces growth cone collapse in neurons, and, in further support of the functional relevance of CD100 in neuroinflammation, it has been reported that there are highly elevated levels of sCD100 in cerebrospinal fluid (CSF) of HTLV-1 associated myelopathy/tropical spastic paraparesis (HAM/TSP) patients. Thus, there is a direct deleterious effect of sCD100 on oligodendrocyte and neural precursor integrity and CD100 may play a pathogenic role in demyelination. As an important mediator of both inflammatory responses and direct demyelination, there is a need in the art for CD100 neutralizing molecules, e.g., anti-CD100 antibodies, for treatment of inflammatory and demyelinating diseases.

CD100 is also a potent pro-angiogenic molecule. Activation of Plexin-B1 through CD100 binding transactivates c-Met and promotes the invasive ability of tumor cells and promotes angiogenesis both in vitro and in vivo. Immunohistochemical analysis of CD100 in a large tumor sample collection revealed that CD overexpression is a very frequent event in head and neck, prostate, colon, breast, and lung cancers.

CD100/Plexin B1 signaling has also been shown to induce migration of endothelial cells and to promote migration of tumor cells (Conrotto et al., *Blood* 105:4321-4329 (2005); Giordano et al., *Nature Cell Biology* 4:720-724 (2002)). CD100 induced endothelial cell migration is prevented by CD100-blocking antibodies and by CD100 knockdown. Knocking down CD100 expression in head and neck squamous cell carcinoma (HNSCC) cells with CD100 short hairpin RNA (shRNA) before grafting into nude mice caused a dramatic reduction in tumor vascularity and tumor growth (Basile et al., *PNAS* 103:9017-9022 (2006)). Reports have recently pointed to a close correlation between inflammatory infiltration of the tumor stroma and a high vascular grade. CD100 is produced by inflammatory cells present in the tumor microenvironment. In an environment lacking CD100, the ability of mouse breast cancer cells to originate tumor masses and metastases was severely impaired, and the source of CD100 was tumor associated macrophages (Sierra et al., *JEM* 205:1673-1685 (2008)). Thus, there is a further need in the art for CD100 neutralizing molecules, e.g., anti-CD100 antibodies, for the treatment of CD100 cancer.

FIELD OF THE INVENTION

The invention relates to CD100 neutralizing antibodies, e.g., humanized monoclonal antibodies, methods of using the antibodies, and methods for treatment of conditions and diseases associated with CD100-expressing cells.

BRIEF SUMMARY OF THE INVENTION

Compositions and methods are provided for treating diseases associated with CD100, including certain such as certain types of autoimmune diseases, inflammatory diseases, cancers and invasive angiogenesis. In particular, anti-CD100 monoclonal antibodies have been developed to neutralize CD100. Mouse MAb 67 demonstrated the ability to block CD100 activity in vitro, and, reduce the severity of clinical signs of experimental allergic encephalomyelitis (EAE), collagen-induced arthritis (CIA), and cancer in mouse models. MAb 2503 is a humanized version of MAb 67 which has demonstrated improved affinity to human and murine CD100 and similar CD100 blocking activity as MAb 67.

In one embodiment, the invention provides an isolated binding molecule which specifically binds to the same CD100 epitope as a reference monoclonal antibody selected from the group consisting of 2503, 67, or 76.

In another embodiment, the invention provides an isolated binding molecule which specifically binds to CD100, wherein said binding molecule competitively inhibits a reference monoclonal antibody selected from the group consisting of 2503, 67, or 76 from specifically binding to CD100.

In another embodiment, the invention provides an isolated antibody or antigen-binding fragment thereof which specifically binds to CD100, wherein said antibody or fragment thereof is monoclonal antibody 2503, 67, or 76.

In certain embodiments, the isolated antibody or antigen-binding fragment thereof of the invention which specifically hinds to CD100, comprises a heavy chain variable region (VH) that has an amino acid sequence at least 90% identical to SEQ ID NO: 9, SEQ ID NO: 10, or SEQ ID NO: 25. In another aspect of the invention, the VH of said antibody or fragment thereof comprises an amino acid sequence identical, except for 20 or fewer conservative amino acid substitutions, to SEQ ID NO: 9, SEQ ID NO: 10, or SEQ ID NO: 25. In yet another aspect of the invention, the VH of said antibody or fragment thereof comprises or consists of the amino acid sequence of SEQ ID NO: 9, SEQ ID NO: 10 or SEQ ID NO: 25.

In certain embodiments, the isolated antibody or antigen-binding fragment thereof of the invention which specifically binds to CD100, comprises a light chain variable region (VL) that has an amino acid sequence at least 90% identical to SEQ ID NO: 17, SEQ ID NO: 18, or SEQ ID NO: 29. In another aspect of the invention, the VL of said antibody or fragment thereof comprises an amino acid sequence identical, except for 20 or fewer conservative amino acid substitutions, to SEQ ID NO: 17, SEQ ID NO: 18, or SEQ ID NO: 29. In yet another aspect of the invention, the VL of said antibody or fragment thereof comprises or consists of the amino acid sequence of SEQ ID NO: 17, SEQ ID NO: 18, or SEQ ID NO: 29.

In another embodiment, the invention provides an isolated antibody or antigen-binding fragment thereof which specifically binds to CD100, wherein the VH of said antibody or fragment thereof comprises at least one of the following CDRs: a Chothia-Kabat heavy chain complementarity determining region-1 (VH-CDR1) amino acid sequence identical, except for two or fewer amino acid substitutions, to SEQ ID NO: 6, a Kabat heavy chain complementarity determining region-2 (VH-CDR2) amino acid sequence identical, except for four or fewer amino acid substitutions, to SEQ ID NO: 7, or a Kabat heavy chain complementarity determining region-3 (VH-CDR3) amino acid sequence identical, except for two or fewer amino acid substitutions, to SEQ ID NO: 8.

In another embodiment, the invention provides an isolated antibody or antigen-binding fragment thereof which specifically binds to CD100, wherein the VL of said antibody or fragment thereof comprises at least one of the following CDRs: a Kabat light chain complementarity determining region-1 (VL-CDR1) amino acid sequence identical, except for four or fewer amino acid substitutions, to SEQ ID NO: 14, a Kabat light chain complementarity determining region-2 (VL-CDR2) amino acid sequence identical, except for two or fewer amino acid substitutions, to SEQ ID NO: 15, or a Kabat light chain complementarity determining region-3 (VL-CDR3) amino acid sequence identical, except for two or fewer amino acid substitutions, to SEQ ID NO: 16.

In another aspect, the VH of an antibody or fragment thereof of the invention comprises VH-CDR VH-CDR2, and VH-CDR3 amino acid sequences comprising SEQ ID NOs: 6, 7, and 8, respectively, except for four or fewer amino acid substitutions in one or more of said VH-CDRs. In a further aspect, the VH-CDR1, VH-CD2, and VH-CDR3 amino acid sequences are SEQ ID NOs: 6, 7, and 8, respectively.

In another aspect, the VL of an antibody or fragment thereof of the invention comprises VL-CDR1, VL-CDR2, and VL-CDR3 amino acid sequences comprising SEQ ID NOs: 14, 15, and 16, respectively, except for four or fewer amino acid substitutions in one or more of said VL-CDRs. In a further aspect, the VL-CDR1. VL-CDR2, and VL-CDR3 amino acid sequences are SEQ ID NOs: 14, 15, and 16, respectively.

In another embodiment, the invention provides an isolated antibody or antigen-binding fragment thereof which specifically hinds to CD100, wherein the VH of said antibody or fragment thereof comprises at least one of the following CDRs: a Kabat heavy chain complementarity determining region-1 (VH-CDR1) amino acid sequence identical, except for two or fewer amino acid substitutions, to SEQ ID NO: 26, a Kabat heavy chain complementarity determining region-2 (VH-CDR2) amino acid sequence identical, except for four or fewer amino acid substitutions, to SEQ ID NO: 27, or a Kabat heavy chain complementarity determining region-3 (VH-CDR3) amino acid sequence identical, except for two or fewer amino acid substitutions, to SEQ ID NO: 28.

In another embodiment, the invention provides an isolated antibody or antigen-binding fragment thereof which specifically binds to CD100, wherein the VL of said antibody or fragment thereof comprises at least one of the following CDRs: a Kabat light chain complementarity determining region-1 (VL-CDR1) amino acid sequence identical, except for four or fewer amino acid substitutions, to SEQ ID NO: 30, a Kabat light chain complementarity determining region-2 (VL-CDR2) amino acid sequence identical, except for two or fewer amino acid substitutions, to SEQ ID NO: 31, or a Kabat light chain complementarity determining region-3 (VL-CDR3) amino acid sequence identical, except for two or fewer amino acid substitutions, to SEQ ID NO: 32.

In another aspect, the VH of an antibody or fragment thereof of the invention comprises VH-CDR1, VH-CDR2, and VH-CDR3 amino acid sequences comprising SEQ NOs: 26, 27, and 28, respectively, except for four or fewer amino acid substitutions in one or more of said VH-CDRs. In a further aspect, the VH-CDR1, VH-CDR2 and VH-CDR3 amino acid sequences are SEQ ID NOs: 26, 27, and 28, respectively.

In another aspect, the VL, of an antibody or fragment thereof of the invention comprises VL-CDR1, VL-CDR2, and VL-CDR3 amino acid sequences comprising SEQ ID NOs: 30, 31, and 32, respectively, except for four or fewer amino acid substitutions in one or more of said VL-CDRs, in a further aspect, the VL-CDR1, VL-CDR2, and VL-CDR3 amino acid sequences are SEQ NOs: 30, 31, and 32, respectively.

In another aspect, an antibody or fragment thereof of the invention binds to human and murine CD100. In another aspect, the antibody or fragment thereof of the invention specifically binds to an CD100 polypeptide or fragment thereof, or a CD100 variant polypeptide with an affinity characterized by a dissociation constant ($K_D$) no greater than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $5.7\times10^{-12}$ M, $8.4\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M. In certain aspects, the CD100 polypeptide or fragment thereof, or a CD100 variant polypeptide is human or murine. In further aspects, a CD100 polypeptide or fragment thereof, or a CD100 variant polypeptide is human and said $K_D$ is about $5\times10^{-9}$ M to about $6\times10^{-9}$ M. In yet another aspect, a CD100 polypeptide or fragment thereof, or a CD100 variant polypeptide is murine and said $K_D$ is about $1\times10^{-9}$ M to about $2\times10^{-9}$ M.

In another aspect, the antibody or fragment thereof of the invention is humanized, primatized or chimeric.

In another embodiment, the invention provides a composition comprising an antibody or fragment thereof of the invention, and a carrier.

In another embodiment, the invention provides an isolated polynucleotide comprising a nucleic acid which encodes an antibody VH or VL polypeptide of the invention. In another aspect, the polynucleotide of the invention comprises or consists of a nucleic acid which encodes an antibody or fragment thereof of the invention, in yet another aspect, the invention provides a vector comprising a polynucleotide of the invention. In another aspect, the invention provides a host cell comprising the vector of the invention. In another aspect, the invention provides a method of producing an antibody of the invention.

In another embodiment, the invention provides a method for treating an autoimmune disease or an inflammatory disease in an animal in need of treatment, comprising administering to said animal a composition comprising: the isolated antibody or fragment thereof of the invention and a pharmaceutically acceptable carrier. In further embodiments, the autoimmune disease or inflammatory disease is multiple sclerosis or arthritis.

In another embodiment, the invention provides a method for treating a cancer in an animal in need of treatment, comprising administering to said animal a composition comprising: the isolated antibody or fragment thereof of the invention and a pharmaceutically acceptable carrier.

In another embodiment, the invention provides a method for inhibiting angiogenesis in an animal in need of treatment for cancer, comprising administering to said animal a composition comprising: the isolated antibody or fragment thereof of the invention and a pharmaceutically acceptable carrier.

In a further aspect, the antibody or fragment thereof of the invention inhibits CD100 binding to a CD100 receptor. In yet another aspect of the invention, the CD100 receptor is Plexin-B1.

BRIEF DESCRIPTION OF THE DRAWINGS/FIGURES

FIG. 1. Diagram of CD100 blocking assay. CD100-His shown binding to Plexin B1 on the cell surface of a stable cell line expressing Plexin B1 (293/Plexin). The CD100-His which is bound to Plexin B1 is detected using a biotin conjugated anti-His tag specific monoclonal antibody and streptavidin-APC. Anti-CD100 MAbs which are able to block binding of CD100-His to Plexin B1 result in lower fluorescence associated with the 293/Plexin cells as measured by flow cytometry.

Figure 2:
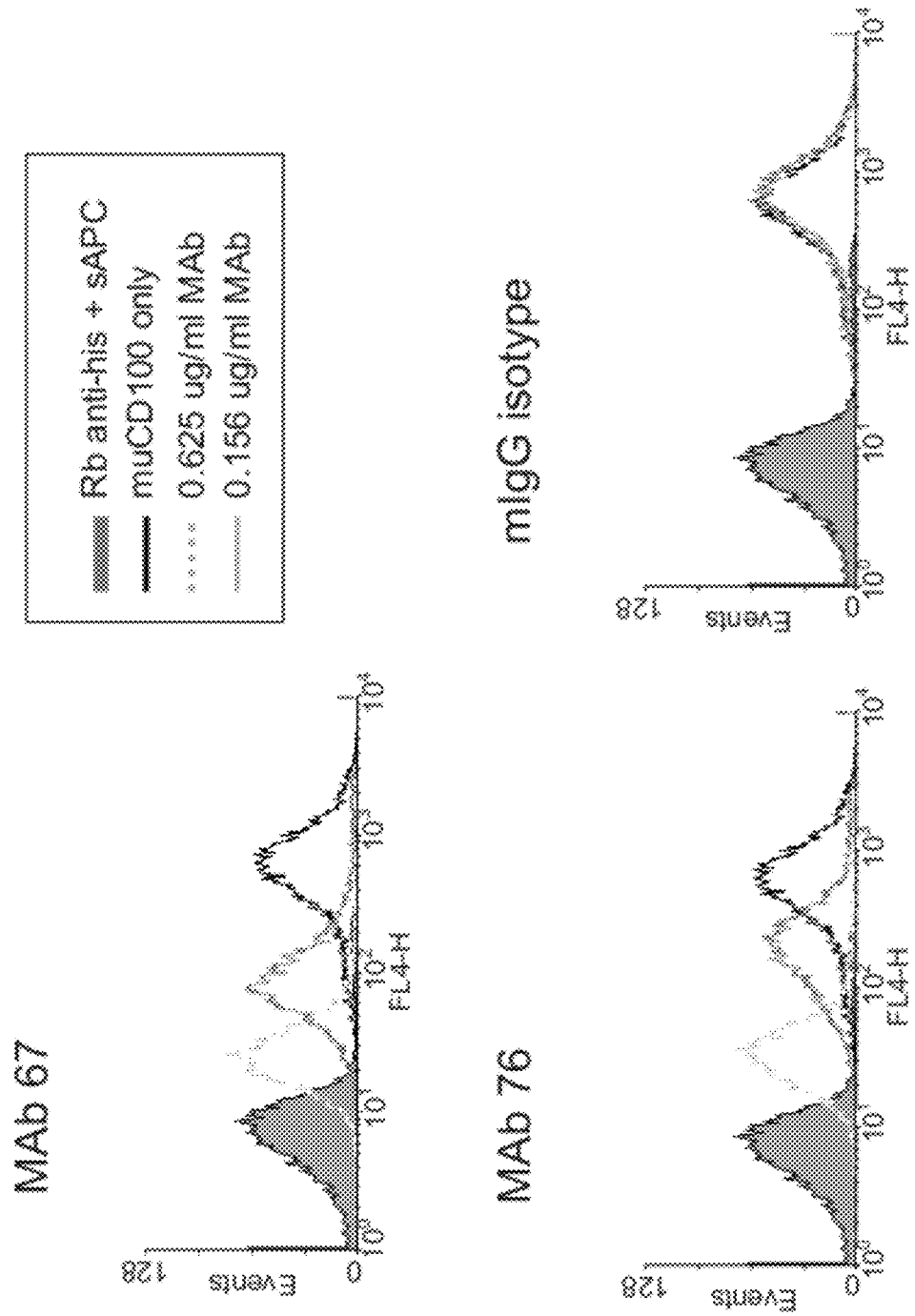

FIG. 2. Flow cytometry results for rabbit anti-His+streptavidin-APC (Rb anti-his+sAPC), mouse CD100 (muCD100 only), mouse CD100+0.625 µg/ml. MAb (MAb 67. MAb 76, and mIgG isotype), and mouse CD100+0.156 µg/ml MAb (MAb 67, MAb 76, and mIgG isotype) tested in the CD100 blocking assay described in FIG. 1 are shown. Monoclonal antibodies 67 and 76 block mouse CD100 binding to Plexin B1 receptor.

Figure 3:
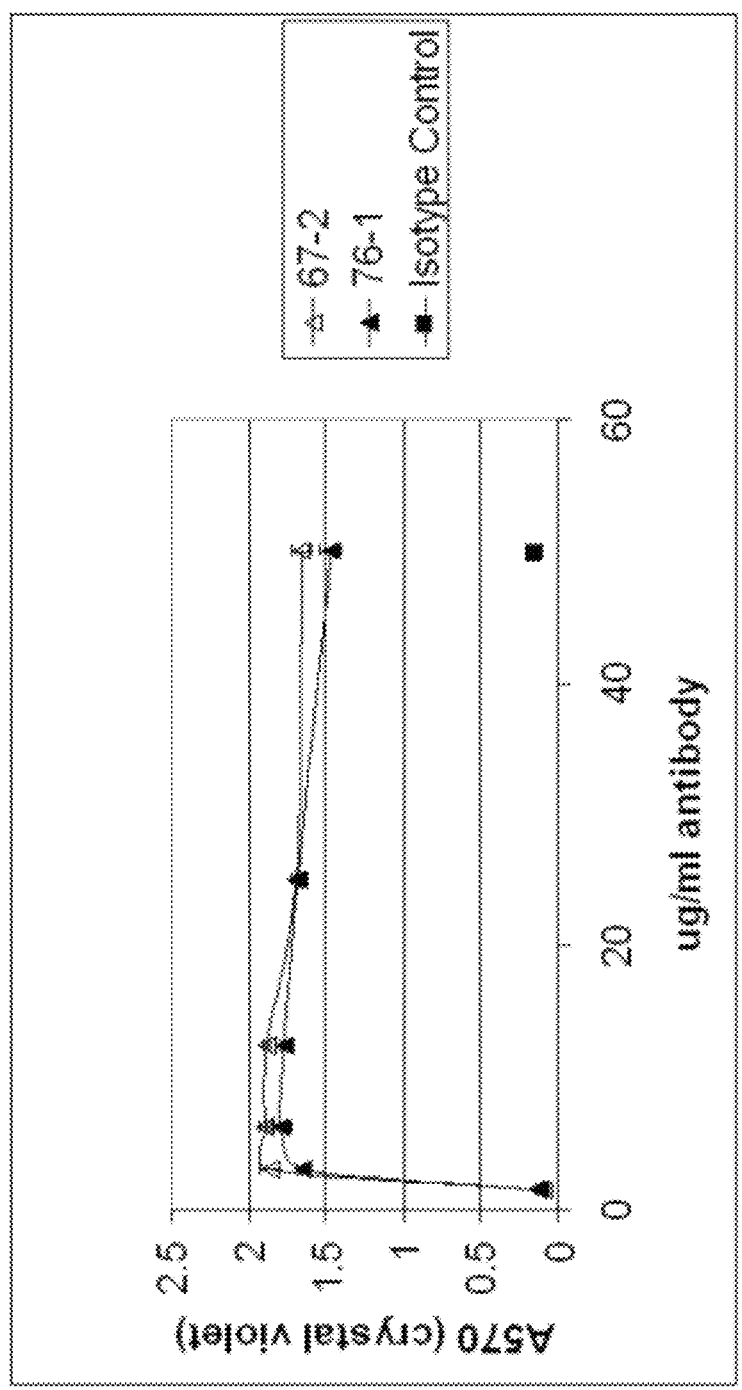

FIG. 3. Monoclonal antibodies 67 and 76 block mouse CD100 mediated detachment of 293/Plexin B cells from a fibronectin coated plate, as shown by an increase in absorbance for both MAbs 67 (67-2) and 76 (76-1) compared to isotype control.

FIG. 4. Treatment with 30 mg/kg anti-CD100 MAb 76 (1x/week or 2x/week) or MAb 67 (1x/week or 2x/week) attenuates relapsing remitting EAE in SJL mice compared to treatment with mouse IgG control as shown by reduction in clinical score (4A). The results are further illustrated by comparing percent reduction in Group Mean Score (GMS) for each MAb treatment between day 21 and study end (4B).

Figure 5A:
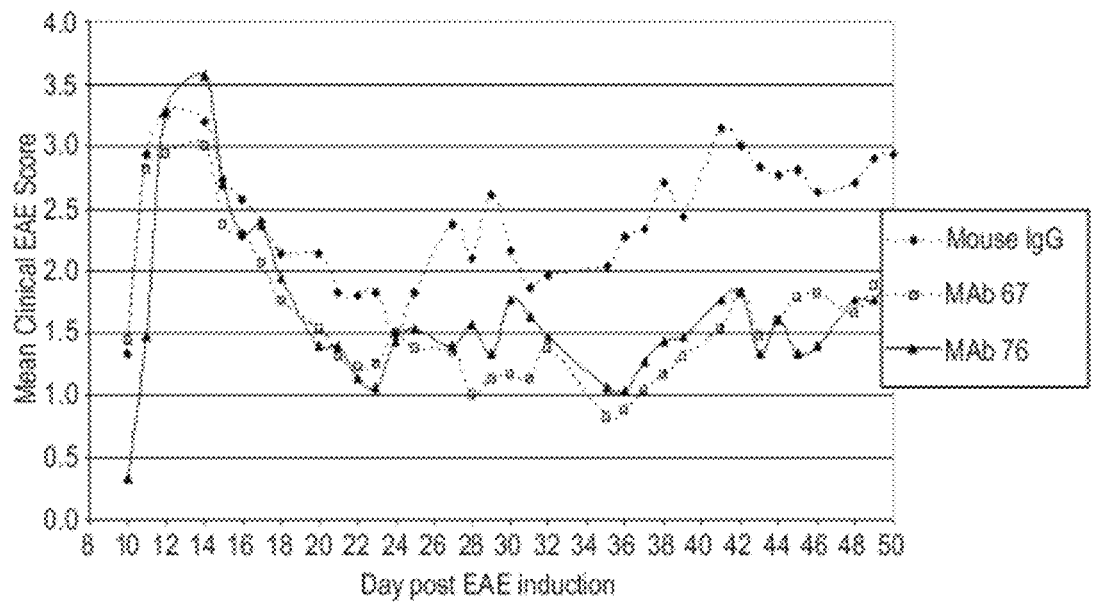
Figure 5B:
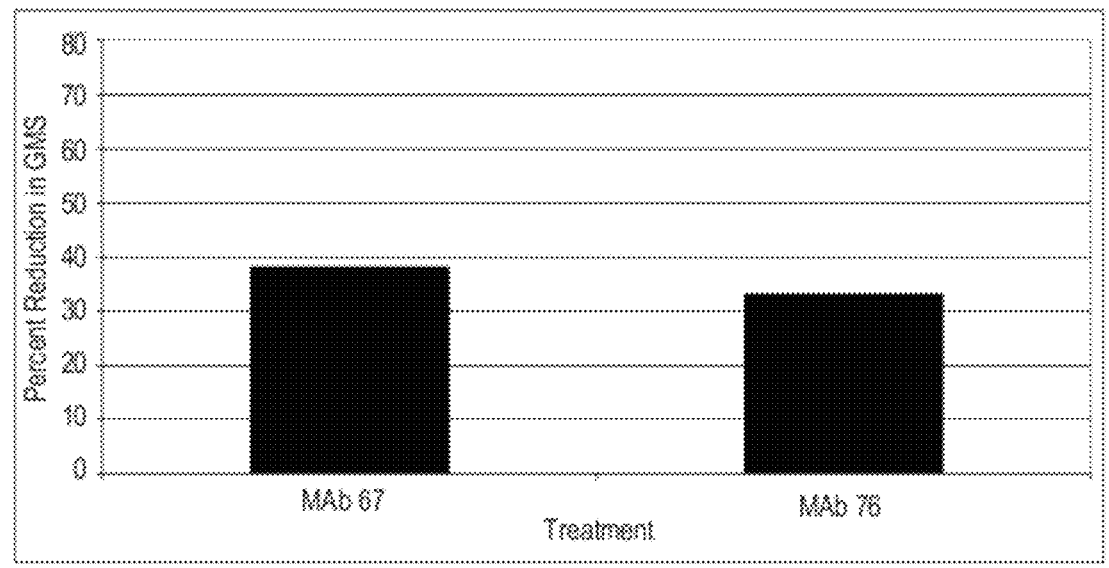

FIG. 5. Treatment with 30 mg/kg anti-CD100 MAb 76 (1x/week) or MAb 67 (1x/week) attenuates relapsing remitting EAE in SJL mice compared to treatment with mouse IgG control as shown by reduction in clinical score (5A). The results are further illustrated by comparing percent reduction in Group Mean Score (GMS) for both MAb treatments between day 18 and study end (5B).

Figure 6:
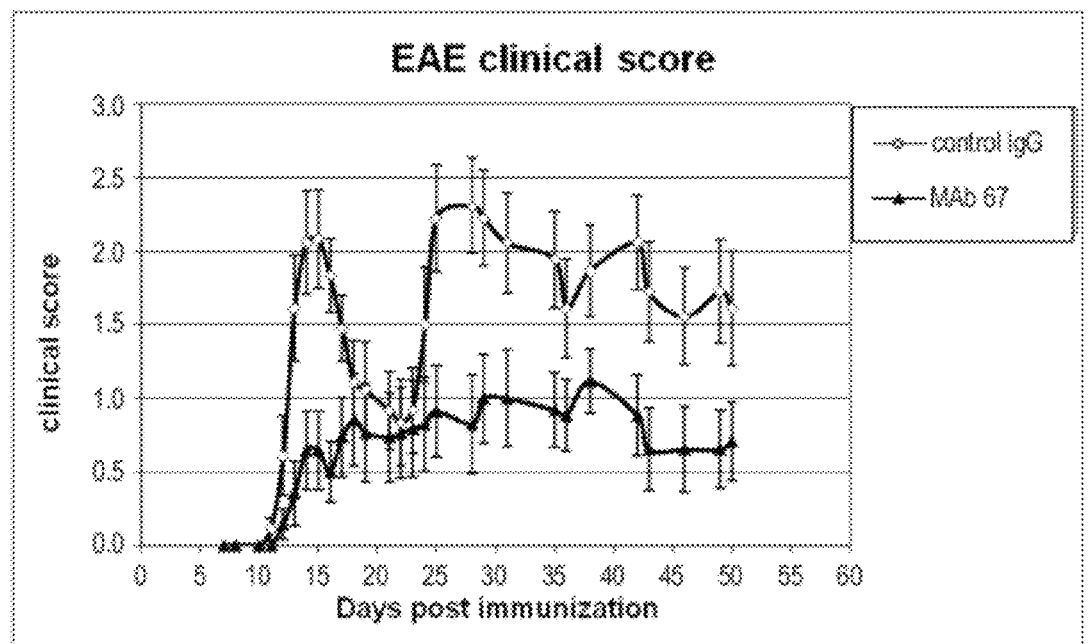

FIG. 6. Treatment with 30 mg/kg anti-CD100 MAb 67 starting at day 7 post-immunization (1x/week) attenuates relapsing remitting EAE in SJL mice compared to treatment with mouse IgG control as shown by reduction in clinical score.

Figure 7A:
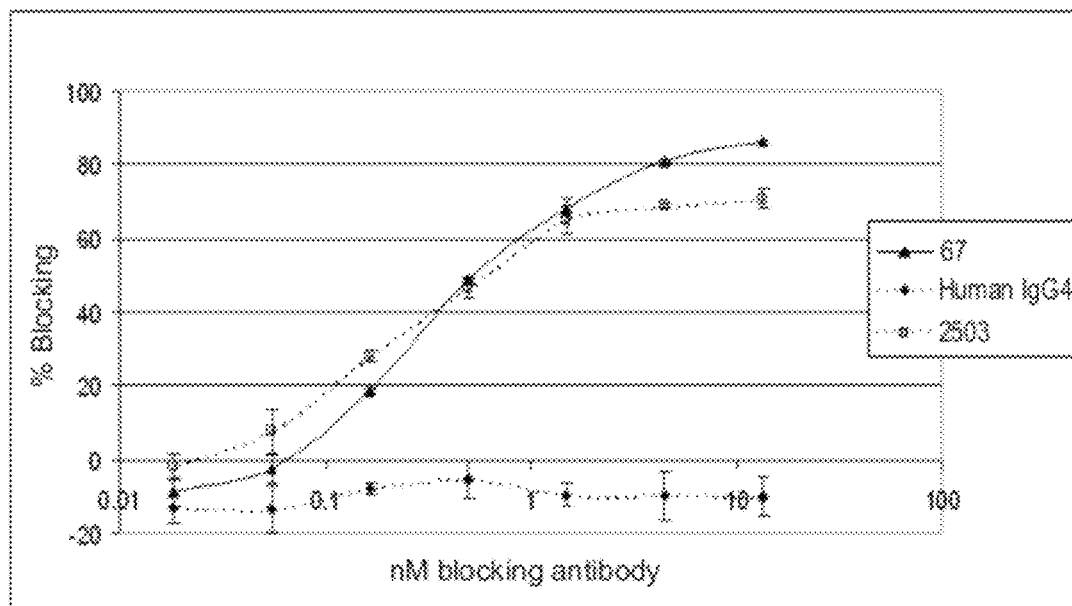
Figure 7B:
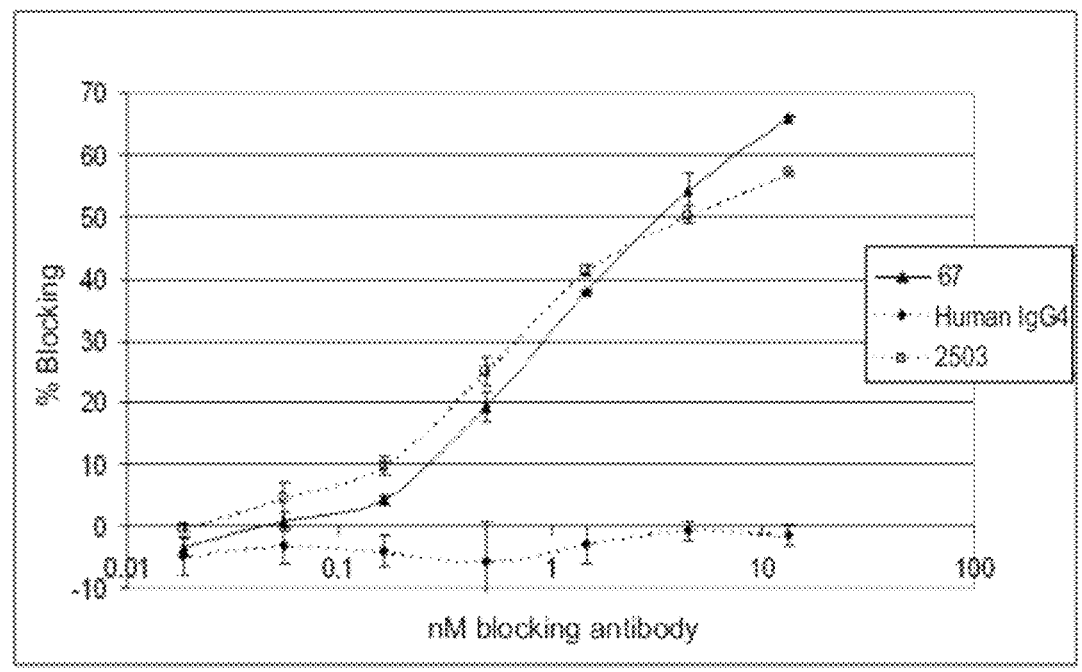

FIG. 7. ELISA results showing percent (%) blocking of biotinylated 67 binding to human CD100 (7A) or mouse CD100 (7B) due to competitive binding of MAb 2503, MAb 67, or IgG control.

Figure 8A:
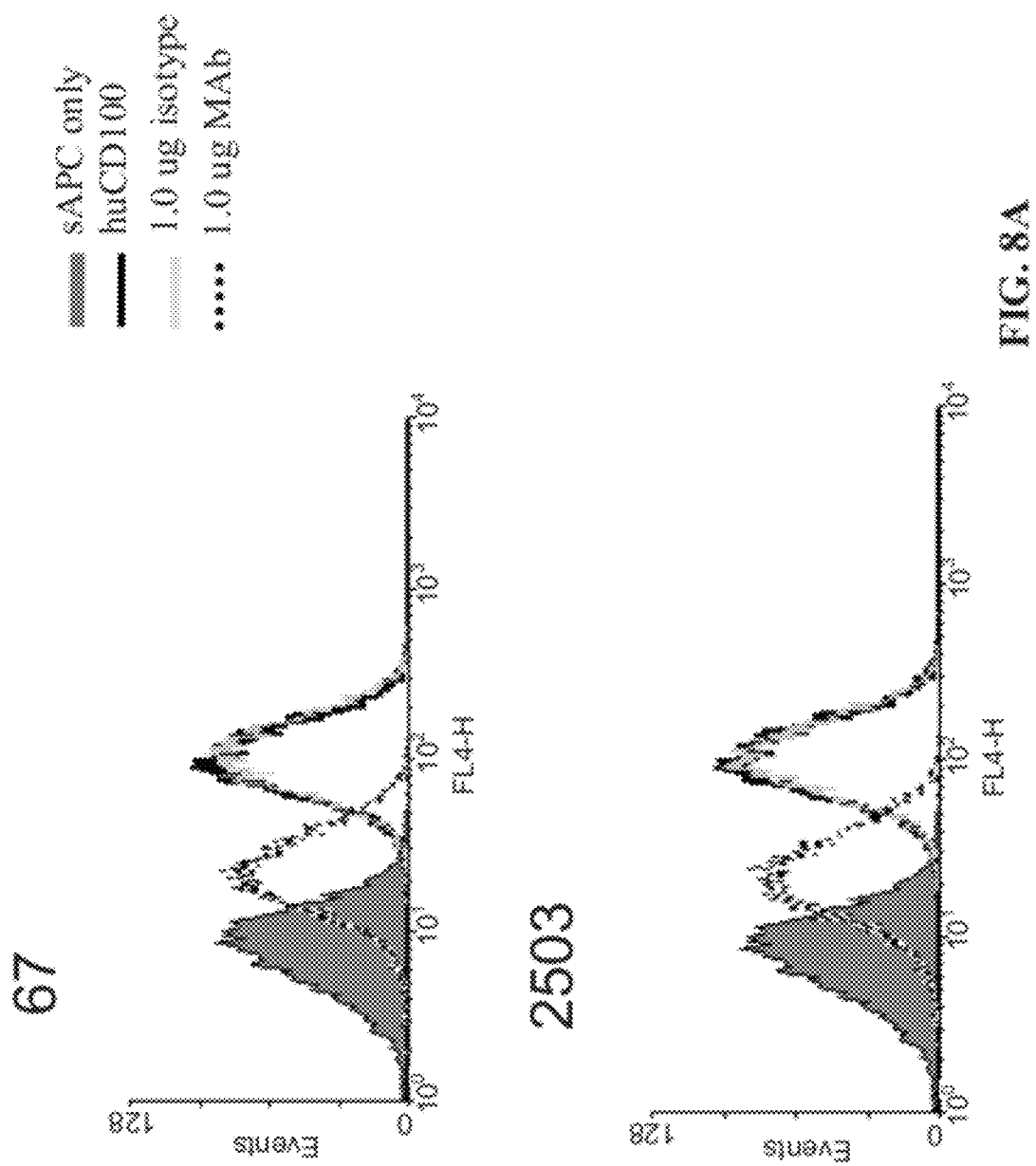
Figure 8B:
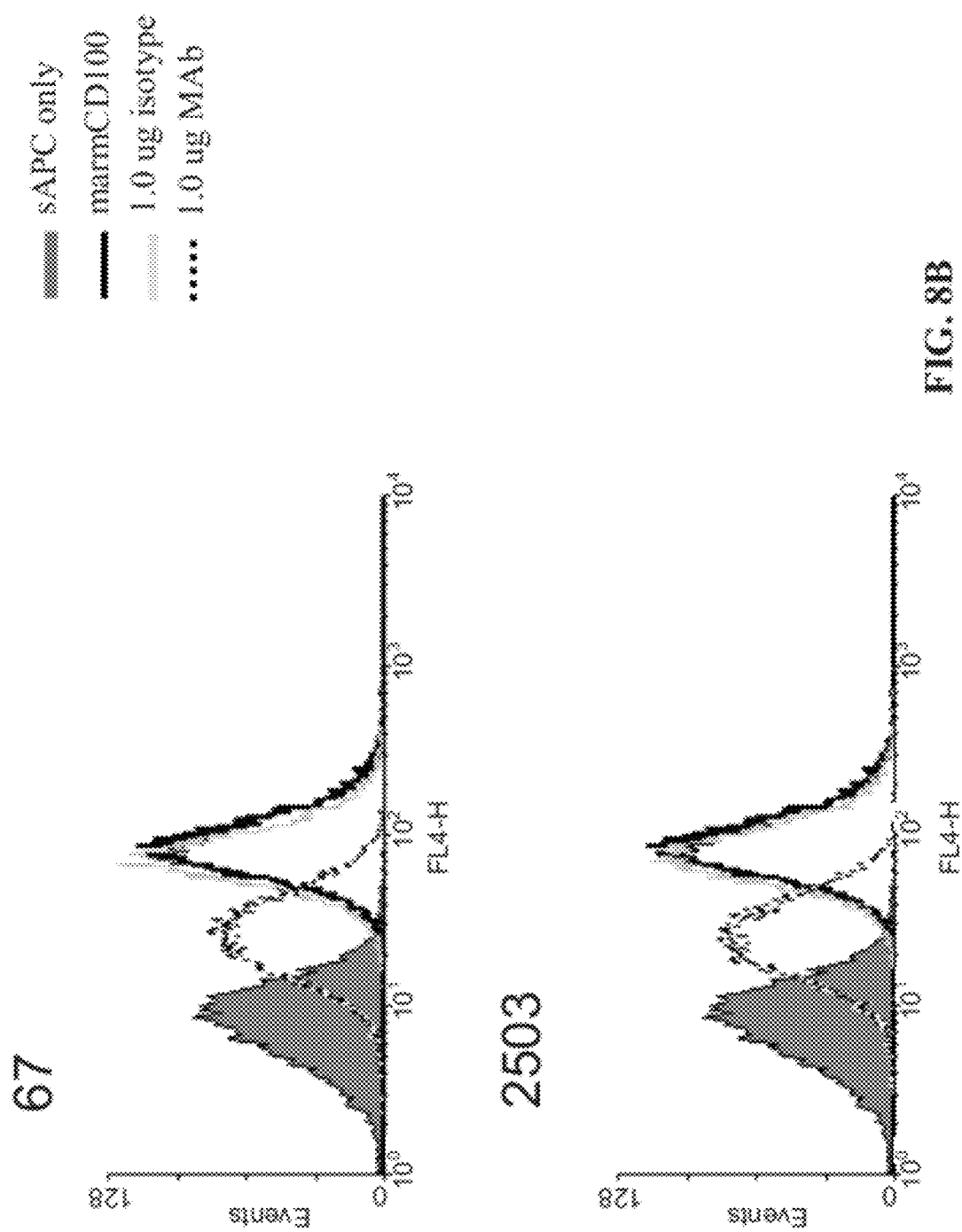
Figure 8C:
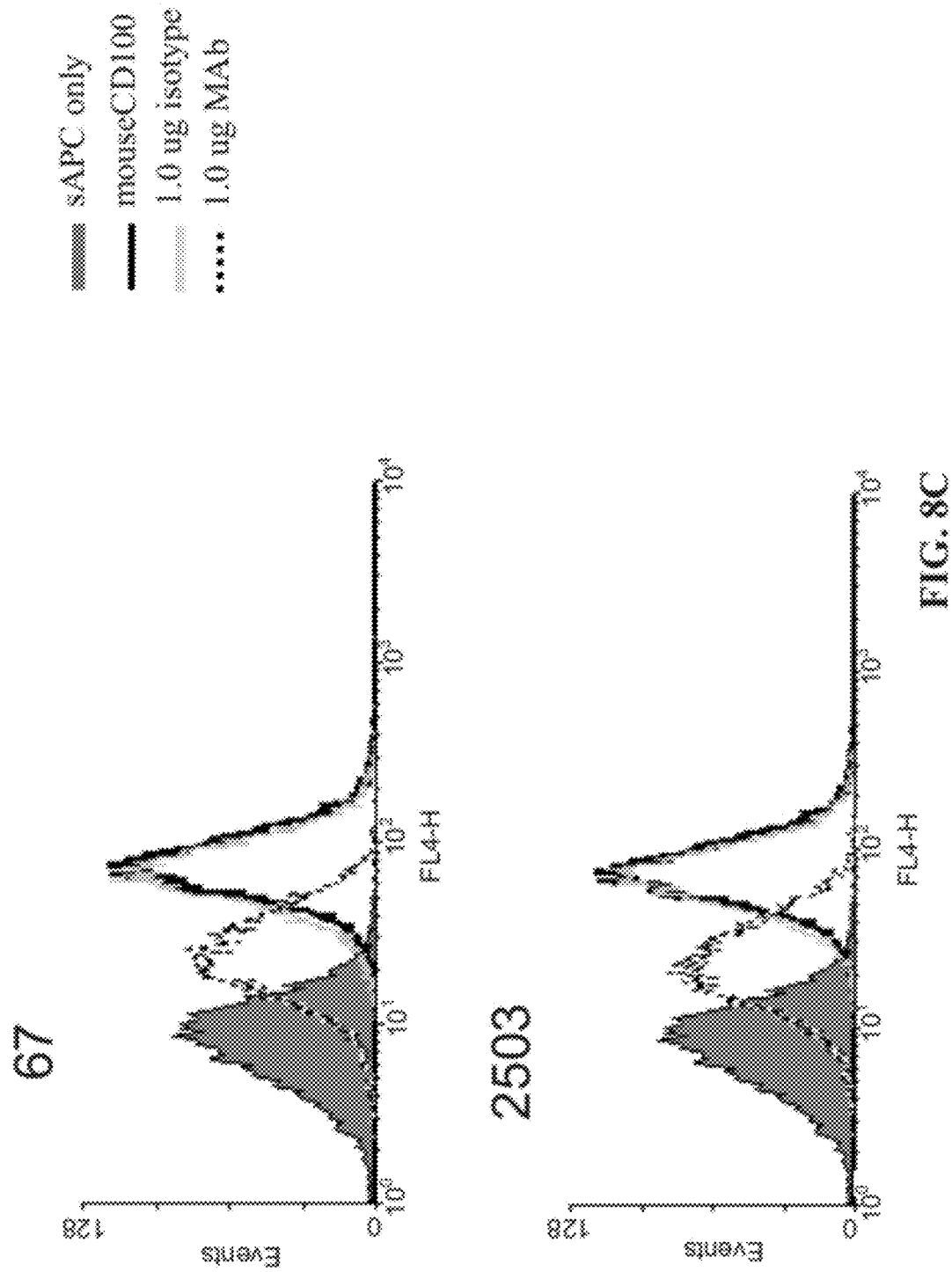

FIG. 8. Flow cytometry results for streptavidin-APC (sAPC only), human CD100 (huCD100), marmoset CD100 (marmCD100), mouse CD100 (muCD100), 1.0 µg isotype, and 1.0 µg MAb (67 or 2503) tested in the CD100 blocking assay described in FIG. 1 are shown. MAb 67 and MAb 2503 block human CD100 (8A), marmoset (8B), or mouse (8C) CD100 from binding to Plexin B1 receptor.

FIG. 9. A blocked reduction in absorbance caused by CD100 due to neutralization of CD100 by MAb 67, MAb 2503, and IgG control is shown. Anti-CD100 MAb 67 and MAb 2503 block human CD100 (9A) and marmoset CD100 (9B) mediated detachment of 293/Plexin cells from a fibronectin coated plate.

Figure 10:
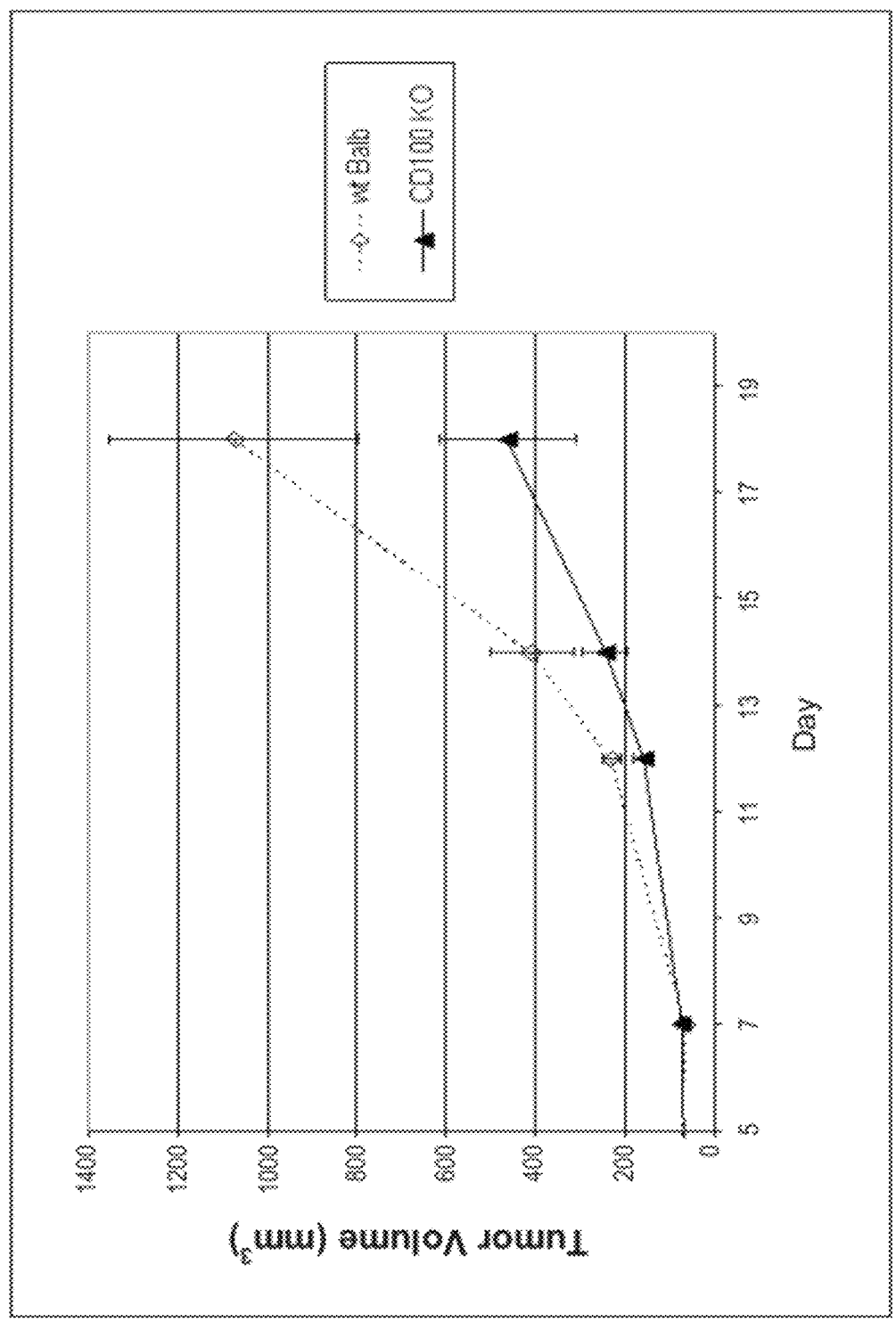

FIG. 10. Change in tumor volume (mm³) is shown for wild-type Balb/c mice and CD100−/− mice after 50,000 CT26 colon tumor cells were injected into the leg muscle of the mice.

Figure 11:
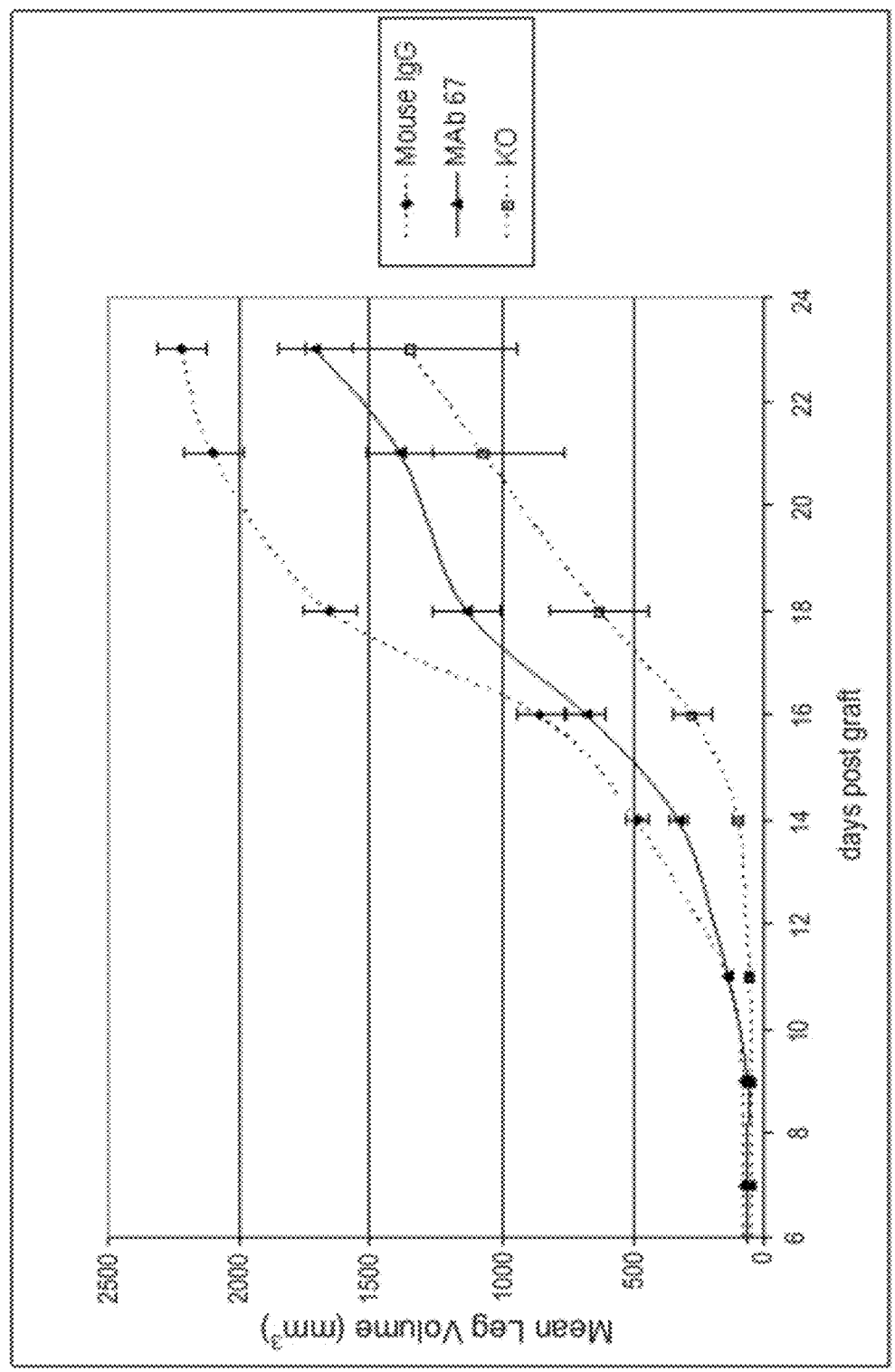

FIG. 11. Change in mean leg volume (mm³) is shown for wild-type Balb/c mice treated with 1 mg MAb 67 or 1 mg control mouse IgG and CD100−/− mice ("KO") after 50,000 CT26 tumor cells were injected into the leg muscle of the mice.

Figure 12:
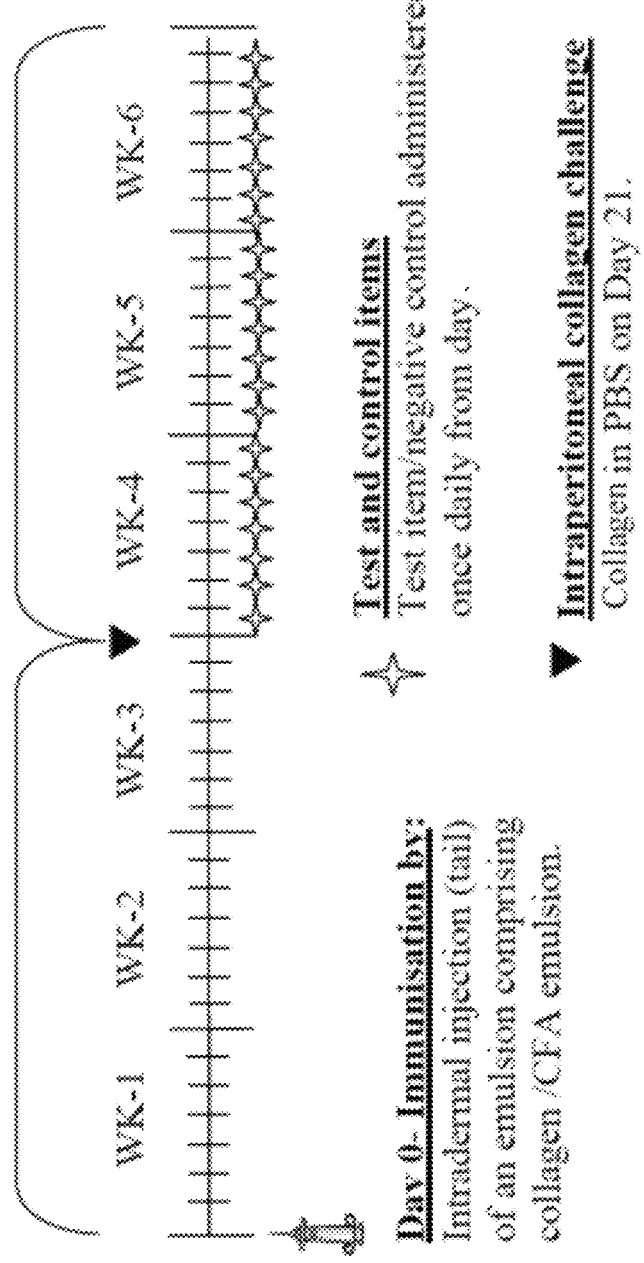

FIG. 12. A schematic showing a general treatment strategy for Collagen Induced Arthritis (CIA)

FIG. 13. Reduction in arthritis disease development n CIA model was shown for groups treated with 600 µg MAb 67. Arthritic Index (AI) in mice treated with 600 µg MAb 67 was compared to AI in mice treated with 600 µg negative control (IgG1) and 600 µg positive control etanercept (Enbrel®) when treatment was started at day 20 (13A). Arthritic Index (AI) results for treatment with MAb 67 were compared to treatment with a negative control (IgG1) and positive control etanercept (Embrel®) when treatment was started either at day 20 or when the AI was ≥3 (13B).

Figure 14A:
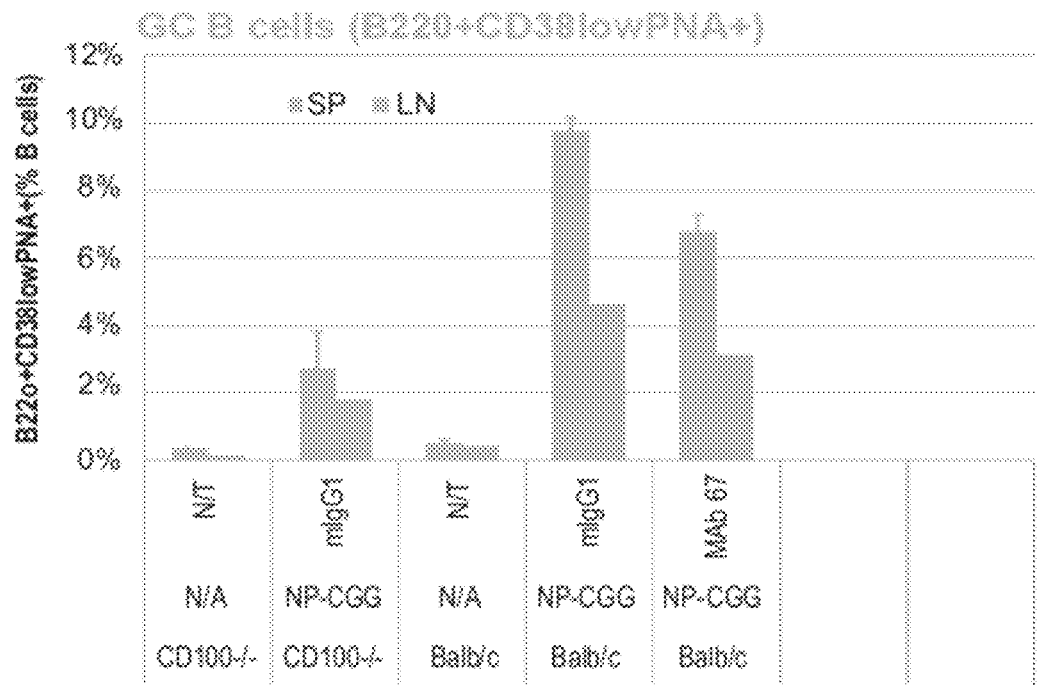
Figure 14B:
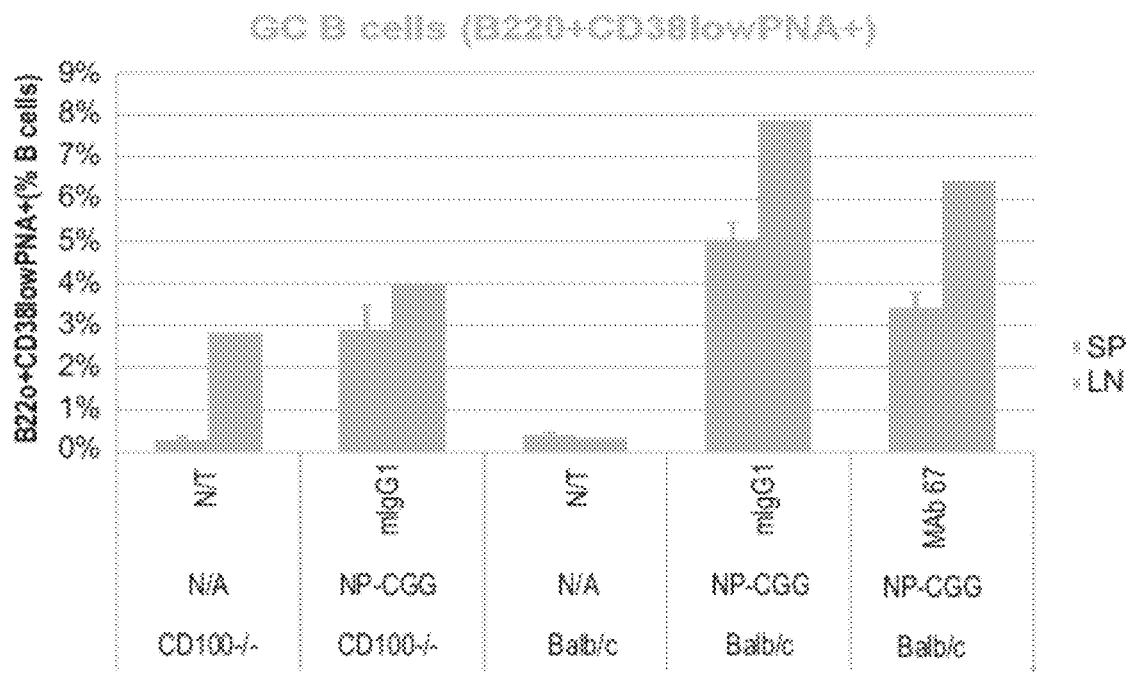

FIG. 14. In Balb/c mice immunized with (4-hydroxy-3-nitrophenyl) acetyl conjugated chicken gamma globulin precipitated with alum (aluminum-/magnesium-hydroxide) ("NP-CGG"), treatment with 600 μg MAb 67 decreased the number of germinal center (GC) B cells ("B220+ CD38lowPNA+") in spleen (SP) and lymph nodes (LN) after both primary immunization (14A) and secondary immunization (14B). Results are also shown for CD100–/– mice and Balb/c mice with and without NP-CGG immunization.

Figure 15:
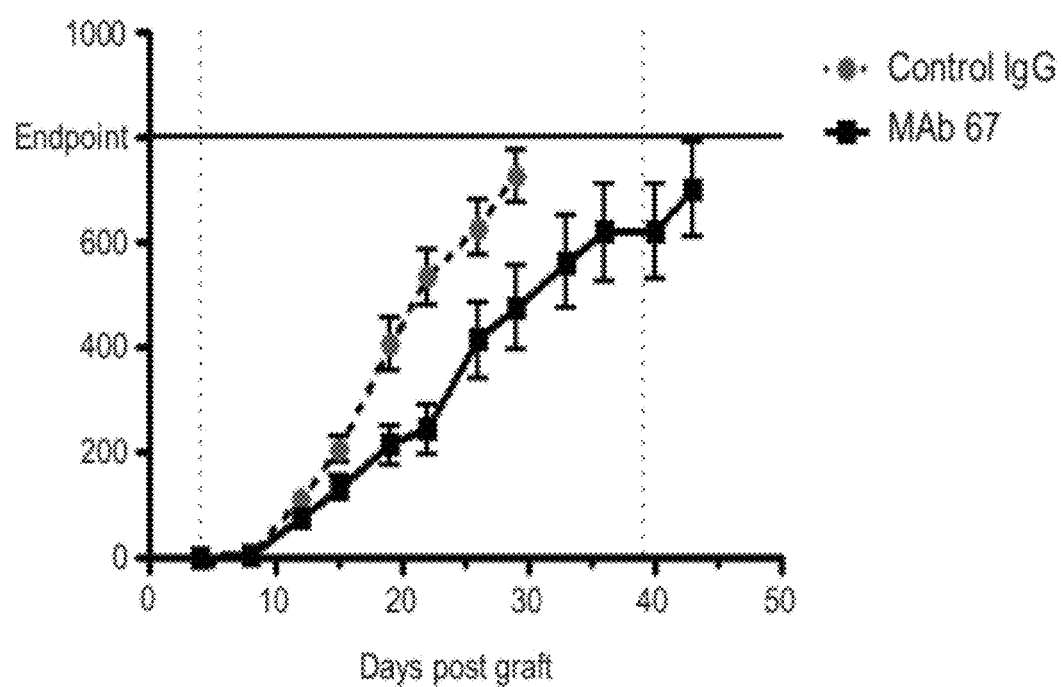

FIG. 15. Change in tumor volume ($mm^3$) is shown for wild-type Balb/c mice mice after 50,000 CT26 colon tumor cells were injected into the leg muscle of the mice. Results are shown for mice injected with 1 mg MAb 67 weekly starting on day compared to mice injected with IgG control. The study was carried out to an end point of tumor growth delay.

FIG. 16. Change in tumor volume ($mm^3$) is shown for wild-type Balb/c mice and CD100–/– mice ("SEMA4D–/–") after 50.000 BCA34 fibroblastic tumor cells were s.c. injected into the abdominal region of the mice (16A). Change in mean thigh volume ($mm^3$) is shown for wild-type Balb/c mice treated with lung MAb 67 or 1 mg control mouse IgG after 50,000 BCA34 fibroblastic tumor cells were injected into the leg muscle of the mice (16B).

Figure 17:
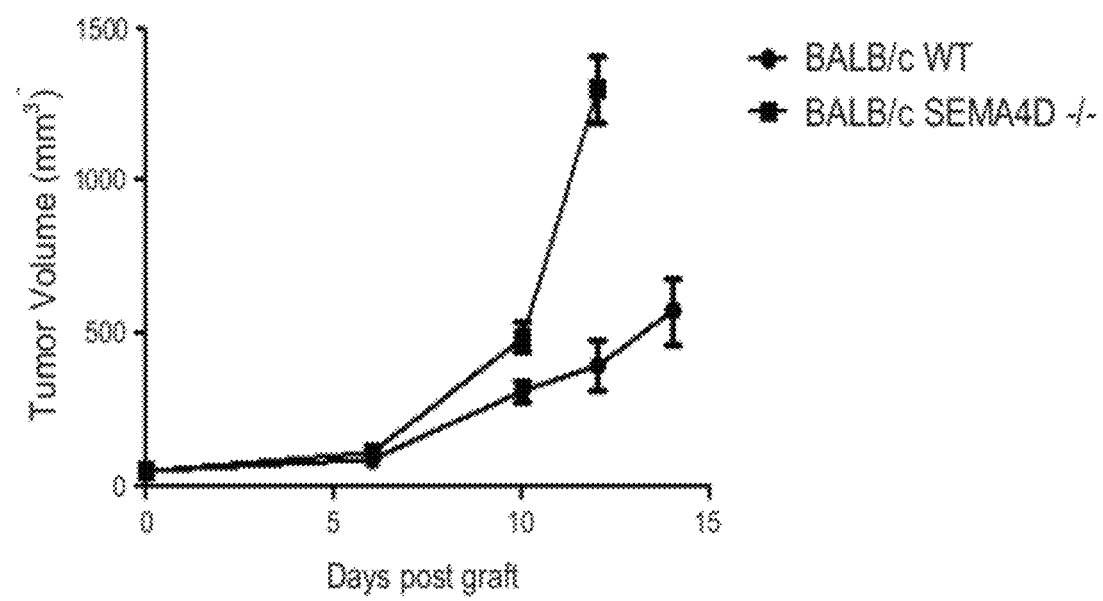

FIG. 17. Change in tumor volume ($mm^3$) is shown for wild-type Balb/c mice and CD100–/– mice ("SEMA4D–/–") after 50.000 EMT6 mouse mammary carcinoma tumor cells were injected into the leg muscle of the mice.

Figure 18:
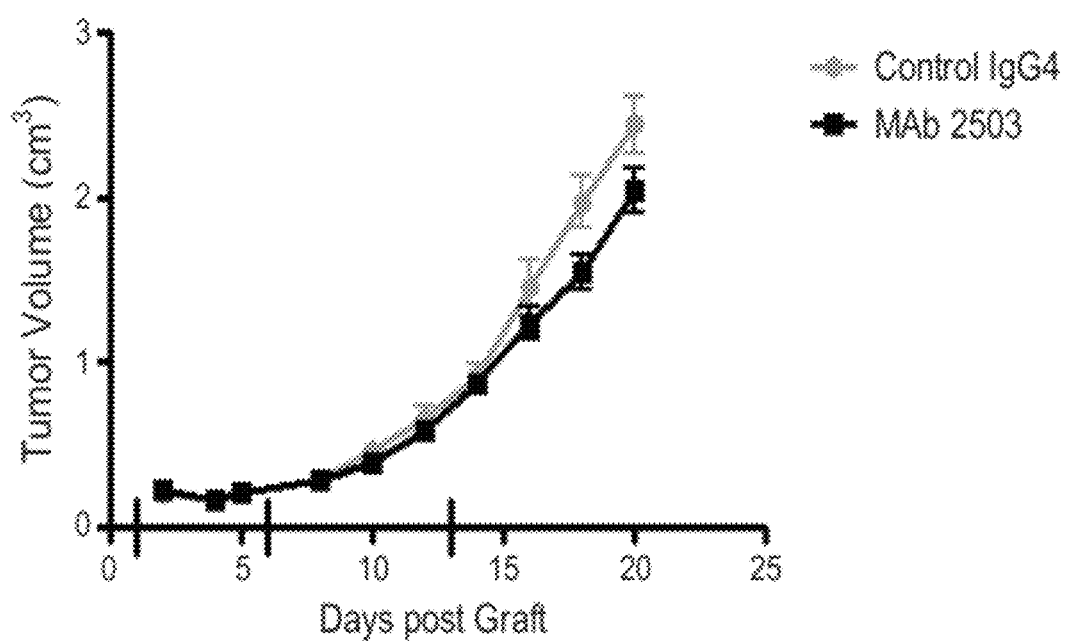

FIG. 18. Change in tumor volume ($mm^3$) is shown for athymic nude mice after two HN12 head and neck tumors/mouse were s.c. injected into the flank muscle of the mice. Results are shown for mice injected with 1 mg MAb 2503 weekly starting on day post graft compared to mice injected with IgG4 control.

FIG. 19. Change in tumor volume ($mm^3$) is shown for athymic nude mice after two HN6 HIf1a mODD head and neck tumors were s.c, injected into the leg muscle of the mice. Results are shown for mice injected with 1 mg MAb 2503 weekly starting on day 1 post graft compared to mice injected with IgG4 control (19A). Pictures of representative tumors from IgG4 control and MAb 2503 treated mice are shown (19B).

FIG. 20. Percent saturation results from single intravenous injection saturation analysis of MAb 2503 in rat. Sprague-Dawley rats were administered a single intravenous injection of MAb 2503 at doses of 0, 0.01, 0.1, 1.0, 10, and 100 mg/kg. A flow cytometry-based saturation assay was performed on lysed whole blood at various time points to determine the percent of the cellular target (SEMA4D) that was saturated with MAb 2503 in male (20A) and female (20B) rats.

Figure 21:
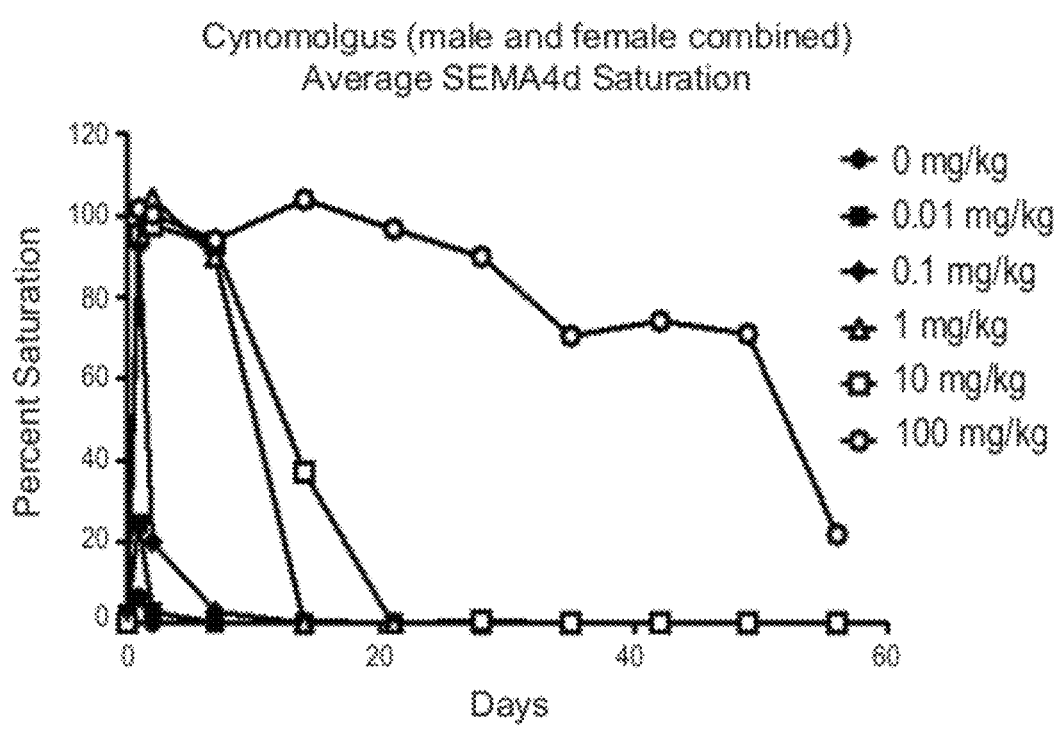

FIG. 21. Percent saturation results from single intravenous injection saturation analysis of MAb 2503 in cynomoigus monkey. Cynomolgus monkeys were administered a single intravenous injection of MAb 2503 at doses of 0, 0.01, 0.1, 1.0, 10, and 100 mg/kg. A flow cytometry-based saturation assay was performed on lysed whole blood at various time points to determine the percent of the cellular target (SEMA4D) that was saturated with MAb 2503 (male and female data were combined).

DETAILED DESCRIPTION OF THE INVENTION

I. Definitions

It is to be noted that the term "a" or "an" entity refers to one or more of that entity; for example, "an anti-CD100 antibody" is understood to represent one or more anti-CD100 antibodies. As such, the terms "a" (or "an"), "one or more," and "at least one" can be used interchangeably herein.

As used herein, the term "tumor" refers to all neoplastic cell growth and proliferation, whether malignant or benign, and all cancerous and pre-cancerous cells and tissues.

"Invasive angiogenesis" refers to the formation of blood vessels for the support of pathological conditions, including malignant and non-malignant tumors as well as the abnormal formation of new blood vessels in macular degeneration.

The terms, "cancer" and "cancerous" refer to or describe the physiological condition in mammals that is typically characterized by unregulated cell growth. Examples of cancer include but are not limited to carcinomas, lymphomas and leukemias.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides that do not possess a defined three-dimensional structure, but rather can adopt a large number of different conformations, are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purpose of the invention, as are native or recombinant polypeptides that have been separated, fractionated, or partially or substantially purified by any suitable technique.

Also included as polypeptides of the present invention are fragments, derivatives, analogs, or variants of the foregoing polypeptides, and any combination thereof. The terms "fragment," "variant," "derivative," and "analog" when referring to anti-CD100 antibodies or antibody polypeptides of the present invention include any polypeptides that retain at least some of the antigen-binding properties of the corresponding antibody or antibody polypeptide of the invention. Fragments of polypeptides of the present invention include proteolytic fragments, as well as deletion fragments, in addition to specific antibody fragments discussed elsewhere herein. Variants of anti-CD100 antibodies and antibody polypeptides of the present invention include fragments as described above, and also polypeptides with altered amino acid sequences due to amino acid substitutions, deletions, or insertions. Variants may occur naturally or be non-naturally occurring. Non-naturally occurring variants may be produced using art-known mutagenesis techniques. Variant polypeptides may comprise conservative or non-conservative amino acid substitutions, deletions, or additions. Variant polypeptides may also be referred to herein as "polypeptide analogs," As used herein a "derivative" of an anti-CD100 antibody or antibody polypeptide refers to a subject polypeptide having one or more residues chemically derivatized by reaction of a functional side group. Also included as "derivatives" are those peptides that contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine. Derivatives of anti-CD100 antibodies and antibody polypeptides of the present invention, may include polypeptides that have been altered so as to exhibit additional features not found on the reference antibody or antibody polypeptide of the invention.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, that has been removed from its native environment. For example, a recombinant polynucleotide encoding an anti-CD100 binding molecule, e.g., an antibody or antigen binding fragment thereof, contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

As used herein, a "coding region" is a portion of nucleic acid that consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an immunoglobulin heavy chain variable region and an immunoglobulin light chain variable region. In addition, a vector, polynucleotide, or nucleic acid of the invention may encode heterologous coding regions, either fused or unfused to a nucleic acid encoding an anti-CD100 antibody or fragment, variant, or derivative thereof. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid that encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions that function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to, ribosome binding sites, translation initiation and termination codons, and elements derived from picornaviruses (particularly an internal ribosome entry site, or TRES, also referred to as a CITE sequence).

In other embodiments, a polynucleotide of the present invention is RNA, for example, in the form of messenger RNA (mRNA).

Polynucleotide and nucleic acid coding regions of the present invention may be associated with additional coding regions that encode secretory or signal peptides, which direct the secretion of a polypeptide encoded by a polynucleotide of the present invention. According to the signal hypothesis, proteins secreted by mammalian cells have a signal peptide or secretory leader sequence that is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

A "binding molecule" or "antigen binding molecule" of the present invention refers in its broadest sense to a molecule that specifically binds an antigenic determinant. In one embodiment, the binding molecule specifically binds to CD100, e.g., a transmembrane CD100 polypeptide of about 150 kDa or a soluble CD100 polypeptide of about 120 kDa (commonly referred to as sCD100). In a another embodiment, a binding molecule of the invention is an antibody or an antigen binding fragment thereof. In another embodiment, a binding molecule of the invention comprises at least one heavy or light chain CDR of an antibody molecule. In another embodiment, a binding molecule of the invention comprises at least two CDRs from one or more antibody molecules. In another embodiment, a binding molecule of the invention comprises at least three CDRs from one or more antibody molecules. In another embodiment, a binding molecule of the invention comprises at least four CDRs from one or more antibody molecules. In another embodiment, an a binding molecule of the invention comprises at least five CDRs from one or more antibody molecules. In another embodiment, a binding molecule of the invention comprises at least six CDRs from one or more antibody molecules.

The present invention is directed to certain anti-CD100 antibodies, or antigen-binding fragments, variants, or derivatives thereof. Unless specifically referring to full-sized antibodies such as naturally occurring antibodies, the term "anti-CD100 antibodies" encompasses full-sized antibodies as well as antigen-binding fragments, variants, analogs, or derivatives of such antibodies, e.g., naturally occurring antibody or immunoglobulin molecules or engineered antibody molecules or fragments that bind antigen in a manner similar to antibody molecules.

As used herein, "human" or "fully human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example, in U.S. Pat. No. 5,939,598 by Kucherlapati et "Human" or "fully human" antibodies also include antibodies comprising at least the variable domain of a heavy chain, or at least the variable domains of a heavy chain and a light chain, where the variable domain(s) have the amino acid sequence of human immunoglobulin variable domain(s).

"Human" or "fully human" antibodies also include "human" or "fully human" antibodies, as described above, that comprise, consist essentially of, or consist of, variants (including derivatives) of antibody molecules (e.g., the VH regions and/or VL regions) described herein, which antibodies or fragments thereof immunospecifically bind to a CD100 polypeptide or fragment or variant thereof. Standard techniques known to those of skill in the art can be used to introduce mutations in the nucleotide sequence encoding a human anti-CD100 antibody, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH region, VHCDR1. VHCDR2, VHCDR3, region, VLCDR1VLCDR2, or VLCDR3.

In certain embodiments, the amino acid substitutions are conservative amino acid substitution, discussed further below. Alternatively, mutations can be introduced randomly along all or part of the coding sequence, such as by saturation mutagenesis, and the resultant mutants can be screened for biological activity to identify mutants that retain activity (e.g., the ability to bind a CD100 polypeptide, e.g., human, murine, or both human and murine CD100). Such variants (or derivatives thereof) of "human" or "fully human" antibodies can also be referred to as human or fully human antibodies that are "optimized" or "optimized for antigen binding" and include antibodies that have improved affinity to antigen.

The terms "antibody" and "immunoglobulin" are used interchangeably herein. An antibody or immunoglobulin comprises at least the variable domain of a heavy chain, and normally comprises at least the variable domains of a heavy chain and a light chain. Basic immunoglobulin structures in vertebrate systems are relatively well understood. See, e.g., Harlow et al. (1988) Antibodies: A Laboratory Manual (2nd ed.; Cold Spring Harbor Laboratory Press).

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant invention. All immunoglobulin classes are clearly within the scope of the present invention, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VL or VK) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the VL domain and VH domain, or subset of the complementarity determining regions (CDRs) within these variable domains, of an antibody combine to form the variable region that defines a three dimensional antigen binding site. This quaternary antibody structure forms the antigen binding site present at the end of each arm of the Y. More specifically, the antigen binding site is defined by three CDRs on each of the VH and VL chains. In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., *Nature* 363:446-448 (1993).

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a sheet conformation and the CDRs form loops that connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable domain by one of ordinary skill in the art, since they have been precisely defined (see below).

In the case where there are two or more definitions of a term that is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al. (1983) U.S. Dept. of Health and Human Services, "Sequences of Proteins of Immunological Interest" and by Chothia and Lesk, *J. Mol. Biol.* 196:901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues that encompass the CDRs as defined by each of the above cited references are set forth below in Table 1 as a comparison. The exact residue numbers that encompass a particular CDR will vary depending on the sequence and size of the CDR. Those skilled in the art can routinely determine which residues comprise a particular CDR given the variable region amino acid sequence of the antibody.

TABLE 1

CDR Definitions[1]

|  | Kabat | Chothia |
|---|---|---|
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table 1 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al. (1983) U.S. Dept. of Health and Human Services, "Sequence of Proteins of Immunological Interest." Unless otherwise specified, references to the numbering of specific amino acid residue positions in an anti-CD100 antibody or antigen-binding fragment, variant, or derivative thereof of the present invention are according to the Kabat numbering system.

Antibodies or antigen-binding fragments, variants, or derivatives thereof of the invention include, but are not limited to, polyclonal, monoclonal, multispecific, human, humanized, primatized, or chimeric antibodies, single-chain antibodies, epitope-binding fragments, e.g., Fab, Fab' and F(ab')$_2$, Fd, Fvs, single-chain Fvs (scFv), disulfide-linked Fvs (sdFv), fragments comprising either a VL or VH domain, fragments produced by a Fab expression library, and anti-idiotypic (anti-Id) antibodies (including, e.g., anti-Id antibodies to anti-CD100 antibodies disclosed herein). ScFv molecules are known in the art and are described, e.g., in U.S. Pat. No. 5,892,019. Immunoglobulin or antibody molecules of the invention can be of any type IgG, IgE, IgD, IgA, and IgY), class (e.g., IgG1, IgG2, IgG3, IgG4, IgA1, and IgA2, etc.), or subclass of immunoglobulin molecule.

As used herein, the term "heavy chain portion" includes amino acid sequences derived from an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. For example, a binding polypeptide for use in the invention may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the invention comprises a polypeptide chain comprising a CH3 domain. Further, a binding polypeptide for use in the invention may lack at least a portion of a CH2 domain (e.g., all or part of a CH2 domain). As set forth above, it will be understood by one of ordinary skill in the art that these domains (e.g., the heavy chain portions) may be modified such that they vary in amino acid sequence from the naturally occurring immunoglobulin molecule.

In certain anti-CD100 antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the invention are not identical. For example, each monomer may comprise a different target binding site, forming, for example, a bispecific antibody.

The heavy chain portions of a binding molecule for use in the diagnostic and treatment methods disclosed herein may be derived from different immunoglobulin molecules. For example, a heavy chain portion of a polypeptide may comprise a $C_{H1}$ domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain, e.g., a kappa or lambda light chain. Preferably, the light chain portion comprises at least one of a VL or CL domain.

Anti-CD100 antibodies, or antigen-binding fragments, variants, or derivatives thereof disclosed herein may be described or specified in terms of the epitope(s) or portion(s) of an antigen, e.g., a target polypeptide disclosed herein (e.g., CD100) that they recognize or specifically bind. The portion of a target polypeptide that specifically interacts with the antigen binding domain of an antibody is an "epitope," or an "antigenic determinant." A target polypeptide may comprise a single epitope, but typically comprises at least two epitopes, and can include any number of epitopes, depending on the size, conformation, and type of antigen. Furthermore, it should be noted that an "epitope" on a target polypeptide may be or may include non-polypeptide elements, e.g., an epitope may include a carbohydrate side chain.

The minimum size of a peptide or polypeptide epitope for an antibody, is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. A peptide or polypeptide epitope recognized by anti-CD100 antibodies of the present invention may contain a sequence of at least 4, at least 5, at least 6, at least 7, more preferably at least 8, at least 9, at least 10, at least 15, at least 20, at least 25, or between about 15 to about 30 contiguous or non-contiguous amino acids of CD100.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to quality the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody that "preferentially binds" to a given epitope would more likely bind to that epitope than to a related epitope, even though such an antibody may cross-react with the related epitope.

By way of non-limiting example, an antibody may be considered to bind a first epitope preferentially if it binds said first epitope with a dissociation constant ($K_D$) that is less than the antibody's $K_D$ for the second epitope. In another non-limiting example, an antibody may be considered to bind a first antigen preferentially if it binds the first epitope with an affinity that is at least one order of magnitude less than the antibody's $K_D$ for the second epitope. In another non-limiting example, an antibody may be considered to bind a first epitope preferentially if it binds the first epitope with an affinity that is at least two orders of magnitude less than the antibody's $K_D$ for the second epitope.

In another non-limiting example, an antibody may be considered to bind a first epitope preferentially if it binds the first epitope with an off rate (k(off)) that is less than the antibody's k(off) for the second epitope. In another non-limiting example, an antibody may be considered to bind a first epitope preferentially if it binds the first epitope with an affinity that is at least one order of magnitude less than the antibody's k(off) for the second epitope. In another non-limiting example, an antibody may be considered to bind a first epitope preferentially if it binds the first epitope with an affinity that is at least two orders of magnitude less than the antibody's k(off) for the second epitope. An antibody or antigen-binding fragment, variant, or derivative disclosed herein may be said to bind a target polypeptide disclosed herein (e.g., CD100, e.g., human, murine, or both human and murine CD100) or a fragment or variant thereof with an off rate (k(off)) of less than or equal to $5\times10^{-2}$ sec$^{-1}$, $10^{-2}$ sec$^{-1}$, $5\times10^{-3}$ sec$^{-1}$ or $10^{-3}$ sec$^{-1}$. More preferably, an antibody of the invention may be said to bind a target polypeptide disclosed herein (e.g., CD100, e.g., human, murine, or both human and murine CD100) or a fragment or variant thereof with an off rate (k(off)) less than or equal to $5\times10^{-4}$ sec$^{-1}$, $10^{-4}$ sec$^{-1}$, $5\times10^{-5}$ sec$^{-1}$, or $10^{-5}$ sec$^{-1}$, $5\times10^{-6}$ sec$^{-1}$, $10^{-6}$ sec$^{-1}$, $5\times10^{-7}$ sec$^{-1}$ or $10^{-7}$ sec$^{-1}$.

An antibody or antigen-binding fragment, variant, or derivative disclosed herein may be said to bind a target polypeptide disclosed herein (e.g., CD100, e.g., human, murine, or both human and murine CD100) or a fragment or variant thereof with an on rate (k(on)) of greater than or equal to $10^3$ M$^{-1}$ sec$^{-1}$, $5\times10^3$ M$^{-1}$ sec$^{-1}$, $10^4$ M$^{-1}$ sec$^{-1}$ or $5\times10^4$ M$^{-1}$ sec$^{-1}$. More preferably, an antibody of the invention may be said to bind a target polypeptide disclosed herein (e.g., CD100, e.g., human, murine, or both human and murine CD100) or a fragment or variant thereof with an on rate (k(on)) greater than or equal to $10^5$ M$^{-1}$ sec$^{-1}$, $5\times10^5$ M$^{-1}$ sec$^{-1}$, $10^6$ M$^{-1}$ sec$^{-1}$ or $5\times10^6$ M$^{-1}$ sec$^{-1}$ or $10^7$ M$^{-1}$ sec$^{-1}$.

An antibody is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of an immunoglobulin molecule. See, e.g., Harlow et al. (1988) Antibodies: A Laboratory Manual (Cold Spring harbor Laboratory Press, 2nd ed.) pages 27-28. As used herein, the term "avidity" refers to the overall stability of the complex between a population of immunoglobulins and an antigen; that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

Anti-CD100 antibodies or antigen-binding fragments, variants, or derivatives eof of the invention may also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, may actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody may be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody may be deemed "highly specific" for a certain epitope, if it does not bind any other analog, ortholog, or homolog of that epitope.

Anti-CD100 binding molecules, e.g., antibodies or antigen-binding fragments, variants or derivatives thereof, of the invention may also be described or specified in terms of their binding affinity to a polypeptide of the invention, e.g., CD100, e.g., human, murine, or both human and murine CD100. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M. In certain embodiments, the anti-CD100 binding molecule, e.g., an antibody or antigen binding fragment thereof, of the invention binds human CD100 with a Kd of about $5 \times 10^{-9}$ to about $6 \times 10^{-9}$. In another embodiment, the anti-CD100 binding molecule, e.g., an antibody or antigen binding fragment thereof, of the invention binds murine CD100 with a Kd of about $1 \times 10^{-9}$ to about $2 \times 10^{-9}$.

Anti-CD100 antibodies or antigen binding am variants or derivatives eof of the invention may be "multispecific," bispecific, trispecific, or of greater muitispecificity, meaning that it recognizes and binds to two or more different epitopes present on one or more different antigens (e.g., proteins) at the same time. Thus, whether an anti-CD100 antibody is "monospecific" or "multispecific," e.g., "bispecific," refers to the number of different epitopes with which a binding polypeptide reacts. Multispecific antibodies may be specific for different epitopes of a target polypeptide described herein or may be specific for a target polypeptide as well as for a heterologous epitope, such as a heterologous polypeptide or solid support material.

As used herein the term "valency" refers to the number of potential binding domains, e.g., antigen binding domains present in a binding polypeptide or CD100 binding molecule, e.g., an antibody or antigen binding fragment thereof. Each binding domain specifically binds one epitope. When a binding polypeptide or CD100 binding molecule comprises more than one binding domain, each binding domain may specifically bind the same epitope, for an antibody with two binding domains, termed "bivalent monospecific," or to different epitopes, for an antibody with two binding domains, termed "bivalent bispecific." An antibody or antigen binding fragment thereof may also be bispecific and bivalent for each specificity (termed "bispecific tetravalent antibodies"). In another embodiment, tetravalent minibodies or domain deleted antibodies can be made.

Bispecific bivalent antibodies, and methods of making them, are described, for instance in U.S. Pat. Nos. 5,731,168; 5,807,706; 5,821,333; and U.S. Patent Appl. Publ. Nos. 2003/020734 and 2002/0155537, the disclosures of all of which are incorporated by reference herein. Bispecific tetravalent antibodies, and methods of making them are described, for instance, in WO 02/096948 and WO 00/14788, the disclosures of both of which are incorporated by reference herein. See generally, PCT publications WO 93/17715; WO 92/08802; WO 91/00360; WO 92/05793; Tutt et al., J. Immunol. 147:60-69 (1991); U.S. Pat. Nos. 4,471,893; 4,714,681; 4,925,618; 5,573,920; 5,601,819; Kostelny et al., J. Immunol. 148: 1547-1553 (1992).

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E A et al.). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux et al., *J. Immunol.* 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant invention) is obtained from a second species. In preferred embodiments the target binding region or site will be from anon-human source mouse or primate) and the constant region is human (for example, monoclonal antibody (MAb) 2368 described herein).

As used herein, the term "engineered antibody" refers to an antibody in which the variable domain in either the heavy or light chain or both is altered by at least partial replacement of one or more CDRs from, an antibody of known specificity and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. An engineered antibody in which one or more "donor" CDRs from a non-human antibody of known specificity is grafted into a human heavy or light chain framework region is referred to herein as a "humanized antibody." It may not be necessary to replace all of the CDRs with the complete CDRs from the donor variable domain to transfer the antigen binding capacity of one variable domain to another. Rather, it may only be necessary to transfer those residues that are necessary to maintain the activity of the target binding site.

It is further recognized that the framework regions within the variable domain in a heavy or light chain, or both, of a humanized antibody may comprise solely residues of human origin, in which case these framework regions of the humanized antibody are referred to as "fully human framework regions" (for example, MAb 2503). Alternatively, one or more residues of the framework region(s) of the donor variable domain can be engineered within the corresponding position of the human framework region(s) of a variable domain in a heavy or light chain, or both, of a humanized antibody if necessary to maintain proper binding or to enhance binding to the CD100 antigen. A human framework region that has been engineered in this manner would thus comprise a mixture of human and donor framework residues, and is referred to herein as a "partially human framework region."

For example, humanization of an anti-CD100 antibody can be essentially performed following the method of Winter and co-workers (Jones et al., *Nature* 321:522-525 (1986); Riechmann et al., *Nature* 332:323-327 (1988); Verhoeyen et al., *Science* 239:1534-1536 (1988)), by substituting rodent or mutant rodent CDRs or CDR sequences for the corresponding sequences of a human anti-CD100 antibody. See also U.S. Pat. Nos. 5,225,539; 5,585,089; 5,693,761; 5,693,762; 5,859, 205; herein incorporated by reference. The resulting humanized anti-CD100 antibody would comprise at least one rodent or mutant rodent CDR within the fully human framework regions of the variable domain of the heavy and/or light chain of the humanized antibody. In some instances, residues within the framework regions of one or more variable domains of the humanized anti-CD100 antibody are replaced by corresponding non-human (for example, rodent) residues (see, for example, U.S. Pat. Nos. 5,585,089; 5,693,761; 5,693,762; and 6,180,370), in which case the resulting humanized anti-CD100 antibody would comprise partially human framework regions within the variable domain of the heavy and/or light chain.

Furthermore, humanized antibodies may comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the CDRs correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al., *Nature* 331:522-525 (1986); Riechmann et al., *Nature* 332:323-329 (1988); and Presta, *Curr. Op. Strict. Biol.* 2:593-596 (1992); herein incorporated by reference. Accordingly, such "humanized" antibodies may include antibodies wherein substantially less than an intact human variable domain has been substituted by the corresponding sequence from a non-human species. In practice, humanized antibodies are typically human antibodies in which some CDR residues and possibly some framework residues are substituted by residues from analogous sites in rodent antibodies. See, for example, U.S. Pat. Nos. 5,225,539; 5,585,089; 5,693,761; 5,693,762; 5,859,205. See also U.S. Pat. No. 6,180,370, and International Publication No. WO 01/27160, where humanized antibodies and techniques for producing humanized antibodies having improved affinity for a predetermined antigen are disclosed.

As used herein, the terms "linked," "fused," or "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two or more segments that correspond to polypeptides encoded by the original ORFs (which segments are not normally so joined in nature). Although the reading frame is thus made continuous throughout the fused segments, the segments may be physically or spatially separated by, for example, in-frame linker sequence. For example, polynucleotides encoding the CDRs of an immunoglobulin variable region may be fused, in-frame, but be separated by a polynucleotide encoding at least one immunoglobulin framework region or additional CDR regions, as long as the "fused" CDRs are co-translated as part of a continuous polypeptide.

In the context of polypeptides, a "linear sequence" or a "sequence" is an order of amino acids in a polypeptide in an amino to carboxyl terminal direction in which residues that neighbor each other in the sequence are contiguous in the primary structure of the polypeptide.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, the terms "treat" or "treatment" refer to both therapeutic treatment and prophylactic or preventative measures, wherein the object is to prevent or slow down (lessen) an undesired physiological change or disorder, such as the progression of multiple sclerosis, arthritis, or cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, and so on.

As used herein, phrases such as "a subject that would benefit from administration of an anti-CD100 antibody" and "an animal in need of treatment" includes subjects, such as mammalian subjects, that would benefit from administration of an anti-CD100 antibody used, e.g., for detection of an anti-CD100 polypeptide (e.g., for a diagnostic procedure) and/or from treatment, i.e., palliation or prevention of a disease, with an anti-CD100 antibody. As described in more detail herein, an anti-CD100 antibody can be used in unconjugated form or can be conjugated, e.g., to a drug, prodrug, or an isotope.

II. Target Polypeptide Description

As used herein, the terms "CD100" and "CD100 polypeptide" are used interchangably. In certain embodiments, CD100 is expressed on the surface of or secreted by a cell. In another embodiment, CD100 is membrane bound. In another embodiments, CD100 is soluble, e.g., sCD100. In another embodiments, CD100 may include a full-sized CD or a fragment thereof, or a CD100 variant polypeptide, wherein the fragment of CD100 or CD100 variant polypeptide retains some or all functional properties of the full-sized CD100.

The full-sized human CD100 protein is a homodimeric transmembrane protein consisting of two polypeptide chains of 150 kDa. CD100 belongs to the semaphorin family of cell surface receptors and is also referred to as SEMA4D. Both human and mouse Sema4D/CD100 are proteolytically cleaved from their transmembrane form to generate 120-kDa soluble forms, indicating the existence of two Sema4D isoforms (Kumanogoh et al., *J. Cell Science* 116(7):3464 (2003)). Semaphorins consist of soluble and membrane-bound proteins that were originally defined as axonal-guidance factors which play an important role in establishing precise connections between neurons and their appropriate target. Structurally considered a class IV semaphorin, CD100 consists of an amino-terminal signal sequence followed by a characteristic 'Sema' domain, which contains 17 conserved cysteine residues, an Ig-like domain, a lysine-rich stretch, a hydrophobic transmembrane region, and a cytoplasmic tail.

Each polypeptide chain of CD100 includes a signal sequence of about 13 amino acids followed by a semaphorin domain of about 512 amino acids, an immunoglobulin-like (Ig-like) domain of about 65 amino acids, a lysine-rich stretch of 104 amino acids, a hydrophobic transmembrane region of about 19 amino acids, and a cytoplasmic tail of 110 amino acids, A consensus site for tyrosine phosphorylation in the cytoplasmic tail supports the predicted association of CD100 with a tyrosine kinase (Schiossman, et al., Eds. (1995) Leucocyte Typing V (Oxford University Press, Oxford).

Two types of receptors have been identified for CD100. One of the receptors, Plexin-B1, is expressed in non-lymphoid tissues and has been shown to be a high affinity (1 nM) receptor for CD100 (Tamagnone et al., *Cell* 99:71-80 (1999)). CD100 stimulation of Plexin B1 signaling has been shown to induce growth cone collapse of neurons, and to induce process extension collapse and apoptosis of oligodendrocytes (Giraudon et al., *J. Immunol.* 172:1246-1255 (2004); Giraudon et al., *NeuroMolecular Med.* 7:207-216 (2005)). After binding to CD100, Plexin B1 signaling mediates the inactivation of R-Ras, leading to a decrease in the integrin mediated attachment to the extracellular Matrix, as well as to activation of Rho, leading to cell collapse by reorganization of the cytoskeleton. See Kruger et al., *Nature Rev. Mol. Cell Biol.* 6:789-800 (2005); Pasterkamp, *TRENDS in Cell Biology* 15:61-64 (2005)).

In lymphoid tissues CD72 is utilized as a low affinity (300 nM) CD100 receptor (Kurnanogoh et al., *Immunity* 13:621-631 (2000)). B cells and APCs express CD72, and anti-CD72 antibodies have many of the same effects as sCD100, such as enhancement of CD40-induced B cell responses and B cell shedding of CD23. CD72 is thought to act as a negative regulator of B cell responses by recruiting the tyrosine phosphatase SHP-1, which can associate with many inhibitory receptors. Interaction of CD100 with CD72 results in the dissociation of SFIP-1, and the loss of this negative activation signal. CD100 has been shown to promote T cell stimulation and B cell aggregation and survival in vitro. The addition of CD100-expressing cells or sCD100 enhances CD40-induced B cell proliferation and immunoglobulin production in vitro, and accelerates in vivo antibody responses (Ishida et al., *Inter. Immunol.* 15:1027-1034 (2003); Kurnanogoh and H. Kukutani, *Trends in Immunol.* 22:670-676 (2001)). sCD100 enhances the CD40 induced maturation of DCs, including up-regulation of costimulatory molecules and increased secretion of IL-12. In addition, sCD100 can inhibit immune cell migration, which can be reversed by addition of blocking anti-CD100 mouse antibodies (Elhabazi et al., *J. Immunol.* 166:4341-4347 (2001); Delaire et al., *J. Immunol.* 166:4348-4354 (2001)).

Sema4D is expressed at high levels in lymphoid organs, including the spleen, thymus, and lymph nodes, and in non-lymphoid organs, such as the brain, heart, and kidney. In lymphoid organs, Sema4D is abundantly expressed on resting T cells but only weakly expressed on resting B cells and antigen-presenting cells (APCs), such as dendritic cells (DCs).

Cellular activation increases the surface expression of CD100 as well as the generation of soluble CD100 (sCD100). The expression pattern of CD100 suggests that it plays an important physiological as well as pathological role in the immune system. CD100 has been shown to promote B cell activation, aggregation and survival; enhance CD40-induced proliferation and antibody production; enhance antibody response to T cell dependent antigens; increase T cell proliferation; enhance dendritic cell maturation and ability to stimulate T cells; and is directly implicated in demyelination and axonal degeneration (Shi et al., *Immunity* 13:633-642 (2000); Kumanogoh et al., *J Immunol* 169:1175-1181 (2002); and Watanabe et al., *J Immunol* 167:4321-4328 (2001)).

CD100 knock out (CD100−/−) mice have provided additional evidence that CD100 plays an important role in both humoral and cellular immune responses. There are no known abnormalities of non-lymphoid tissues in CD100−/− mice. Dendritic cells (PCs) from the CD100−/− mice have poor allostimulatory ability and show defects in expression of costimulatory molecules, which can be rescued by the addition of sCD100. Mice deficient in CD100 (CD100−/−) fail to develop experimental autoimmune encephalomyelitis induced by myelin oligodendrocyte glycoprotein peptide, because myelin oligodendrocyte glycoprotein-specific T cells are not generated in the absence of CD100 (Kumanogoh et al., *J Immunol* 169:1175-1181 (2002)). A significant amount of soluble CD100 is also detected in the sera of autoimmunity-prone MRL/lpr mice (model of systemic autoimmune diseases such as SLE), but not in normal mice. Further, the levels of sCD100 correlate with levels of autoantibodies and increase with age (Wang et al., *Blood* 97:3498-3504 (2001)). Soluble CD100 has also been shown to accumulate in the cerebral spinal fluid and sera of patients with demyelinating disease, and sCD100 induces apoptosis of human pluripotent neural precursors (Dev cells), and both inhibits process extension and induces apoptosis of rat oligodendrocytes in vitro (Giraudon et al., *J Immunol* 172(2): 1246-1255 (2004)). This apoptosis was blocked by an anti-CD100 MAb.

III. Anti-CD100 Antibodies

Antibodies that bind CD100 have been described the art. See, for example US Publ. No. 2008/0219971 A1, International Patent Application WO 93/14125 and Herold et al., *Int. Immunol.* 7(1): 1-8 (1995), each of which is herein incorporated in its entirety by reference.

The antibodies of the invention comprise anti-CD100 antibodies or antigen-binding fragments, variants, or derivatives thereof that bind to CD100, e.g., MAb 2503, MAb 67, and MAb 76. In certain embodiments the anti-CD100 antibodies bind human, murine, or both human and murine CD100. In other embodiments, the anti-CD100 antibodies block CD100 binding to its receptor, e.g., Plexin-B.

In one embodiment, the present invention provides an isolated binding molecule, e.g., an antibody or antigen binding fragment thereof, which specifically binds to the same CD100 epitope as monoclonal antibody 2503, 67, or 76. In another embodiment, the present invention provides an isolated binding molecule, e.g., an antibody or antigen binding fragment thereof, which specifically binds to CD100, and competitively inhibits monoclonal antibody 2503, 67, or 76 from specifically binding to CD100, e.g., human, murine, or both human and murine CD100.

In certain embodiments, the binding molecule of the invention has an amino acid sequence that has at least about 80%, about 85%, about 88%, about 89%, about 90%, about 91%, about 92%, about 93%, about 94%, or about 95% sequence identity to the amino acid sequence for the reference anti-CD100 antibody molecule. In a further embodiment, the binding molecule shares at least about 96%, about 97%, about 98%, about 99%, or 100% sequence identity to the reference antibody.

In another embodiment, the present invention provides an isolated antibody or antigen-binding fragment thereof comprising, consisting essentially of, or consisting of an immunoglobulin heavy chain variable domain (VH domain), where at least one of the CDRs of the VH domain has an amino acid sequence that is at least about 80%, about 85%, about 90%, about 95%, about 96%, about 97%, about 98%, about 99%, or identical to CDR1, CDR2 or CDR3 of SEQ NO: 9 or 10.

In another embodiment, the present invention provides an isolated antibody or antigen-binding fragment thereof comprising, consisting essentially of, or consisting of an immunoglobulin heavy chain variable domain (VH domain), where at least one of the CDRs of the VH domain has an amino acid sequence that is at least about 80%, about 85%, about 90%, about 95%, about 96%, about 97%, about 98%, about 99%, or identical to SEQ ID NO: 6, SEQ ID NO: 7, or SEQ ID NO: 8.

In another embodiment, the present invention provides an isolated antibody or antigen-binding fragment thereof comprising, consisting essentially of, or consisting of an immunoglobulin heavy chain variable domain (VH domain), where at least one of the CDRs of the VH domain has an amino acid sequence identical, except for 1, 2, 3, 4, or 5 conservative amino acid substitutions, to SEQ ID NO: 6, SEQ ID NO: 7, or SEQ ID NO: 8.

In another embodiment, the present invention provides an isolated antibody or antigen-binding fragment thereof comprising, consisting essentially of or consisting of a VH domain that has an amino acid sequence that is at least about 80%, about 85%, about 90%, about 91%, about 92%, about 93%, about 94%, about 95%, about 96%, about 97%, about 98%, about 99%, or 100% identical to SEQ ID NO: 9 or SEQ ID NO: 10, wherein an anti-CD100 antibody comprising the encoded VH domain specifically or preferentially binds to CD100.

In another embodiment, the present invention provides an isolated antibody or antigen-binding fragment thereof comprising, consisting essentially of, or consisting of an immunoglobulin light chain variable domain (VL domain), where at least one of the CDRs of the VL domain has an amino acid sequence that is at least about 80%, about 85%, about 90%, about 95%, about 96%, about 97%, about 98%, about 99%, or identical to CDR1, CDR2 or CDR3 of SEQ ID NO: 17 or 18.

In another embodiment, the present invention provides an isolated antibody or antigen-binding fragment thereof comprising, consisting essentially of, or consisting of an immunoglobulin light chain variable domain (VL domain), where at least one of the CDRs of the VL domain has an amino acid sequence that is at least about 80%, about 85%, about 90%, about 95%, about 96%, about 97%, about 98%, about 99%, or identical to SEQ ID NO: 14, SEQ ID NO: 15, or SEQ ID NO: 16.

In another embodiment, the present invention provides an isolated antibody or antigen-binding fragment thereof comprising, consisting essentially of, or consisting of an immunoglobulin light chain variable domain (VL domain), where at least one of the CDRs of the VL domain has an amino acid sequence identical, except for 1, 2, 3, 4, or 5 conservative amino acid substitutions, to SEQ ID NO: 14, SEQ ID NO: 15, or SEQ ID NO: 16.

In a further embodiment, the present invention includes an isolated antibody or antigen-binding fragment thereof comprising, consisting essentially of or consisting of a VL domain that has an amino acid sequence that is at least about 80%, about 85%, about 90%, about 91%, about 92%, about 93%, about 94%, about 95%, about 96%, about 97%, about 98%, about 99%, or 100% identical to SEQ ID NO: 17 or SEQ ID NO: 18, wherein an anti-CD100 antibody comprising the encoded VL domain specifically or preferentially binds to CD100.

Suitable biologically active variants of the anti-CD100 antibodies of the invention can be used in the methods of the present invention. Such variants will retain the desired binding properties of the parent anti-CD100 antibody. Methods for making antibody variants are generally available in the art.

Methods for mutagenesis and nucleotide sequence alterations are well known in the art. See, for example, Walker and Gaastra, eds. (1983) Techniques in Molecular Biology (MacMillan Publishing Company, New York); Kunkel, *Proc. Natl. Acad. Sci. USA* 82:488-492 (1985); Kunkel et al., *Methods Enzymol.* 154:367-382 (1987); Sambrook et al. (1989) Molecular Cloning: A Laboratory Manual (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest may be found in the model of Dayhoff et al. (1978) in Atlas of Protein Sequence and Structure (Natl. Biomed. Res. Found., Washington, D.C.), pp. 345-352, herein incorporated by reference in its entirety. The model of Dayhoff et al. uses the Point Accepted Mutation (PAM) amino acid similarity matrix (PAM 250 matrix) to determine suitable conservative amino acid substitutions. Conservative substitutions, such as exchanging one amino acid with another having similar properties, may be preferred. Examples of conservative amino acid substitutions as taught by the PAM 250 matrix of the Dayhoff et al. model include, but are not limited to, Gly↔Ala, Val↔Ile↔Leu, Asp↔Glu, Lys↔Arg, Asn↔Gln, and Phe↔Trp↔Tyr.

In constructing variants of the anti-CD100 binding molecule, e.g., an antibody or antigen-binding fragment thereof, polypeptides of interest, modifications are made such that variants continue to possess the desired properties, e.g., being capable of specifically binding to a CD100, e.g., human, murine, or both human and murine CD100, expressed on the surface of or secreted by a cell and having CD100 blocking activity, as described herein. Obviously, any mutations made in the DNA encoding the variant polypeptide must not place the sequence out of reading frame and preferably will not create complementary regions that could produce secondary mRNA structure. See EP Patent Application Publication No. 75,444.

Methods for measuring anti-CD100 binding molecule, e.g., an antibody or antigen-binding fragment thereof, binding specificity include, but are not limited to, standard competitive binding assays, assays for monitoring immunoglobulin secretion by T cells or B cells, T cell proliferation assays, apoptosis assays, ELISA assays, and the like. See, for example, such assays disclosed in WO 93/14125; Shi et al., *Immunity* 13:633-642 (2000); Kumanogoh et al., *Immunol* 169:1175-1181 (2002); Watanabe et al., *J Immunol* 167: 4321-4328 (2001); Wang et al., *Blood* 97:3498-3504 (2001); and Giraudon et al., *J Immunol* 172(2):1246-1255 (2004), all of which are herein incorporated by reference.

When discussed herein whether any particular polypeptide, including the constant regions, CDRs, VH domains, or VL domains disclosed herein, is at least about 65%, about 70%, about 75%, about 80%, about 85%, about 90%, about 91%, about 92%, about 93%, about 94%, about 95%, about 96%, about 97%, about 98%, about 99%, or even about 100% identical to another polypeptide, the % identity can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman (1981) *Adv. Appl. Math.* 2:482-489, to find the best segment of homology between two sequences. When using BESTFIT or any other sequence alignment program to determine whether a particular sequence is, for example, 95% identical to a reference sequence according to the present invention, the parameters are set, of course, such that, the percentage of identity is calculated over the full length of the reference polypeptide sequence and that gaps in homology of up to 5% of the total number of amino acids in the reference sequence are allowed.

For purposes of the present invention, percent sequence identity may be determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman (1981) *Adv. Appl. Math.* 2:482-189. A variant may, for example, differ from a reference anti-CD100 antibody (e.g., MAb 2503, 67 or 76) by as few as 1 to 15 amino acid residues, as few as 1 to 10 amino acid residues, such as 6-10, as few as 5, as few as 4, 3, 2, or even 1 amino acid residue.

The precise chemical structure of a polypeptide capable of specifically binding CD100 and retaining the desired CD100 blocking activity depends on a number of factors. As ionizable amino and carboxyl groups are present in the molecule, a particular polypeptide may be obtained as an acidic or basic salt, or in neutral form. All such preparations that retain their biological activity when placed in suitable environmental conditions are included in the definition of anti-CD100 antibodies as used herein. Further, the primary amino acid sequence of the polypeptide may be augmented by derivatization using sugar moieties (glycosylation) or by other supplementary molecules such as lipids, phosphate, acetyl groups and the like. It may also be augmented by conjugation with saccharides. Certain aspects of such augmentation are accomplished through post-translational processing systems of the producing host; other such modifications may be introduced in vitro. In any event, such modifications are included in the definition of an anti-CD100 antibody used herein so long as the desired properties of the anti-CD100 antibody are not destroyed. It is expected that such modifications may quantitatively or qualitatively affect the activity, either by enhancing or diminishing the activity of the polypeptide, in the various assays. Further, individual amino acid residues in the chain may be modified by oxidation, reduction, or other derivatization, and the polypeptide may be cleaved to obtain fragments that retain activity. Such alterations that do not destroy the desired properties (e.g., binding specificity for CD100, binding affinity, and CD100 blocking activity) do not remove the polypeptide sequence from the definition of anti-CD100 antibodies of interest as used herein.

The art provides substantial guidance regarding the preparation and use of polypeptide variants. In preparing the anti-CD100 binding molecule, e.g., an antibody or antigen-binding fragment thereof, variants, one of skill in the art can readily determine which modifications to the native protein's nucleotide or amino acid sequence will result in a variant that is suitable for use as a therapeutically active component of a pharmaceutical composition used in the methods of the present invention.

The constant region of an anti-CD100 antibody may be mutated to alter effector function in a number of ways. For example, see U.S. Pat. No. 6,737,056B1 and U.S. Patent Application Publication No. 2004/0132101A1, which disclose Fc mutations that optimize antibody binding to Fc receptors.

In certain anti-CD100 antibodies, the Fc portion may be mutated to decrease effector function using techniques known in the art. For example, the deletion or inactivation (through point mutations or other means) of a constant region domain may reduce Fc receptor binding of the circulating modified antibody thereby increasing tumor localization. In other cases it may be that constant region modifications consistent with the instant invention moderate complement binding and thus reduce the serum half life and nonspecific association of a conjugated cytotoxin. Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, such as tumor localization, biodistribution and serum half-life, may easily be measured and quantified using well known immunological techniques without undue experimentation.

Anti-CD100 antibodies of the invention also include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, etc. Additionally, the derivative may contain one or more non-classical amino acids.

A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind an anti-CD100 polypeptide).

For example, it is possible to introduce mutations only in framework regions or only in CDR regions of an antibody molecule. Introduced mutations may be silent or neutral missense mutations, i.e., have no, or little, effect on an antibody's ability to bind antigen. These types of mutations may be useful to optimize codon usage, or improve a hybridoma's antibody production. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein may routinely be expressed and the functional and/or biological activity of the encoded protein, (e.g., ability to immunospecifically bind at least one epitope of a CD100 polypeptide) can be determined using techniques described herein or by routinely modifying techniques known in the art.

In certain embodiments, the anti-CD100 antibodies of the invention comprise at least one optimized complementarity-determining region (CDR). By "optimized CDR" is intended that the CDR has been modified and optimized sequences selected based on the sustained or improved binding affinity and/or anti-CD100 activity that is imparted to an anti-CD100 antibody comprising the optimized CDR. "Anti-CD100 activity" or "CD100 blocking activity" can include activity which modulates one or more of the following activities associated with CD100: B cell activation, aggregation and survival; CD40-induced proliferation and antibody production; antibody response to T cell dependent antigens; T cell or other immune cell proliferation; dendritic cell maturation; demyelination and axonal degeneration; apoptosis of pluripotent neural precursors and/or oligodendrocytes; induction of endothelial cell migration; inhibition of spontaneous monocyte migration; binding to cell surface plexin B1; or any other activity association with soluble CD100 or CD100 that is expressed on the surface of CD100+ cells. Anti-CD100 activity can also be attributed to a decrease in incidence or severity of diseases associated with CD100 expression, including, but not limited to, certain types of lymphomas, autoimmune diseases, inflammatory diseases including central nervous system (CNS) and peripheral nervous system (PNS) inflammatory diseases, transplant rejections, and invasive angiogenesis. Examples of optimized antibodies based on murine anti-CD100 MAbs BD16 and BB18, were described in US Publ. No. 2008/0219971 A1; International Patent Application WO 93/14125 and Herold et al., *Int. Immunol.* 7(1): 1-8 (1995), each of which are herein incorporated by reference in their entirety. The modifications may involve replacement of amino acid residues within the CDR such that an anti-CD100 antibody retains specificity for the CD100 antigen and has improved binding affinity and/or improved anti-CD100 activity.

IV. Polynucleotides Encoding Anti-CD100 Antibodies

The present invention also provides for nucleic acid molecules encoding anti-CD100 antibodies of the invention, or antigen-binding fragments, variants, or derivatives thereof.

In one embodiment, the present invention provides an isolated polynucleotide comprising, consisting essentially of, or consisting of a nucleic acid encoding an immunoglobulin heavy chain variable domain (VH domain), where at least one of the CDRs of the VH domain has an amino acid sequence that is at least about 80%, about 85%, about 90%, about 95%, about 96%, about 97%, about 98%, about 99%, or identical to a polynucleotide sequence selected from the group consisting of SEQ ID NO: 3, SEQ ID NO: 4, or SEQ ID NO: 5.

In other embodiments, the present invention provides an isolated polynucleotide comprising, consisting essentially of, or consisting of a nucleic acid encoding an immunoglobulin NTH domain; where at least one of the CDRs of the VH domain is selected from the group consisting of: (a) a CDR1 comprising the amino acid sequence set forth in SEQ ID NO: 6; (b) a CDR2 comprising the amino acid sequence set forth in SEQ ID NO: 7; and (c) a CDR3 comprising the amino acid sequence set forth in SEQ ID NO: 8.

In a further embodiment, the present invention includes an isolated polynucleotide comprising, consisting essentially of, or consisting of a nucleic acid encoding a VH domain that has an amino acid sequence that is at least about 80%, about 85%, about 90%, about 91%, about 92%, about 93%, about 94%, about 95%, about 96%, about 97%, about 98%, about 99%, or 100% identical to a reference VH domain polypeptide sequence comprising SEQ ID NO: 9 or SEQ ID NO: 10, wherein an anti-CD100 antibody comprising the encoded VH domain specifically or preferentially binds to CD100.

In one embodiment, the present invention provides an isolated polynucleotide comprising, consisting essentially of or consisting of a nucleic acid encoding an immunoglobulin light chain variable domain (VL domain), where at least one of the CDRs of the VL domain has an amino acid sequence that is at least about 80%, about 85%, about 90%, about 95%, about 96%, about 97%, about 98%, about 99%, or identical to a polynucleotide sequence selected from the group consisting of SEQ ID NO: 11, SEQ ID NO: 12, and SEQ ID NO: 13.

In other embodiments, the present invention provides an isolated polynucleotide comprising, consisting essentially of or consisting of a nucleic acid encoding an immunoglobulin VL domain, where at least one of the CDRs of the VL domain is selected from the group consisting of: (a) a CDR1 comprising the amino acid sequence set forth in SEQ ID NO: 14; (b) a CDR2 comprising the amino acid sequence set forth in SEQ ID NO: 15; and (e) a CDR3 comprising the amino acid sequence set forth in SEQ ID NO: 16.

In a further embodiment, the present invention includes an isolated polynucleotide comprising, consisting essentially of, or consisting of a nucleic acid encoding a VL domain that has an amino acid sequence that is at least about 80%, about 85%, about 90%, about 91%, about 92%, about 93%, about 94%, about 95%, about 96%, about 97%, about 98%, about 99%, or 100% identical to a reference VL domain polypeptide sequence comprising SEQ ID NO: 17 or SEQ ID NO: 18, wherein an anti-CD100 antibody comprising the encoded VL domain specifically or preferentially binds to CD100.

Any of the polynucleotides described above may further include additional nucleic acids, encoding, e.g. a signal peptide to direct secretion of the encoded polypeptide, antibody constant regions as described herein, or other heterologous polypeptides as described herein. Also, as described in more detail elsewhere herein, the present invention includes compositions comprising one or more of the polynucleotides described above.

In one embodiment, the invention eludes compositions comprising a first polynucleotide and second polynucleotide wherein said first polynucleotide encodes a VH domain as described herein and wherein said second polynucleotide encodes a VL domain as described herein. Specifically a composition which comprises, consists essentially of, or consists of a VH domain-encoding polynucleotide, as set forth in SEQ ID NO: 19 or SEQ ID NO: 20, and a VL domain-encoding polynucleotide, for example, a polynucleotide encoding the VL domain as set forth in SEQ ID NO: 21 or SEQ ID NO: 22.

The present invention also includes fragments of the polynucleotides of the invention, as described elsewhere. Additionally polynucleotides that encode fusion polypolypeptides, Fab fragments, and other derivatives, as described herein, are also contemplated by the invention.

The polynucleotides may be produced or manufactured by any method known in the art. For example, if the nucleotide sequence of the antibody is known, a polynucleotide encoding the antibody may be assembled from chemically synthesized oligonucleotides (e.g., as described in Kutmeier et al., *Bio Techniques* 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an anti-CD100 antibody, or antigen-binding fragment, variant, or derivative thereof of the invention, may be generated from nucleic acid from a suitable source. If a clone containing a nucleic acid encoding a particular antibody is not available, but the sequence of the antibody molecule is known, a nucleic acid encoding the antibody may be chemically synthesized or obtained from a suitable source (e.g., an antibody cDNA library, or a cDNA library generated from, or nucleic acid, preferably poly A+RNA, isolated from, any tissue or cells expressing the antibody or other anti-CD100 antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody or other anti-CD100 antibody. Amplified nucleic acids generated by PCR may then be cloned into replicable cloning vectors using any method well known in the art.

Once the nucleotide sequence and corresponding amino acid sequence of the anti-CD100 antibody, or antigen-binding fragment, variant, or derivative thereof is determined, its nucleotide sequence may be manipulated using methods well known in the art for the manipulation of nucleotide sequences, e.g., recombinant DNA techniques, site directed mutagenesis, PCR, etc. (see, for example, the techniques described in Sambrook et al. (1990) Molecular Cloning, A Laboratory Manual (2nd ed.; Cold Spring Harbor Laboratory, Cold Spring Harbor, N.Y.) and Ausubel et al., eds. (1998) Current Protocols in Molecular Biology (John Wiley & Sons, NY), which are both incorporated by reference herein in their entireties), to generate antibodies having a different amino acid sequence, for example to create amino acid substitutions, deletions, and/or insertions.

A polynucleotide encoding an anti-CD100 binding molecule, e.g., an antibody, or antigen-binding fragment, variant, or derivative thereof, can be composed of any polyribonucleotide or polydeoxyribonucleotide, which may be unmodified RNA or DNA or modified RNA or DNA. For example, a polynucleotide encoding anti-CD100 antibody, or antigen-binding fragment, variant, or derivative thereof can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, a polynucleotide encoding an anti-CD100 binding molecule, e.g., an antibody, or antigen-binding fragment, variant, or derivative thereof can be composed of triple-stranded regions comprising RNA or DNA or both RNA and DNA. A polynucleotide encoding an anti-CD100 binding molecule, e.g., antibody, or antigen-binding fragment, variant, or derivative thereof, may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

An isolated polynucleotide encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis. Preferably, conservative amino acid substitutions are made at one or more non-essential amino acid residues.

V. Fusion Proteins and Antibody Conjugates

As discussed in more detail elsewhere herein, anti-CD100 binding molecules, e.g., antibodies of the invention, or antigen-binding fragments, variants, or derivatives thereof, may further be recombinantly fused to a heterologous polypeptide at the N- or C-terminus or chemically conjugated (including covalent and non-covalent conjugations) to polypeptides or other compositions. For example, anti-CD100 antibodies may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

Anti-CD100 antibodies of the invention, or antigen-binding fragments, variants, or derivatives thereof, may include derivatives that are modified, i.e., by the covalent attachment of any type of molecule to the antibody such that covalent attachment does not prevent the antibody binding anti-CD100. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, etc. Additionally, the derivative may contain one or more non-classical amino acids.

Anti-CD100 binding molecules, e.g., antibodies of the invention, or antigen-binding fragments, variants, or derivatives thereof, can be composed of amino acids joined to each other by peptide bonds or modified peptide bonds, i.e., peptide isosteres, and may contain amino acids other than the 20 gene-encoded amino acids. For example, anti-CD100 antibodies may be modified by natural processes, such as posttranslational processing, or by chemical modification techniques that are well known in the art. Such modifications are well described in basic texts and in more detailed monographs, as well as in a voluminous research literature. Modifications can occur anywhere in the anti-CD100 binding molecule, including the peptide backbone, the amino acid sidechains and the amino or carboxyl termini, or on moieties such as carbohydrates. It will be appreciated that the same type of modification may be present in the same or varying degrees at several sites in a given anti-CD100 binding molecule. Also, a given anti-CD100 binding molecule may contain many types of modifications. Anti-CD100 binding molecules may be branched, for example, as a result of ubiquitination, and they may be cyclic, with or without branching. Cyclic, branched, and branched cyclic anti-CD100 binding molecule may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination, (See, for instance, Proteins—Structure and Molecular Properties, T. E. Creighton, W. H. Freeman and Company, NY; 2nd ed. (1993): Johnson, ed. (1983) Posttranslational Covalent Modification of Proteins (Academic Press, NY), pgs. 1-12; Seifter et al., *Meth. Enzymol.* 182:626-646 (1990); Rattan et al., *Ann. NY Acad. Sci.* 663:48-62 (1992)).

The present invention also provides for fusion proteins comprising an anti-CD100 antibody, or antigen-binding fragment, variant, or derivative thereof, and a heterologous polypeptide. The heterologous polypeptide to which the antibody is fused may be useful for function or is useful to target the anti-CD100 polypeptide expressing cells.

In one embodiment, a fusion protein of the invention comprises, consists essentially of, or consists of, a polypeptide having the amino acid sequence of any one or more of the VH domains of an antibody of the invention or the amino acid sequence of any one or more of the VL, domains of an antibody of the invention or fragments or variants thereof, and a heterologous polypeptide sequence.

In another embodiment, a fusion protein for use in the diagnostic and treatment methods disclosed herein comprises, consists essentially of, or consists of a polypeptide having the amino acid sequence of any one, two, three of the CDRs of the VH domain of an anti-CD100 antibody, or fragments, variants, or derivatives thereof, or the amino acid sequence of any one, two, three of the CDRs of the VL domain an anti-CD100 antibody, or fragments, variants, or derivatives thereof, and a heterologous polypeptide sequence. In one embodiment, a fusion protein comprises a polypeptide having the amino acid sequence of at least one VH domain of an anti-CD100 antibody of the invention and the amino acid sequence of at least one VL domain of an anti-CD100 antibody of the invention or fragments, derivatives or variants thereof, and a heterologous polypeptide sequence. Preferably, the VH and VL domains of the fusion protein correspond to a single source antibody (or scFv or Fab fragment) that specifically binds at least one epitope of CD100. In yet another embodiment, a fusion protein for use in the diagnostic and treatment methods disclosed herein comprises a polypeptide having the amino acid sequence of any one, two, three or more of the CDRs of the VH domain of an anti-CD100 antibody and the amino acid sequence of any one, two, three or more of the CDRs of the VL domain of an anti-CD100 antibody, or fragments or variants thereof, and a heterologous polypeptide sequence. Preferably, two, three, four, five, six, or more of the CDR(s) of the VH domain or VL domain correspond to single source antibody (or say or Fab fragment) of the invention. Nucleic acid molecules encoding these fusion proteins are also encompassed by the invention.

Exemplary fusion proteins reported in the literature include fusions of the T cell receptor (Gaseoigne et al., *Proc. Natl. Acad. Sci. USA* 84:2936-2940 (1987)); CD4 (Capon et al., *Nature* 337:525-531 (1989); Traunecker et al., *Nature* 339:68-70 (1989); Zettmeissl et al., *DNA Cell Biol. USA* 9:347-353 (1990); and Byrn et al., *Nature* 344:667-670 (1990)); L-selectin (homing receptor) (Watson et al., *J. Cell. Biol.* 110:2221-2229 (1990); and Watson et al., *Nature* 349:164-167 (1991)); CD44 (Aruffo et al., *Cell* 61:1303-1313 (1990)); CD28 and 137 (Linsley et al., *J. Exp. Med.* 173:721-730 (1991)); CTLA-4 (Lisley et al., *J. Exp. Med.* 174:561-569 (1991)); CD22 (Stamenkovie et al., *Cell* 66:1133-1144 (1991)); TNF receptor (Ashkenazi et al., *Proc. Natl. Acad. Sci. USA* 88:10535-10539 (1991); Lesslauer et al., *Eur. J. Immunol.* 27:2883-2886 (1991); and Peppel et al., *J. Exp. Med.* 174:1483-1489 (1991)); and IgE receptor a (Ridgway and Gorman, J. Cell. Biol. Vol. 115, Abstract No. 1448 (1991)).

As discussed elsewhere herein, anti-CD100 binding molecules, e.g., antibodies of the invention, or antigen-binding fragments, variants, or derivatives thereof, may be fused heterologous polypeptides to increase the in vivo half life of the polypeptides or for use in immunoassays using methods known in the art. For example, in one embodiment, PEG can be conjugated to the anti-CD100 antibodies of the invention to increase their half-life in vivo. See Leong et al., *Cytokine* 16:106 (2001); Adv. in Drug Deliv. Rev. 54:531 (2002); or Weir et al., *Biochem. Soc. Transactions* 30:512 (2002).

Moreover, anti-CD100 binding molecules, e.g., antibodies of the invention, or antigen-binding fragments, variants, or derivatives thereof, can be fused to marker sequences, such as a peptide to facilitate their purification or detection. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., *Cell* 37:767 (1984)) and the "flag" tag.

Fusion proteins can be prepared using methods that are well known in the art (see for example U.S. Pat. Nos. 5,116,964 and 5,225,538). The precise site at which the fusion is made may be selected empirically to optimize the secretion or binding characteristics of the fusion protein. DNA encoding the fusion protein is then transfected into a host cell for expression.

Anti-CD100 binding molecules, e.g., antibodies of the present invention, or antigen-binding fragments, variants, or derivatives thereof, may be used in non-conjugated form or may be conjugated to at least one of a variety of molecules, e.g., to improve the therapeutic properties of the molecule, to facilitate target detection, or for imaging or therapy of the patient. Anti-CD100 binding molecules, e.g., antibodies of the invention, or antigen-binding fragments, variants, or derivatives thereof, can be labeled or conjugated either before or after purification, or when purification is performed.

In particular, anti-CD100 antibodies of the invention, or antigen-binding fragments, variants, or derivatives thereof, may be conjugated to therapeutic agents, prodrugs, peptides, proteins, enzymes, viruses, lipids, biological response modifiers, pharmaceutical agents, or PEG.

Those skilled in the art will appreciate that conjugates may also be assembled using a variety of techniques depending on the selected agent to be conjugated. For example, conjugates with biotin are prepared, e.g., by reacting a binding polypeptide with an activated ester of biotin such as the biotin N-hydroxysuccinimide ester. Similarly, conjugates with a fluorescent marker may be prepared in the presence of a coupling agent, e.g., those listed herein, or by reaction with an isothiocyanate, preferably fluorescein-isothiocyanate. Conjugates of the anti-CD100 antibodies of the invention, or antigen-binding fragments, variants, or derivatives thereof, are prepared in an analogous manner.

The present invention further encompasses anti-CD100 binding molecules, e.g., antibodies of the invention, or antigen-binding fragments, variants, or derivatives thereof, conjugated to a diagnostic or therapeutic agent. The anti-CD100 antibodies, including antigen-binding fragments, variants, and derivatives thereof, can be used diagnostically to, for example, monitor the development or progression of a disease as part of a clinical testing procedure to, e.g., determine the efficacy of a given treatment and/or prevention regimen. For example, detection can be facilitated by coupling the anti-CD100 antibody, or antigen-binding fragment, variant, or derivative thereof, to a detectable substance. Examples of detectable substances include various enzymes, prosthetic groups, fluorescent materials, luminescent materials, bioluminescent materials, radioactive materials, positron emitting metals using various positron emission topographies, and nonradioactive paramagnetic metal ions. Sec, for example, U.S. Pat. No. 4,741,900 for metal ions which can be conjugated to antibodies for use as diagnostics according to the present invention. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In, $^{90}$Y, or $^{99}$Tc.

An anti-CD100 binding molecule, e.g., an antibody, or antigen-binding fragment, variant, or derivative thereof, may be conjugated to a therapeutic moiety such as a cytotoxin, a therapeutic agent or a radioactive metal ion. A cytotoxin or cytotoxic agent includes any agent that is detrimental to cells.

An anti-CD100 binding molecule, e.g., an antibody, or antigen-binding fragment, variant, or derivative thereof, also can be detectably labeled by coupling it to a chemiluminescent compound. The presence of the chemiluminescent-tagged anti-CD100 binding molecule is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

One of the ways in which an anti-CD100 antibody, or antigen-binding fragment, variant, or derivative thereof, can be detectably labeled is by linking the same to an enzyme and using the linked product in an enzyme immunoassay (EIA) (Volley, A., "The Enzyme Linked Immunosorbent Assay (ELISA)" Microbiological Associates Quarterly Publication, Walkersville, Md.; Diagnostic Horizons 2:1-7 (1978); Voller et al., *J. Clin. Pathol.* 31:507-520 (1978); Butler, *Meth. Enzymol.* 73:482-523 (1981); Maggio, ed. (1980) Enzyme Immunoassay, CRC Press, Boca Raton, Fla.; Ishikawa et al., eds. (1981) Enzyme Immunoassay (Kgaku Shoin, Tokyo). The enzyme, which is bound to the anti-CD100 antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the anti-CD100 binding molecule, e.g., antibody, or antigen-binding fragment, variant, or derivative thereof, it is possible to detect the binding molecule through the use of a radioimmunoassay (RIA) (see, for example, Weintraub (March, 1986) Principles of Radioimmunoassays, Seventh Training Course on Radioligand Assay Techniques (The Endocrine Society), which is incorporated by reference herein). The radioactive isotope can be detected by means including, but not limited to, a gamma counter, a scintillation counter, or autoradiography.

An anti-CD100 binding molecule, e.g., antibody, or antigen-binding fragment, variant, or derivative thereof, can also be detectably labeled using fluorescence emitting metals such as $152Eu$, or others of the lanthanide series. These metals can be attached to the binding molecule using such metal chelating groups as diethylenetriaminepentacetic acid (DTPA) or ethylenediaminetetraacetic acid (EDTA).

Techniques for conjugating various moieties to an antibody (e.g., an anti-CD100 antibody), or antigen-binding fragment, variant, or derivative thereof, are well known, see, e.g., Amon et al. (1985) "Monoclonal Antibodies for Immunotargeting of Drugs in Cancer Therapy," in Monoclonal Antibodies and Cancer Therapy, ed. Reisfeld et al. (Alan R. Liss, Inc.), pp. 243-56; Hellstrom et al. (1987) "Antibodies for Drug Delivery," in Controlled Drug Delivery, ed. Robinson et al, (2nd ed.; Marcel Dekker, Inc.), pp. 623-53); Thorpe (1985) "Antibody Carriers of Cytotoxic Agents in Cancer Therapy: A Review," in Monoclonal Antibodies '84: Biological and Clinical Applications, ed. Pinchera et al., pp. 475-506; "Analysis, Results, and Future Prospective of the Therapeutic Use of Radiolabeled Antibody in Cancer Therapy," in Monoclonal Antibodies for Cancer Detection and Therapy, ed. Baldwin et al., Academic Press, pp. 303-16 (1985); and Thorpe et al. (1982) "The Preparation and Cytotoxic Properties of Antibody-Toxin Conjug" Immunol. Rev. 62:119-58.

VI. Expression of Antibody Polypeptides

DNA sequences that encode the light and the heavy chains of the antibody may be made, either simultaneously or separately, using reverse transcriptase and DNA polymerase in accordance with well known methods. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes.

DNA, typically plasmid DNA, may be isolated Mom the cells using techniques known in the aft, restriction mapped and sequenced in accordance with standard, well known techniques set forth in detail, e.g., in the foregoing references relating to recombinant DNA techniques. Of course, the DNA may be synthetic according to the present invention at any point during the isolation process or subsequent analysis.

Following manipulation of the isolated genetic material to provide anti-CD100 antibodies, or antigen-binding fragments, variants, or derivatives thereof, of the invention, the polynucleotides encoding the anti-CD100 antibodies are typically inserted in an expression vector for introduction into host cells that may be used to produce the desired quantity of anti-CD100 antibody.

Recombinant expression of an antibody, or fragment, derivative or analog thereof, e.g., a heavy or light chain of an antibody that binds to a target molecule described herein, e.g., CD100, requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods that are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The term "vector" or "expression vector" is used herein to mean vectors used in accordance with the present invention as a vehicle for introducing into and expressing a desired gene in a host cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

For the purposes of this invention, numerous expression vector systems may be employed. For example, one class of vector utilizes DNA elements that are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites.

Additionally, cells that have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. Additional elements may also be needed for optimal synthesis of mRNA. These elements may include signal sequences, splice signals, as well as transcriptional promoters, enhancers, and termination signals.

In particularly preferred embodiments the cloned variable region genes are inserted into an expression vector along with the heavy and light chain constant region genes (preferably human) synthesized as discussed above. Of course, any expression vector that is capable of eliciting expression in eukaryotic cells may be used in the present invention. Examples of suitable vectors include, but are not limited to plasmids pcDNA3, pHCMV/Zeo, pCR3.1, pEF 1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.). In general, screening large numbers of transformed cells for those that express suitably high levels if immunoglobulin heavy and light chains is routine experimentation that can be carried out, for example, by robotic systems.

More generally, once the vector or DNA sequence encoding a monomeric subunit of the anti-CD100 antibody has been prepared, the expression vector may be introduced into an appropriate host cell. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway (1988) "Mammalian Expression Vectors" in Vectors, ed. Rodriguez and Denhardt (Butterworths, Boston, Mass.), Chapter 24.2, pp. 470-472. Typically, plasmid introduction into the host is via electroporation. The host cells harboring the expression construct are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

The expression vector is transferred to a host cell by conventional techniques, and the transfected cells are then cultured by conventional techniques to produce an antibody for use in the methods described herein. Thus, the invention includes host cells containing a polynucleotide encoding an antibody of the invention, or a heavy or light chain thereof, operably linked to a heterologous promoter. In preferred embodiments for the expression of double-chained antibodies, vectors encoding both the heavy and light chains may be co-expressed in the host cell for expression of the entire immunoglobulin molecule, as detailed below.

As used herein, "host cells" refers to cells that harbor vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

A variety of host-expression vector systems may be utilized to express antibody molecules for use in the methods described herein. Such host-expression systems represent vehicles by which the coding sequences of interest may be produced and subsequently purified, but also represent cells that may, when transformed or transfected with the appropriate nucleotide coding sequences, express an antibody molecule of the invention in situ. These include, but are not limited to, microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., *Gene* 45:101 (1986); Cockett et al., *Bio/Technology* 8:2 (1990)).

The host cell line used for protein expression is often of mammalian origin; those skilled in the art are credited with ability to preferentially determine particular host cell lines that are best suited for the desired gene product to be expressed therein. Exemplary host cell lines include, but are not limited to, CHO (Chinese Hamster Ovary), DG44 and DUXB11 (Chinese Hamster Ovary lines, DHFR minus), HELA (human cervical carcinoma), CVI (monkey kidney line), COS (a derivative of CVI with SV40 T antigen), VERY, BHK (baby hamster kidney), MDCK, 293, WI38, R1610 (Chinese hamster fibroblast) BALBC/3T3 (mouse fibroblast), HAK (hamster kidney line), SP2/O (mouse myeloma), P3.times.63-Ag3.653 (mouse myeloma), BFA-1c1BPT (bovine endothelial cells), RAJI (human lymphocyte) and 293 (human kidney). Host cell lines are typically available from commercial services, the American Tissue Culture Collection or from published literature.

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used.

For long-term, high-yield production of recombinant proteins, stable expression is preferred. For example, cell lines that stably express the antibody molecule may be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which stably express the antibody molecule.

A number of selection systems may be used, including, but not limited to, the herpes simplex virus thymidine kinase (Wigler et al., *Cell* 11:223 (1977)), hypoxanthine-guanine phosphoribosyltransferase (Szybalska and Szybalski, *Proc. Natl. Acad. Sci. USA* 48:202 (1992)), and adenine phosphoribosyltransferase (Lowy et al., *Cell* 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., *Natl. Acad. Sci. USA* 77:357 (1980); O'Hare et al., *Proc. Natl. Acad. Sci. USA* 78:1527 (1981)); gpt, which confers resistance to mycophenolic acid (Mulligan and Berg, *Proc. Natl. Acad. Sci. USA* 78:2072 (1981)); neo, which confers resistance to the aminoglycoside G-418 Clinical Pharmacy 12:488-505; Wu and Wu, *Biotherapy* 3:87-95 (1991); Tolstoshey, *Ann. Rev. Pharmacol. Toxicol.* 32:573-596 (1993); Mulligan, *Science* 260:926-932 (1993); and Morgan and Anderson, *Ann. Rev. Biochem.* 62:191-217 (1993); TIB TECH 11(5):155-215 (May, 1993); and hygro, which confers resistance to hygromycin (Santerre et al., *Gene* 30:147 (1984). Methods commonly known in the art of recombinant DNA technology which can be used are described in Ausubel et al. (1993) Current Protocols in Molecular Biology (John Wiley & Sons, NY); Kriegier (1990) "Gene Transfer and Expression" in A Laboratory Manual (Stockton Press, NY); Dracopoli et al. (eds) (1994) Current Protocols in Human Genetics (John Wiley & Sons, NY) Chapters 12 and 13; Colberre-Garapin et al. (1981) J. Mol. Biol. 150:1, which are incorporated by reference herein in their entireties.

The expression levels of an antibody molecule can be increased by vector amplification (for a review, see Bebbington and Hentschel (1987) "The Use of Vectors Based on Gene Amplification for the Expression of Cloned Genes in Mammalian Cells in DNA Cloning" (Academic Press, NY) Vol. 3. When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.* 3:257 (1983)).

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g., after preferential biosynthesis of a synthetic hinge region polypeptide or prior to or subsequent to the HIC chromatography step described herein.

Genes encoding anti-CD100 antibodies, or antigen-binding fragments, variants, or derivatives thereof of the invention can also be expressed in non-mammalian cells such as insect, bacteria or yeast or plant cells. Bacteria that readily take up nucleic acids include members of the enterobacteriaceae, such as strains of *Escherichia coli* or *Salmonella*; Bacillaceae, such as *Bacillus subtilis*; Pneumococcus; *Streptococcus*, and *Haemophilus influenzae*. It will further be appreciated that, when expressed in bacteria, the heterologous polypeptides typically become part of inclusion bodies. The heterologous polypeptides must be isolated, purified and then assembled into functional molecules. Where tetravalent forms of antibodies are desired, the subunits will then self-assemble into tetravalent antibodies (WO 02/096948A2).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., *EMBO J.* 2:1791 (1983)), in which the antibody coding sequence may be ligated individually into the vector in frame with the lacZ coding region so that a fusion protein is produced; ON vectors (Inouye and Inouye, *Nucleic Acids Res.* 13:3101-3109 (1985); Van Heeke and Schuster, *J. Biol. Chem.* 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In addition to prokaryotes, eukaryotic microbes may also be used. *Saccharomyces cerevisiae*, or common baker's yeast, is the most commonly used among eukaryotic microorganisms although a number of other strains are commonly available, e.g., *Pichia pastoris*.

For expression in *Saccharomyces*, the plasmid YRp7, for example, (Stinchcomb et al., *Nature* 282:39 (1979); Kingsman et al., *Gene* 7:141 (1979); Tschemper et al., *Gene* 10:157 (1980)) is commonly used. This plasmid already contains the TRP1 gene, which provides a selection marker for a mutant strain of yeast lacking the ability to grow in tryptophan, for example ATCC No. 44076 or PEP4-1 (Jones, *Genetics* 85:12 (1977)). The presence of the trp1 lesion as a characteristic of the yeast host cell genome then provides an effective environment for detecting transformation by growth in the absence of tryptophan.

In an insect system, *Autographa californica* nuclear polyhedrosis virus (AcNPV) is typically used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

Once an antibody molecule of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Alternatively, a preferred method for increasing the affinity of antibodies of the invention is disclosed in U.S. Patent Application Publication No. 2002 0123057 A1.

VII. Treatment Methods Using Therapeutic Anti-CD100 Antibodies

Methods of the invention are directed to the use of anti-CD100 binding molecules, e.g., antibodies, including antigen-binding fragments, variants, and derivatives thereof, to treat patients having a disease associated with soluble CD100 secreted from or expressed on CD100-expressing cells. By "CD100-expressing cell" is intended normal and malignant cells expressing CD100 antigen. Methods for detecting CD100 expression in cells are well known in the art and include, but are not limited to, PCR techniques, immunohistochemistry, flow cytometry, Western blot, ELISA, and the like.

Though the following discussion refers to diagnostic methods and treatment of various diseases and disorders with an anti-CD100 antibody of the invention, the methods described herein are also applicable to the antigen-binding fragments, variants, and derivatives of these anti-CD100 antibodies that retain the desired properties of the anti-CD100 antibodies of the invention, e.g., capable of specifically binding CD100, e.g., human, mouse, or human and mouse CD100, and having CD100 neutralizing activity.

In one embodiment, treatment includes the application or administration of an anti-CD100 binding molecule, e.g., an antibody or antigen binding fragment thereof, of the current invention to a patient, or application or administration of the anti-CD100 binding molecule to an isolated tissue or cell line from a patient, where the patient has a disease, a symptom of a disease, or a predisposition toward a disease. In another embodiment, treatment is also intended to include the application or administration of a pharmaceutical composition comprising the anti-CD100 binding molecule, e.g., an antibody or antigen binding fragment thereof, of the current invention to a patient, or application or administration of a pharmaceutical composition comprising the anti-CD100 binding molecule to an isolated tissue or cell line from a patient, who has a disease, a symptom of a disease, or a predisposition toward a disease.

The anti-CD100 binding molecules, e.g., antibodies or binding fragments thereof, of the present invention are useful for the treatment of various malignant and non-malignant tumors. By "anti-tumor activity" is intended a reduction in the rate of malignant CD100-expressing cell proliferation or accumulation, and hence a decline in growth rate of an existing tumor or in a tumor that arises during therapy, and/or destruction of existing neoplastic (tumor) cells or newly formed neoplastic cells, and hence a decrease in the overall size of a tumor during therapy. For example, therapy with at least one anti-CD100 antibody causes a physiological response, for example, a reduction in angiogenesis, that is beneficial with respect to treatment of disease states associated with CD100-expressing cells in a human.

In one embodiment, the invention relates to anti-CD100 binding molecules, e.g., antibodies or binding fragments thereof, according to the present invention for use as a medicament, in particular for use in the treatment or prophylaxis of cancer or for use in a precancerous condition or lesion. In certain embodiments, an anti-CD100 binding molecule, e.g., an antibody or binding fragment thereof, of the invention is used for the treatment of a CD100 over-expressing cancer. In certain embodiments, an anti-CD100 binding molecule, e.g., an antibody or binding fragment thereof, of the invention is used for the treatment of a CD100 over-expressing head and neck or colon cancer.

Further, anti-CD100 binding molecules, e.g., antibodies or binding fragments thereof, of the present invention can also be used to inhibit angiogenesis for the treatment of pathological conditions dependent upon the formation of new blood vessels, including tumor development and macular degeneration. Angiogenesis is a complex multistep morphogenetic event during which endothelial cells, stimulated by major determinants of vascular remodeling, dynamically modify their cell-to-cell and cell-to-matrix contacts and move directionally to be reorganized into a mature vascular tree (Bussolino et al., *Trends Biochem Sci.* 22:251-256 (1997); Risau, *Nature* 386:671-674 (1997); Jain, *Nat. Med.* 9:685-693 (2003)). The formation of new blood vessels is a key step during embryo development, but it also occurs in adults in physiologic and in pathologic conditions, such as retinopathy, rheumatoid arthritis, ischemia, and particularly tumor growth and metastasis (Carmeliet, *Nat. Med.* 9:653-660 (2003)). This pathological formation of new blood vessels is herein referred to as "invasive angiogenesis." Basile et al., *PNAS* 103(24): 9017-9022 (2006)) demonstrated that, when shed from HNSCC cells, CD100 stimulates endothelial cell migration, which was prevented by CD100-blocking antibodies and by CD100 knockdown. CD100 overexpression was also noted in prostate, colon, breast, and lung cancers, suggesting that expression of CD100 is a frequently used strategy by which a wide variety of carcinomas may promote angiogenesis.

In accordance with the methods of the present invention, at least one anti-CD100 binding molecule, e.g., an antibody or antigen binding fragment thereof, as defined elsewhere herein is used to promote a positive therapeutic response with respect to a malignant human cell. By "positive therapeutic response" with respect to cancer treatment is intended an improvement in the disease in association with the anti-tumor activity of these binding molecules, e.g., antibodies or fragments thereof, and/or an improvement in the symptoms associated with the disease. That is, an anti-proliferative effect, the prevention of further tumor outgrowths, a reduction in tumor size, a decrease in tumor vasculature, a reduction in the number of cancer cells, and/or a decrease in one or more symptoms associated with the disease can be observed. Thus, for example, an improvement in the disease may be characterized as a complete response. By "complete response" is intended an absence of clinically detectable disease with normalization of any previously abnormal radiographic studies, bone marrow, and cerebrospinal fluid (CSF). Such a response must persist for at least one month following treatment according to the methods of the invention. Alternatively, an improvement in the disease may be categorized as being a partial response. By "partial response" is intended at least about a 50% decrease in all measurable tumor burden (i.e., the number of tumor cells present in the subject) in the absence of new lesions and persisting for at least one month. Such a response is applicable to measurable tumors only.

Tumor response can be assessed for changes in tumor morphology (i.e., overall tumor burden, tumor cell count, and the like) using screening techniques such as bioluminescent imaging, for example, luciferase imaging, bone scan imaging, and tumor biopsy sampling including bone marrow aspiration (BMA). In addition to these positive therapeutic responses, the subject undergoing therapy with the anti-CD100 binding molecule, e.g., an antibody or antigen-binding fragment thereof, may experience the beneficial effect of an improvement in the symptoms associated with the disease. For example, the subject may experience a decrease in the so-called B symptoms, e.g., night sweats, fever, weight loss, and/or urticaria.

The anti-CD100 binding molecules, e.g., antibodies or antigen binding fragments thereof, described herein may also find use in the treatment of inflammatory diseases and deficiencies or disorders of the immune system that are associated with CD100 expressing cells. Inflammatory diseases are characterized by inflammation and tissue destruction, or a combination thereof. By "anti-inflammatory activity" is intended a reduction or prevention of inflammation. "Inflammatory disease" includes any inflammatory immune-mediated process where the initiating event or target of the immune response involves non-self antigen(s), including, for example, alloantigens, xenoantigens, viral antigens, bacterial antigens, unknown antigens, or allergens. In one embodiment, the inflammatory disease is an inflammatory disorder of the peripheral or central nervous system. In another embodiment, the inflammatory disease is an inflammatory disorder of the joints.

Further, for purposes of the present invention, the term "inflammatory disease(s)" includes "autoimmune disease(s)." As used herein, the term "autoimmunity" is generally understood to encompass inflammatory immune-mediated processes involving "self" antigens. In autoimmune diseases, self antigen(s) trigger host immune responses. An autoimmune disease can result from an inappropriate immune response directed against a self antigen (an autoantigen), which is a deviation from the normal state of self-tolerance.

In general, antibodies (particularly, but not exclusively, IgG antibodies), acting as cytotoxic molecules or as immune complexes, are the principal mediators of various autoimmune diseases, many of which can be debilitating or life-threatening.

In one embodiment, the anti-CD100 binding molecule, e.g., an antibody or antigen binding fragment, of the invention is used to treat multiple sclerosis (MS). MS, also known as disseminated sclerosis or encephalomyelitis disseminata, is an autoimmune condition in which the immune system attacks the central nervous system, leading to demyelination. The name multiple sclerosis refers to the scars (scleroses, also referred to as plaques or lesions) that form in the nervous system. MS lesions commonly involve white matter areas close to the ventricles of the cerebellum, brain stem, basal ganglia and spinal cord, and the optic nerve. MS results in destruction of oligodendrocytes, the cells responsible for creating and maintaining the myelin sheath. MS results in a thinning or complete loss of myelin and, as the disease advances, transection of axons.

Neurological symptom can vary with MS, and the disease often progresses to physical and cognitive disability, MS takes several forms, with new symptoms occurring either in discrete attacks (relapsing forms) or slowly accumulating over time (progressive forms). Between attacks, symptoms may go away completely, but permanent neurological damage often results, especially as the disease advances.

Neutralization of CD100 using an anti-CD100 monoclonal antibody of the invention, e.g., MAb 2503, MAb 67 or MAb 76, may be used to reduce the severity of MS through several different mechanisms, e.g., anti-CD100 monoclonal antibodies may, block immune maturation and activation by CD100 to reduce the rate of relapse by reducing secondary immune responses to CNS antigens, and anti-CD100 monoclonal antibodies may block the effect of soluble CD100 in mediating apoptosis of oligodendrocytes in the CNS may reduce disease severity by reducing demyelination.

In one embodiment, the anti-CD100 binding molecule, e.g., an antibody or antigen binding fragment, of the invention is used to treat arthritis. Arthritis, is an inflammatory disease of the joints, which can be caused by an autoimmune condition in which the immune system attacks the joints. In certain embodiments, the arthritis is selected from the group consisting of osteoarthritis, gouty arthritis, ankylosing spondylitis, psoriatic arthritis, reactive arthritis, rheumatoid arthritis, juvenile onset rheumatoid arthritis, infectious arthritis, inflammatory arthritis, septic arthritic, degenerative arthritis, arthritis mutilans, and lyme arthritis. In one embodiment, the arthritis is rheumatoid arthritis (RA).

The present invention includes methods of treating or preventing arthritis by administering to a subject an anti-CD100 binding molecule of the invention, MAb 2503, MAb 67 or MAb 76. Methods of the present invention may reduce the pain, swelling, or stiffness associated with arthritis, e.g., rheumatoid arthritis. The present invention is also directed to methods for improving joint performance, function, and health. In some embodiments of the present invention, treatment results in a decrease in arthritis severity scores, a decrease in arthritis severity/area under curve, a decrease in histopathology parameters associated with arthritis (inflammation, pannus, cartilage damage, and bone damage), a decrease in serum arachidonic acid levels, or a decrease in anti-collagen antibodies. In certain embodiments, beneficial or desired clinical results include, but are not limited to, alleviation of symptoms associated with arthritis; prevention of arthritis; delay in the onset of arthritis; reduced incidence of arthritis in a population; diminishment of the extent of the condition associated with arthritis; stabilization (i.e., not worsening) of the state of the condition, disorder or disease associated with arthritis; delay in onset or slowing of the condition, disorder or disease progression associated with arthritis; amelioration of the condition, disorder or disease state, remission (whether partial or total) of the condition, disorder or disease associated with arthritis, whether detectable or undetectable; or enhancement or improvement of the condition, disorder or disease associated with arthritis.

The method of the present invention can be administered to individuals who have arthritis or individuals who are at risk for developing arthritis. Thus, in some embodiments the invention is directed to a method of treating a subject having normal joints, borderline arthritic joints, or very arthritic joints, the method comprising administering an anti-CD100 binding molecule of the invention, e.g., MAb 2503, MAb 67 or MAb 76, to a subject as described herein. In some embodiments, the method of the present invention can be used to treat chronic arthritis for the remainder of the life of the subject.

In accordance with the methods of the present invention, at least one anti-CD100 binding molecule, e.g., an antibody or antigen binding fragment thereof, as defined elsewhere herein is used to promote a positive therapeutic response with respect to treatment or prevention of an autoimmune disease and/or inflammatory disease. By "positive therapeutic response" with respect to an autoimmune disease and/or inflammatory disease is intended an improvement in the disease in association with the anti-inflammatory activity, anti-angiogenic activity, anti-apoptotic activity, or the like, of these antibodies, and/or an improvement in the symptoms associated with the disease. That is, an anti-proliferative effect, the prevention of further proliferation of the CD100-expressing cell, a reduction in the inflammatory response including but not limited to reduced secretion of inflammatory cytokines, adhesion molecules, proteases, immunoglobulins (in instances where the CD100 bearing cell is a B cell), combinations thereof, and the like, increased production of anti-inflammatory proteins, a reduction in the number of autoreactive cells, an increase in immune tolerance, inhibition of autoreactive cell survival, reduction in apoptosis, reduction in endothelial cell migration, increase in spontaneous monocyte migration, reduction in and/or a decrease in one or more symptoms mediated by stimulation of sCD100 or CD100-expressing cells can be observed. Such positive therapeutic responses are not limited to the route of administration and may comprise administration to the donor, the donor tissue (such as for example organ perfusion), the host, any combination thereof, and the like.

Clinical response can be assessed using screening techniques such as magnetic resonance imaging (MRI) scan, x-radiographic imaging, computed tomographic (CT) scan, flow cytometry or fluorescence-activated cell sorter (FACS) analysis, histology, gross pathology, and blood chemistry, including but not limited to changes detectable by ELISA, RIA, chromatography, and the like. In addition to these positive therapeutic responses, the subject undergoing therapy with the anti-CD100 binding molecule, e.g., an antibody or antigen-binding fragment thereof, may experience the beneficial effect of an improvement in the symptoms associated with the disease.

The anti-CD100 binding molecules, e.g., antibodies or antigen binding fragments thereof, can be used in combination with at least one other cancer therapy, including, but not limited to, surgery or surgical procedures (e.g. splenectomy, hepatectomy, lymphadenectomy, leukophoresis, bone marrow transplantation, and the like); radiation therapy; chemotherapy, optionally in combination with autologous bone marrow transplant, or other cancer therapy; where the additional cancer therapy is administered prior to, during, or subsequent to the anti-CD100 binding molecule, e.g., antibody or antigen binding fragment thereof, therapy. Thus, where the combined therapies comprise administration of an anti-CD100 binding molecule, e.g., an antibody or antigen binding fragment thereof, of the invention in combination with administration of another therapeutic agent, as with chemotherapy, radiation therapy, other anti-cancer antibody therapy, small molecule-based cancer therapy, or vaccine/immunotherapy-based cancer therapy, the methods of the invention encompass coadministration, using separate formulations or a single pharmaceutical formulation, or and consecutive administration in either order.

The anti-CD100 binding molecules, e.g., antibodies or binding fragments thereof, of the invention can be used in combination with any known therapies for autoimmune and inflammatory diseases, including any agent or combination of agents that are known to be useful, or which have been used or are currently in use, for treatment of autoimmune and inflammatory diseases. Thus, where the combined therapies comprise administration of an anti-CD100 binding molecules in combination with administration of another therapeutic agent, the methods of the invention encompass coadministration, using separate formulations or a single pharmaceutical formulation, and consecutive administration in either order. In some embodiments of the invention, the anti-CD100 antibodies described herein are administered in combination with immunosuppressive drugs or anti-inflammatory drugs, wherein the antibody and the therapeutic agent(s) may be administered sequentially, in either order, or simultaneously (i.e., concurrently or within the same time frame).

In some other embodiments, the anti-CD100 binding molecules, e.g., antibodies or antigen binding fragments thereof, of the invention may be used alone or in combination with immunosuppressive drugs to treat and/or prevent rheumatoid arthritis. Thus, in some embodiments where the anti-CD100 antibodies of the invention are used to treat rheumatoid arthritis, the antibodies may used in combination with suitable immunosuppressive drugs. As discussed above, treatment effectiveness may be assessed using any means and includes, but is not limited to, effectiveness as measured by clinical responses defined by the American College of Rheumatology criteria, the European League of Rheumatism criteria, or any other criteria. See for example, Felson et al., *Arthritis. Rheum.* 38:727-35 (1995) and van Gestel et al., *Arthritis Rheum.* 39:34-40 (1996).

In yet other embodiments, the anti-CD100 antibodies of the invention may be used alone or in combination with immunosuppressive drugs to treat and/or prevent multiple sclerosis. Thus in some embodiments where the anti-CD100 antibodies of the invention are used to treat multiple sclerosis, the antibodies may used in combination with suitable immunosuppressive drugs.

A further embodiment of the invention is the use of anti-CD100 binding molecule, e.g., antibodies or antigen binding fragments thereof, for diagnostic monitoring of protein levels in tissue as part of a clinical testing procedure, e.g., to determine the efficacy of a given treatment regimen. For example, detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{35}$S, or $^{3}$H.

VIII. Pharmaceutical Compositions and Administration Methods

Methods of preparing and administering the anti-CD100 binding molecule, e.g., antibodies, or antigen-binding fragments, variants, or derivatives thereof, of the invention to a subject in need thereof are well known to or are readily determined by those skilled in the art. The route of administration of the anti-CD100 binding molecule, e.g, antibody, or antigen-binding fragment, variant, or derivative thereof, may be, for example, oral, parenteral, by inhalation or topical. The term parenteral as used herein includes, e.g., intravenous, intraarterial, intraperitoneal, intramuscular, subcutaneous, rectal, or vaginal administration. While all these forms of administration are clearly contemplated as being within the scope of the invention, an example of a form for administration would be a solution for injection, in particular for intravenous or intraarterial injection or drip. Usually, a suitable pharmaceutical composition for injection may comprise a buffer (e.g. acetate, phosphate or citrate buffer), a surfactant (e.g. polysorbate), optionally a stabilizer agent (e.g. human albumin), etc. However, in other methods compatible with the teachings herein, anti-CD100 binding molecules, e.g., antibodies, or antigen-binding fragments, variants, or derivatives thereof of the invention can be delivered directly to the site of the adverse cellular population thereby increasing the exposure of the diseased tissue to the therapeutic agent.

As discussed herein, anti-CD100 binding molecules, e.g., antibodies, or antigen-binding fragments, variants, or derivatives thereof of the invention may be administered in a pharmaceutically effective amount for the in vivo treatment of CD100-expressing cell-mediated diseases such as certain types of cancers, autoimmune diseases, inflammatory diseases including central nervous system (CNS) and peripheral nervous system (PNS) inflammatory diseases, and invasive angiogenesis. In this regard, it will be appreciated that the disclosed binding molecules of the invention will be formulated so as to facilitate administration and promote stability of the active agent. Preferably, pharmaceutical compositions in accordance with the present invention comprise a pharmaceutically acceptable, non-toxic, sterile carrier such as physiological saline, non-toxic buffers, preservatives and the like. For the purposes of the instant application, a pharmaceutically effective amount of an anti-CD100 binding molecule, e.g., an antibody, or antigen-binding fragment, variant, or derivative thereof conjugated or unconjugated, shall be held to mean an amount sufficient to achieve effective binding to a target and to achieve a benefit, e.g., to ameliorate symptoms of a disease or disorder or to detect a substance or a cell.

The pharmaceutical compositions used in this invention comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

Preparations for parenteral administration includes sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include, e.g., water, alcoholic/aqueous solutions, emulsions or suspensions, including saline and buffered media. In the subject invention, pharmaceutically acceptable carriers include, but are not limited to, 0.01-0.1 M and preferably 0.05 M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as, for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi.

The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's Pharmaceutical Sciences (Mack Publishing Co.) 16th ed. (1980).

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., an anti-CD100 antibody, or antigen-binding fragment, variant, or derivative thereof, by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit such as those described in U.S. patent application Ser. No. 09/259,337. Such articles of manufacture will preferably have labels or package inserts indicating that the associated compositions are useful for treating a subject suffering from, or predisposed to a disease or disorder.

Parenteral formulations may be a single bolus dose, an infusion or a loading bolus dose followed with a maintenance dose. These compositions may be administered at specific fixed or variable intervals, e.g., once a day, or on an "as needed" basis.

Certain pharmaceutical compositions used in this invention may be orally administered in an acceptable dosage form including, e.g., capsules, tablets, aqueous suspensions or solutions. Certain pharmaceutical compositions also may be administered by nasal aerosol or inhalation. Such compositions may be prepared as solutions in saline, employing benzyl alcohol or other suitable preservatives, absorption promoters to enhance bioavailability, and/or other conventional solubilizing or dispersing agents.

The amount of an anti-CD100 binding molecule, e.g., antibody, or fragment, variant, or derivative thereof, that may be combined with the carrier materials to produce a single dosage form will vary depending upon the host treated and the particular mode of administration. The composition may be administered as a single dose, multiple doses or over an established period of time in an infusion. Dosage regimens also may be adjusted to provide the optimum desired response (a therapeutic or prophylactic response).

In keeping with the scope of the present disclosure, anti-CD100 antibodies, or antigen-binding fragments, variants, or derivatives thereof of the invention may be administered to a human or other animal in accordance with the aforementioned methods of treatment in an amount sufficient to produce a therapeutic effect. The anti-CD100 antibodies, or antigen-binding fragments, variants, or derivatives thereof of the invention can be administered to such human or other animal in a conventional dosage form prepared by combining the antibody of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of anti-CD100 binding molecules, e.g., antibodies, or antigen-binding fragments, variants, or derivatives thereof, of the invention may prove to be particularly effective.

By "therapeutically effective dose or amount" or "effective amount" is intended an amount of anti-CD100 binding molecule, e.g., antibody or antigen binding fragment thereof, that when administered brings about a positive therapeutic response with respect to treatment of a patient with a disease to be treated.

Therapeutically effective doses of the compositions of the present invention, for treatment of CD100-expressing cell-mediated diseases such as certain types of cancers, e.g., head and neck, prostate, colon, breast, and lung cancers; autoimmune diseases, e.g., arthritis, multiple sclerosis, inflammatory diseases including central nervous system (CNS) and peripheral nervous system (PNS) inflammatory diseases; and invasive angiogenesis, vary depending upon many different factors, including means of administration, target site, physiological state of the patient, whether the patient is human or an animal, other medications administered, and whether treatment is prophylactic or therapeutic. Usually, the patient is a human, but non-human mammals including transgenic mammals can also be treated. Treatment dosages may be titrated using routine methods known to those of skill in the art to optimize safety and efficacy.

The amount of at least one anti-CD100 binding molecule, e.g., antibody or binding fragment thereof, to be administered is readily determined by one of ordinary skill in the art without undue experimentation given the disclosure of the present invention. Factors influencing the mode of administration and the respective amount of at least one anti-CD100 binding molecule, e.g., antibody, antigen-binding fragment, variant or derivative thereof include, but are not limited to, the severity of the disease, the history of the disease, and the age, height, weight, health, and physical condition of the individual undergoing therapy. Similarly, the amount of anti-CD100 binding molecule, e.g., antibody, or fragment, variant, or derivative thereof, to be administered will be dependent upon the mode of administration and whether the subject will undergo a single dose or multiple doses of this agent.

The present invention also provides for the use of an anti-CD100 binding molecule, e.g., an antibody or antigen-binding fragment, variant, or derivative thereof, in the manufacture of a medicament for treating an autoimmune disease and/or inflammatory disease, including, e.g., arthritis, multiple sclerosis, CNS and PNS inflammatory diseases, or a cancer.

The invention also provides for the use of an anti-CD100 binding molecule, e.g., antibody of the invention, or antigen-binding fragment, variant, or derivative thereof, in the manufacture of a medicament for treating a subject for treating an autoimmune disease and/or inflammatory disease, or for treating a cancer, wherein the medicament is used in a subject that has been pretreated with at least one other therapy. By "pretreated" or "pretreatment" is intended the subject has received one or more other therapies (e.g., been treated with at least one other cancer therapy) prior to receiving the medicament comprising the anti-CD100 binding molecule, e.g., antibody or antigen-binding fragment, variant, or derivative thereof. "Pretreated" or "pretreatment" includes subjects that have been treated with at least one other therapy within 2 years, within 18 months, within 1 year, within 6 months, within 2 months, within 6 weeks, within 1 month, within 4 weeks, within 3 weeks, within 2 weeks, within 1 week, within 6 days, within 5 days, within 4 days, within 3 days, within 2 days, or even within 1 day prior to initiation of treatment with the medicament comprising the anti-CD100 binding molecule, for example, the monoclonal antibody 2503 disclosed herein, or antigen-binding fragment, variant, or derivative thereof. It is not necessary that the subject was a responder to pretreatment with the prior therapy or therapies. Thus, the subject that receives the medicament comprising the anti-CD100 binding molecule, e.g., an antibody or antigen-binding fragment, variant, or derivative thereof could have responded, or could have failed to respond (e.g., the cancer was refractory), to pretreatment with the prior therapy, or to one or more of the prior therapies where pretreatment comprised multiple therapies. Examples of other cancer therapies for which a subject can have received pretreatment prior to receiving the medicament comprising the anti-CD100 binding molecule, e.g., antibody or antigen-binding fragment, variant, or derivative thereof include, but are not limited to, surgery; radiation therapy; chemotherapy, optionally in combination with autologous bone marrow transplant, where suitable chemotherapeutic agents include, but are not limited to, those listed herein above; other anti-cancer monoclonal antibody therapy; small molecule-based cancer therapy, including, but not limited to, the small molecules listed herein above; vaccine/immunotherapy-based cancer therapies; steroid therapy; other cancer therapy; or any combination thereof.

IX. Diagnostics

The invention further provides a diagnostic method useful during diagnosis of CD100-expressing cell-mediated diseases such as certain types of cancers, autoimmune diseases, inflammatory diseases including, e.g., arthritis, multiple sclerosis, central nervous system (CNS) and peripheral nervous system (PNS) inflammatory diseases, and invasive angiogenesis, which involves measuring the expression level of CD100 protein or transcript in tissue or other cells or body fluid from an individual and comparing the measured expression level with a standard CD100 expression level in normal tissue or body fluid, whereby an increase in the expression level compared to the standard is indicative of a disorder.

The anti-CD100 antibodies of the invention and antigen-binding fragments, variants, and derivatives thereof, can be used to assay CD100 protein levels in a biological sample using classical immunohistological methods known to those of skill in the art (e.g., see Jalkanen, et. al., *J. Cell. Biol.* 101:976-985 (1985); Jalkanen et al., *J. Cell Biol.* 105:3087-3096 (1987)). Other antibody-based methods useful for detecting CD100 protein expression include immunoassays, such as the enzyme linked immunosorbent assay (ELISA), immunoprecipitation, or Western blotting. Suitable assays are described ore detail elsewhere herein.

By "assaying the expression level of CD100 polypeptide" is intended qualitatively or quantitatively measuring or estimating the level of CD100 polypeptide in a first biological sample either directly (e.g., by determining or estimating absolute protein level) or relatively (e.g., by comparing to the disease associated polypeptide level in a second biological sample). Preferably, CD100 polypeptide expression level in the first biological sample is measured or estimated and compared to a standard CD100 polypeptide level, the standard being taken from a second biological sample obtained from an individual not having the disorder or being determined by averaging levels from a population of individuals not having the disorder. As will be appreciated in the art, once the "standard" CD100 polypeptide level is known, it can be used repeatedly as a standard for comparison.

By "biological sample" is intended any biological sample obtained from an individual, cell line, tissue culture, or other source of cells potentially expressing CD100. Methods for obtaining tissue biopsies and body fluids from mammals are well known in the art.

X. Immunoassays

Anti-CD100 antibodies, or antigen-binding fragments, variants, or derivatives thereof of the invention may be assayed for immunospecific binding by any method known in the art. The immunoassays that can be used include but are not limited to competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, (1994) Current Protocols in Molecular Biology (John Wiley & Sons, Inc., NY) Vol. 1, which is incorporated by reference herein in its entirety). Exemplary immunoassays are described briefly below (but are not intended by way of limitation).

Immunoprecipitation protocols generally comprise lysing a population of cells in a lysis buffer such as RTPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al., eds, (1994) Current Protocols in Molecular Biology (John Wiley & Sons, Inc., NY) Vol. 1 at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or $^{125}$I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g. Ausubel et al., eds, (1994) Current Protocols in Molecular Biology (John Wiley & Sons, Inc., NY) Vol. 1 at 10.8.1.

ELISAs comprise preparing antigen, coating the well of a 96-well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest, to the coated well. One of skill in the art would be knowledgeable as to the parameters that can be modified to increase the signal detected as well as other variations of ELISAs known in the art. For further discussion regarding ELISAs see, e.g., Ausubel et al., eds, (1994) Current Protocols in Molecular Biology (John Wiley & Sons, Inc., NY) Vol. 1 at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^{3}$H or $^{125}$I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest is conjugated to a labeled compound (e.g., $^{3}$H or $^{125}$I) in the presence of increasing amounts of an unlabeled second antibody.

Anti-CD100 antibodies, or antigen-binding fragments, variants, or derivatives thereof of the invention, additionally, can be employed histologically, as in immunofluorescence, immunoelectron microscopy or non-immunological assays, for in situ detection of CD100 protein or conserved variants or peptide fragments thereof. In situ detection may be accomplished by removing a histological specimen from a patient, and applying thereto a labeled anti-CD100 antibody, or antigen-binding fragment, variant, or derivative thereof, preferably applied by overlaying the labeled antibody (or fragment) onto a biological sample. Through the use of such a procedure, it is possible to determine not only the presence of CD100 protein, or conserved variants or peptide fragments, but also its distribution in the examined tissue. Using the present invention, those of ordinary skill will readily perceive that any of a wide variety of histological methods (such as staining procedures) can be modified in order to achieve such in situ detection.

Immunoassays and non-immunoassays for CD100 gene products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of binding to CD100 or conserved variants or peptide fragments thereof, and detecting the bound antibody by any of a number of techniques well known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled anti-CD100 antibody, or antigen-binding fragment, variant, or derivative thereof. The solid phase support may then be washed with the buffer a second time to remove unbound antibody. Optionally the antibody is subsequently labeled. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-CD100 antibody, or antigen-binding fragment, variant, or derivative thereof may be determined according to well known methods. Those skilled in the art will be able to determine operative and optimal assay conditions for each determination by employing routine experimentation.

There are a variety of methods available for measuring the affinity of an antibody-antigen interaction, but relatively few for determining rate constants. Most of the methods rely on either labeling antibody or antigen, which inevitably complicates routine measurements and introduces uncertainties in the measured quantities.

Surface plasmon reasonance (SPR) as performed on BIA-CORE® offers a number of advantages over conventional methods of measuring the affinity of antibody-antigen interactions: (i) no requirement to label either antibody or antigen; (ii) antibodies do not need to be purified in advance, cell culture supernatant can be used directly; (iii) real-time measurements, allowing rapid semi-quantitative comparison of different monoclonal antibody interactions, are enabled and are sufficient for many evaluation purposes; (iv) biospecific surface can be regenerated so that a series of different monoclonal antibodies can easily be compared under identical conditions; (v) analytical procedures are fully automated, and extensive series of measurements can be performed without user intervention. BIAapplications Handbook, version AB (reprinted 1998), BIACORE® code No. BR-1001-86; BiAtechnology Handbook, version AB (reprinted 1998), BIACORE® code No. BR-1001-84. SPR based binding studies require that one member of a binding pair be immobilized on a sensor surface. The binding partner immobilized is referred to as the ligand. The binding partner in solution is referred to as the analyte. In some cases, the ligand is attached indirectly to the surface through binding to another immobilized molecule, which is referred as the capturing molecule. SPR response reflects a change in mass concentration at the detector surface as analytes bind or dissociate.

Based on SPR, real-time BIACORE® measurements monitor interactions directly as they happen. The technique is well suited to determination of kinetic parameters. Comparative affinity ranking is simple to perform, and both kinetic and affinity constants can be derived from the sensorgram data.

When analyte is injected in a discrete pulse across a ligand surface, the resulting sensorgram can be divided into three essential phases: (i) Association of analyte with ligand during sample injection; (ii) Equilibrium or steady state during sample injection, where the rate of analyte binding is balanced by dissociation from the complex; (iii) Dissociation of analyte from the surface during buffer flow.

The association and dissociation phases provide information on the kinetics of analyte-ligand interaction ($k_a$ and $k_d$, the rates of complex formation and dissociation, $k_d/k_a=K_D$). The equilibrium phase provides information on the affinity of the analyte-ligand interaction ($K_D$).

BIAevaluation software provides comprehensive facilities for curve fitting using both numerical integration and global fitting algorithms. With suitable analysis of the data, separate rate and affinity constants for interaction can be obtained from simple BIACORE® investigations. The range of affinities measurable by this technique is very broad ranging from mM to pM.

Epitope specificity is an important characteristic of a monoclonal antibody. Epitope mapping with BIACORE®, in contrast to conventional techniques using radioimmunoassay, ELISA or other surface adsorption methods, does not require labeling or purified antibodies, and allows multi-site specificity tests using a sequence of several monoclonal antibodies. Additionally, large numbers of analyses can be processed automatically.

Pair-wise binding experiments test the ability of two MAbs to bind simultaneously to the same antigen. MAbs directed against separate epitopes will bind independently, whereas MAbs directed against identical or closely related epitopes will interfere with each other's binding. These binding experiments with BIACORE® are straightforward to carry out.

For example, one can use a capture molecule to bind the first Mab, followed by addition of antigen and second MAb sequentially. The sensorgrams will reveal: (1) how much of the antigen binds to first Mab, (2) to what extent the second MAb binds to the surface-attached antigen, (3) if the second MAb does not bind, whether reversing the order of the pair-wise test alters the results.

Peptide inhibition is another technique used for epitope mapping. This method can complement pair-wise antibody binding studies, and can relate functional epitopes to structural features when the primary sequence of the antigen is known. Peptides or antigen fragments are tested for inhibition of binding of different MAbs to immobilized antigen. Peptides which interfere with binding of a given MAb are assumed to be structurally related to the epitope defined by that MAb.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods ID Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods ID Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described are generally followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (WIT. Freeman and Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevere, Amsterdam); Goldsby et al., eds. (2000) Kuby Immunnology (4th ed.; H. Freemand & Co.); Roitt et al, (2001) Immunology (6th ed.; London: Mosby); Abbas et al, (2005) Cellular and Molecular Immunology (5th ed.; Elsevier Health Sciences Division); Kontermann and Dubel (2001) Antibody Engineering (Springer Verlan); Sambrook and Russell (2001) Molecular Cloning: A Laboratory Manual (Cold Spring Harbor Press); Lewin (2003) Genes VIII (Prentice Hall 2003); Harlow and Lane (1988) Antibodies: A Laboratory Manual (Cold Spring Harbor Press); Dieffenbach and Dveksler (2003) PCR Primer (Cold Spring Harbor Press).

All of the references cited above, as well as all references cited herein, are incorporated herein by reference in their entireties.

The following examples are offered by way of illustration and not by way of imitation.

EXAMPLES

Example 1

Selection and Characterization of Antibodies Specific for CD100

Mouse anti-CD100 antibodies recognizing human, monkey and murine CD100 and were generated using the methods described below.

The "Line 1" cell line was derived from a spontaneous lung tumor in a BALM, mouse. The inventors previously showed that injecting BALB/c mice with live Line 1 cells transfected with a foreign cDNA was an effective way to induce immune responses (unpublished data). The Line 1 cell line was transfected with an expression plasmid encoding full length human CD100 cDNA (SEQ ID NO: 23). A stable line expressing human CD100 was isolated from the transfected cell line (Line1.CD100). CD100 deficient mice (BALB/c background, see Kumanogoh et al., J. Immunol. 169:1175-1181 (2002)) were primed by immunization with purified mouse CD100-His (the extracellular domain of mouse CD100 with a C-terminal 6x his tag for purification) emulsified in complete Freund's adjuvant (CFA). One week following this immunization, the mice were injected intramuscularly (i.m.) with 200,000 live Line1.CD100 cells. Nineteen days after the Line1.CD100 injection the mice were sacrificed and spleens were harvested and fused with P3X63Ag8.653 fusion partner (ATCC# CRL-1580) following standard procedures to generate hybridomas. Hybridoma clones were screened by ELISA for binding to human and mouse CD100. In particular, a hybridoma cell line, specific for MAb 67, was prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 571-681 (1981)). A large panel of mouse CD100 specific antibodies was generated. Most of these antibodies also bound with high affinity to human CD100. Two hybridomas, clones 67-2 and 76-1, produced monoclonal antibodies (called MAb 67 and MAb 76, respectively) that exhibited high affinity for both mouse and human CD100 (See Table 2).

TABLE 2

Affinity measurements for mouse anti-CD100 MAbs

| MAb | Isotype | Affinity for Mouse CD100 (nM)* | Affinity for Human CD100 (nM)* |
|---|---|---|---|
| 67 | IgG1 | 1.00 | 5.7 |
| 76 | IgG2b | 0.33 | 0.12 |

*Affinity was measured using BIACORE ® surface plasmon resonance technology

An antibody cross-blocking ELISA demonstrated that MAb 67 and MAb 76 recognize distinct epitopes on CD100. In addition, MAbs 67 and 76 recognize an epitope that is distinct from that recognized by the independently derived murine anti-human CD100 antibody BD16 (described in US 2008/0219971 A1). Thus, two independent mouse anti- CD100 antibodies, MAb 76 (see SEQ ID NOs: 25-40) and MAb 67 (see SEQ ID NOs: 3-8; 10; 11-16; 18; 20 and 22), were generated.

Example 2

MAbs 67 and 76 Block Activity of Mouse and Human CD100 In Vitro

CD100 specific antibodies were screened for their ability to inhibit CD100 binding in a fluorescence blocking assay. An illustration of the method used to test whether the CD100 specific antibodies blocked CD100 from binding to Plexin B1 is shown in FIG. 1. Human 293 cells were transfected with cDNA encoding a CD100 receptor: Plexin B1. A stable cell line expressing Plexin B1 was selected (293/Plexin). CD100-His bound to Plexin B1 on the cell surface was detected by flow cytometry using a biotin conjugated His tag specific monoclonal antibody and streptavidin-APC. When a tested anti-CD100 MAb was able to block binding of CD100 to Plexin B1, then less CD100-His was detected on the cell, resulting in lower fluorescence.

Forty nanograms (ng) of human or mouse CD100-His (C-terminal His tag) were incubated alone or with various concentrations of anti-CD100 MAb overnight at 4° C. The next morning, either (1) CD100 only or (2) CD100 pre-incubated with an anti-CD100 MAb (67 or 76) was combined with the 293/Plexin cells and incubated for 30 minutes on ice. CD100 that bound to the cell through Plexin B1 was detected using biotinylated polyclonal rabbit anti-His MAb, followed by streptavidin-APC, and cells were analyzed by flow cytometry. The results indicated that neutralization of CD100 resulted in lower fluorescence. In particular, pre-incubating CD100 with MAb 67 or MAb 76 resulted in lower fluorescence compared to CD100 only (FIG. 2). Increasing the concentration of anti-CD100 MAb 67 or 76 from 0.156 µg/ml to 0.625 resulted in a further reduction in fluorescence. Similar blocking of human CD100 was also observed (data not shown). Thus, these results showed that MAb 67 and MAb 76 were both able to block human and mouse CD100 from binding to Plexin B1.

CD100/Plexin B1 signaling has been shown to induce detachment from the extracellular matrix and cell collapse by inducing reorganization of actin filaments (See Kruger et al., *Nature Reviews Molecular Cell Biology* 6:789-800 (2005)). A heterologous assay to determine cellular detachment following binding to an extracellular matrix was used to determine whether anti-CD100 antibodies could block CD100 induced detachment of 293/Plexin cells from Fibronectin coated plates.

For the cell detachment assay, 293/plexin cells (normally grown as a suspension cell line) were plated at a density of 40,000 cells/well onto a fibronectin coated 96 well plate and allowed to attach overnight. Two (2) µg/ml of mouse CD100-His (C-terminal His tag) was incubated alone or with various concentrations of an anti-CD100 MAb (67 or 76) for 6 hours at 4° C. CD100 samples were then brought up to room temperature before addition to the 293/plexin cells. Cells were treated with CD100 or CD100 pre-incubated with antibody for 30 minutes at 37° C., washed twice with PBS, and stained with crystal violet for 15 minutes. Cells were then washed twice with PBS and dried. Images were taken on a scanner for documentation. The crystal violet was then solubilized for 15 minutes at RT with 100 µl of 33% glacial acetic acid, and pipetted into a new plate. Absorbance was read at 570 nm. CD100 causes a reduction in the number of cells attached to the plate, and thus a reduced absorbance, while neutralization of CD100 results in an increase in absorbance.

As shown in FIG. 3, both MAb 67 and MAb 76 were able to block mouse CD100 mediated cell detachment and increase absorbance compared to isotype control. Similarly, both MAbs were also able to block cell detachment mediated by human CD100 (data not shown).

MAbs 67 and 76 blocked binding of CD100 to cell surface Plexin B1 and induced detachment of 293/Plexin cells from Fibronectin coated plates. The results of the in vitro functional assays described above showed that MAb 67 and MAb 76 were able to block the function of mouse and human CD100 in vitro.

Example 3

Evaluation of Anti-CD100 Monoclonal Antibodies in Mouse Disease Models

Anti-CD100 neutralizing monoclonal antibodies (76 and 67) were tested in vivo in the SJL, EAE animal model. Relapsing experimental autoimmune encephalomyelitis (R-EAE) is a CD4+ T cell-mediated disease characterized by inflammation and demyelination within the central nervous system. In SJL, mice, R-EAE can be induced by immunization with a peptide epitope of proteolipid protein (PLP$_{139-151}$) (HSLGKWLGHPDKF; SEQ ID NO: 24). This model is characterized by a moderate to severe acute paralytic phase followed by remission and subsequent relapses. Disease severity was scored using the scale shown in Table 3,

TABLE 3

Evaluation of the EAE clinical signs

| Score | Signs | Description |
|---|---|---|
| 0 | Normal behavior | No neurological signs. |
| 1 | Distal limp tail | The distal part of the tail is limp and droopy. |
| 1.5 | Complete limp tail | The whole tail is loose and droopy. |
| 2 | Righting reflex | Animal has difficulties rolling onto its feet when laid on its back. |
| 3 | Ataxia | Wobbly walk - when the mouse walks the hind legs are unsteady. |
| 4 | Early paralysis | The mouse has difficulties standing on its hind legs but still has remnants of movement. |
| 5 | Full paralysis | The mouse can't move its legs at all, it looks thiner and emaciated. |
| 6 | Moribund/Death | Death. |

SJL mice were immunized with 100 µg PLP$_{139-151}$ in CFA. Pertussis toxin was administered on Day 0 and again 4 hours later. Mice were treated with 30 mg/kg MAb 76, 67 or isotype control antibody twice per week starting on Day 0, or once per week starting at Day 7. Scoring of EAE clinical signs was initiated from the 10th day post-EAE induction.

Figure 4A:
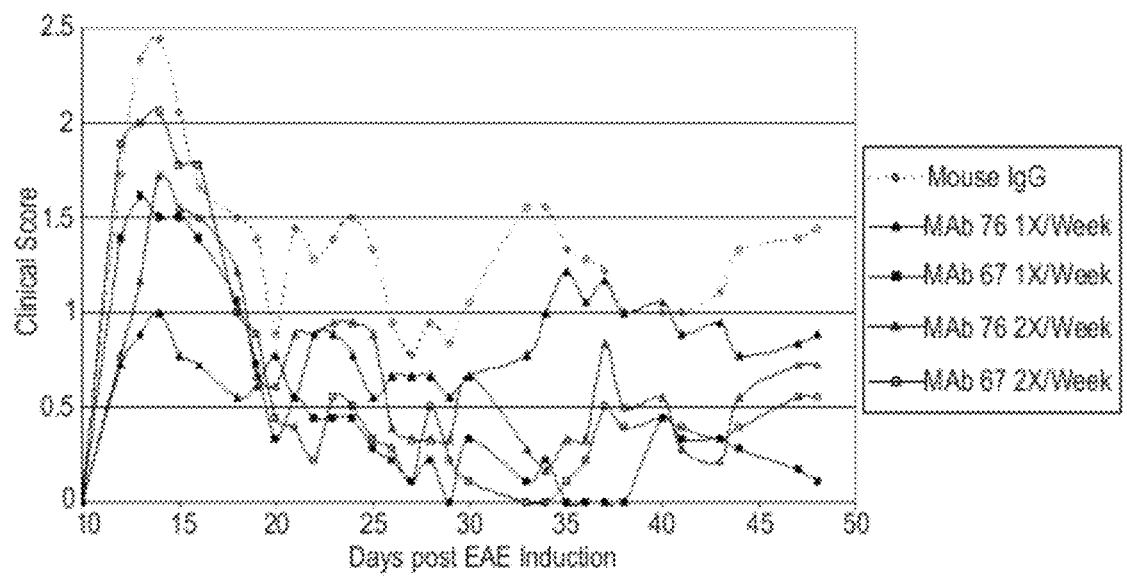
Figure 4B:
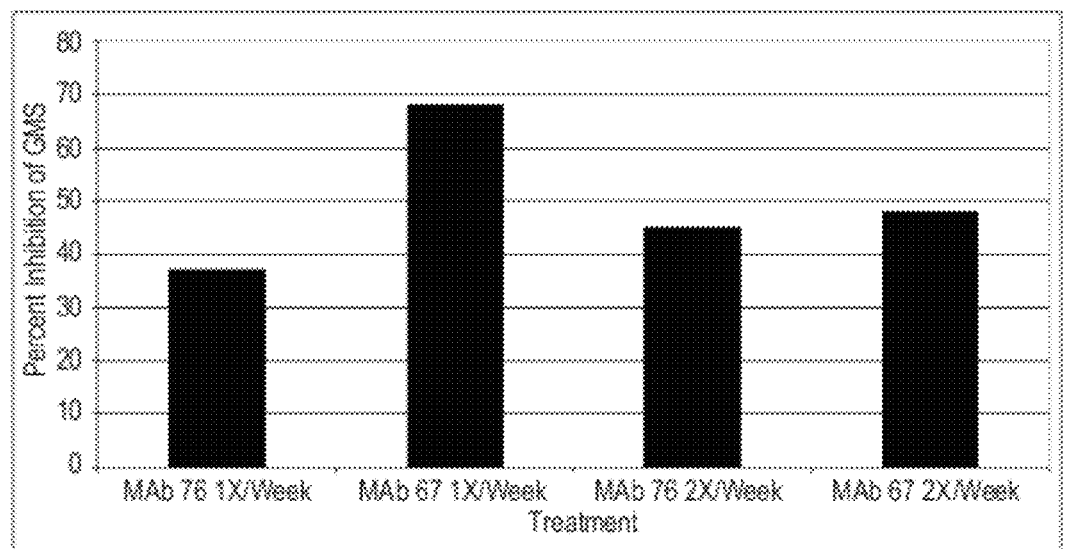

As shown in FIG. 4A, treatment with MAb 76 or MAb 67 reduced the severity of EAE in SJL mice compared to mouse IgG control. The percent reduction in Group Mean Score (GMS) between Day 21 and the end of the study, for MAbs 76 and 67 at 1×/week and 2×/week each is shown in FIG. 4B. As shown in FIG. 4B, MAb 76 (1×/week) had a percent inhibition of GMS of 35-40%; MAb 67 (1×/week) had a percent inhibition of GMS of 65-70%; MAb 76 (2×/week) had a percent inhibition of GMS of 40-50%; and MAb 67 (2×/week) had a percent inhibition of GMS of 45-50%. These results show that both MAb 67 and MAb 76 attenuated relapsing remitting EAE in SJL mice.

The SJL EAE study was repeated using MAb 76 at 30 mg/kg dose and dosing 1×/week. The results further demonstrated that MAb 76 was able to reduce the severity of EAE in SJL mice compared to mouse IgG (data not shown). The percent reduction in Group Mean Score (GMS) between Day 21 and the end of the study was between 50-60%. Furthermore, the SJL EAE study was repeated using MAb 76 or MAb 67 at 30 mg/kg dosing 1×/week. Treatment with MAb 67 or MAb 76 resulted in a percent reduction in GMS of between 30-40% between Day 18 and the end of the study. The results in FIGS. 5A and 5B further demonstrate that MAb 76 and MAb 67 were able to reduce the severity of EAE in SJL mice.

The SJL FAR study was repeated using MAb 67 at 30 mg/kg dosing 1×/week where treatment started at day 7 post-immunization. Treatment with MAb 67 starting at day 7 resulted in a percent reduction in GMS of about 50% between Day 12 and the end of the study. The results are shown in FIG. 6.

The results from these in vivo studies demonstrate that neutralization of CD100 using MAb 76 or MAb 67 reduced the clinical signs of EAE in different murine EAE experiments. The results for MAb 76 and MAb 67 were similar to one another in these experiments.

These results demonstrated that MAb 76 and MAb 67 have the ability to block CD100 activity in vitro, and, importantly, the ability to reduce the severity of EAE in different dosing experiments in the mouse EAE model.

Example 4

Preparation of Chimeric and Humanized Anti-CD100 Monoclonal Antibodies

The murine monoclonal antibody clone 67, described above, has been shown to have the ability to neutralize both human and mouse CD100 in vitro and to ameliorate EAE in murine models in vivo.

The variable heavy (VH) and variable light (VK) genes were cloned from the clone 67 hybridoma and their sequence was determined. The amino acid sequences of the MAb 67 VH and VK genes are shown below with the CDR1, CDR2 and CDR3 regions underlined.

```
MAb 67 VH:
                                          (SEQ ID NO: 10)
QVQLQQSGPELVKPGASVKISCKASGYSFSDYYMHWVKQSPENSLEW
IGQINPTTGGASYNQKFKGKATLTVDKSSSTAYMQLKSLTSEESAVY
YCARRYYYGRHFDVWGQGTTVTVSS

MAb 67 VK:
                                          (SEQ ID NO: 18)
DIVMTQSPASLAVSLGQRATISCKASQSVDYDGDSYMNWYQQKPGQP
PKLLIYAASNLESGIPARFSGSGSGTDFTLNIHPVEEEDAATYYCQQ
SNEDPYTFGGGTKLEIK
```

The MAb 67 VH gene was cloned into a mammalian expression vector that contained the human gamma 4 heavy chain constant region coding sequence, creating a full length chimeric heavy chain. The MAb 67 VK was cloned into a mammalian expression vector that had the human Kappa constant region coding sequence, creating a full length chimeric light chain, in order to make a chimeric antibody, the expression vectors containing the chimeric heavy chain and the chimeric light chain were co-transfected into CHO-S cells. The monoclonal antibody that was produced was secreted from the cells and harvested after a 3-6 day expression period. The resulting MAb was purified using Protein A chromatography and characterized. The resulting chimeric MAb (MAb 2368) was demonstrated to be specific for CD100 by flow cytometry and by ELISA, and was shown to be able to compete with murine MAb 67 for binding to CD100. Collectively, these data demonstrate that the correct VH and VK genes encoding the 67 MAb were isolated.

The MAb 67 variable CDR regions were used to create a humanized monoclonal antibody. The humanized VH and VK genes were respectively cloned into vectors containing the human gamma 4 and human kappa constant domains. The pairing of the humanized VH and the humanized VK created the IgG4/kappa MAb 2503. The amino acid sequences of the humanized MAb 67 VH (H2160) and VK (L553) are shown below with the CDR1, CDR2 and CDR3 regions underlined.

```
Sequence of H2160:
                                          (SEQ ID NO: 9)
QVQLVQSGAEVKKPGSSVKVSCKASGYSFSDYYMHWVRQAPGQGLEW
MGQINPTTGGASYNQKFKGKATITVDKSTSTAYMELSSLRSEDTAVY
YCARYYYGRHFDVWGQGTTVTVSS Sequence of L553:
                                          (SEQ ID NO: 17)
DIVMTQSPDSLAVSLGERATINCKASQSVDYDGDSYMNWYQQKPGQP
PKLLIYAASNLESGVPDRFSGSGSGTDFTLTISSLQAEDVAVYYCQQ
SNEDPYTFGQGGTKLEIK
```

Polynucleotides encoding the VH (Human Immunoglobulin gene with human gamma; H2160) and VK (Human Immunoglobulin gene with human kappa L553) regions of MAb 2503 antibody were cloned into pCMV-Script (Stratagem) vectors and were deposited with the American Type Culture Collection ("ATCC") on May 7, 2009, and given ATCC Deposit Numbers PTA-10004 and PTA-10005, respectively. The ATCC is located at 10801 University Boulevard, Manassas, Va. 20110-2209, USA. The ATCC deposits were made pursuant to the terms of the Budapest Treaty on the international recognition of the deposit of microorganisms for purposes of patent procedure.

Example 5

Characterization of Humanized Anti-CD100 Monoclonal Antibody 2503

Specificity of MAb 2503 was characterized by ELISA and Flow Cytometry. MAb 2503 was tested in an epitope competition assay with MAb 67 and in an affinity determination assay using BIACORE® surface plasmon resonance technology.

The epitope specificity of MAb 2503 and MAb 67 were determined by competition ELISA. For the ELISA protocol, an ELISA plate was coated with CD100-Fc. Mouse 67 or humanized 2503 MAbs were titrated. The antibodies were allowed to bind to CD100 and unbound antibody was wash away. Biotinylated MAb 67 was added. The antibodies were allowed to bind to CD100 and unbound antibody was wash away. Biotinylated MAb 67 bound to CD100 was detected using Streptavidin-HRP. The ability of MAb 2503 or MAb 67 to block binding of biotinylated 67 to human CD100 (shown in FIG. 7A) and mouse CD100 (shown in FIG. 7B) was analyzed by ELISA.

Binding affinities of anti-CD100 MAbs were determined using BIACORE® surface plasmon resonance technology. MAb 2503 was shown to only bind CD100 (human, mouse and marmoset) and CD100 expressing cell lines, indicating that MAb 2503 is specific for CD100. MAb 2503 showed an increased affinity for human and mouse CD100 compared to MAb 67. A summary of the affinity characteristics of MAb 2503 and MAb 67 is presented below in Table 4.

TABLE 4

Affinities of anti-CD100 MAbs for human, marmoset and mouse CD100

| MAb | Affinity for Human CD100 (nM)* | Affinity for Marmoset CD100 (nM)* | Affinity for Mouse CD100 (nM)* |
|---|---|---|---|
| 67 | 5.1 | 2.7 | 1.3 |
| 2503 | 5.4 | 2.4 | 1.5 |

*Affinity was measured using BIACORE ® surface plasmon resonance technology

These assays show that MAb 2503 is CD100 specific and binds to the same epitope as mouse MAb 67. MAb 2503 was shown to bind both mouse and human CD100, thus an advantage of MAb 2503 is that it can be tested for safety and efficacy in mice and also in humans. Furthermore, it was shown that MAb 2305 bound to human, monkey, and mouse CD100.

Example 6

MAb 2503 Blocks Activity of Mouse and Human CD100 In Vitro

MAb 2503 was tested for the ability to block the function of CD100 using the assays described above in Example 2, including (1) the flow cytometry blocking assay and (2) the cell detachment assay.

CD100 specific antibodies, MAb 67 and MAb 2503, were screened for their ability to inhibit CD100 binding to Plexin B1 in a fluorescence blocking assay. The method used to test whether the CD100 specific antibodies blocked CD100 from binding to Plexin B1 was shown in FIG. 1 (Example 2). Pre-incubating CD100 with MAb 67 or MAb 2503 resulted in lower fluorescence compared to CD100 only. MAb 2503 was able to block binding of human (see FIG. 8A), marmoset (see FIG. 8B) and mouse (see FIG. 8C) CD100 in vitro. Thus, these results showed that MAb 67 and MAb 2503 were both able to block human, monkey and mouse CD100 from binding to Plexin B1.

Figure 9A:
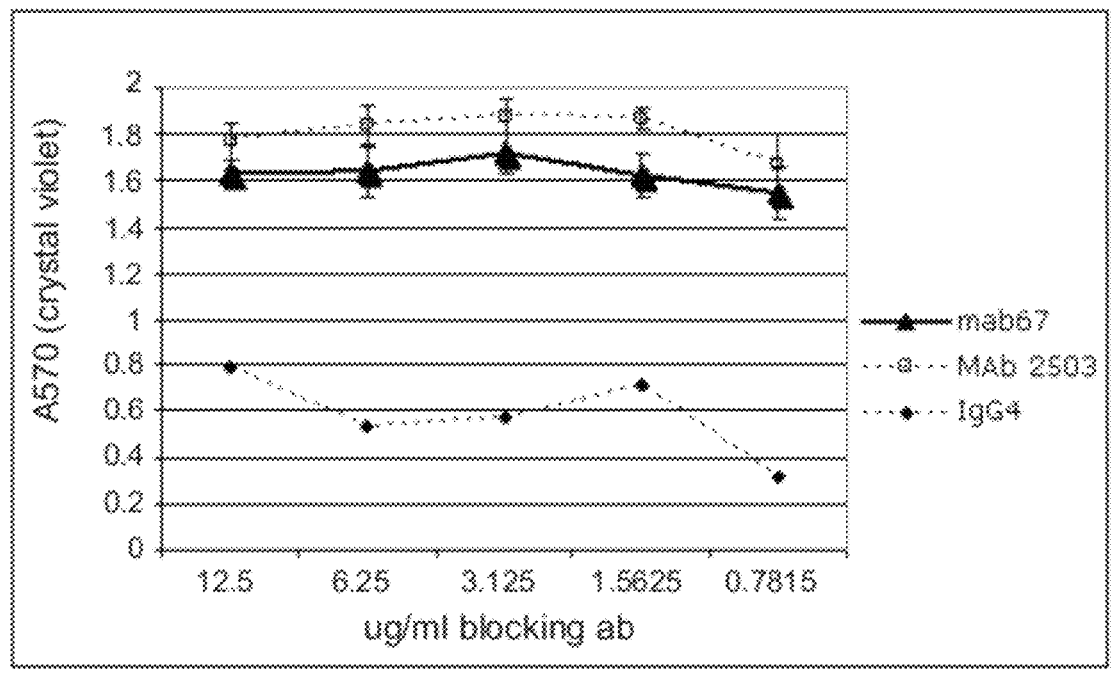
Figure 9B:
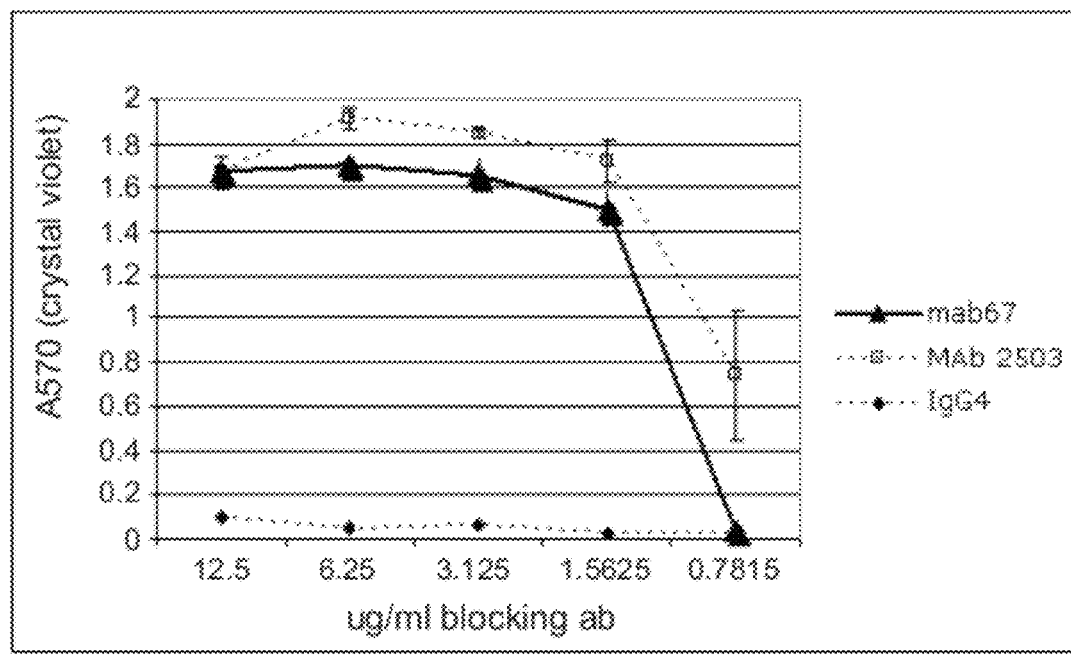

The ability of anti-CD100 MAbs to block human and monkey CD100 mediated detachment of 293/Plexin cells from a fibronectin coated plate was determined using the cell detachment assay described in Example 2. CD100 causes a reduction in the number of cells attached to the plate, and thus a reduced absorbance. Neutralization of human CD100 and marmoset CD100 with MAb2503 or MAb 67 resulted in an increase in absorbance as shown in FIGS. 9A and 9B, respectively. MAb 2503 and MAb 67 also neutralized mouse CD100 in this assay (Data not shown).

MAb 2503 blocked binding of human, mouse and monkey CD100 to cell surface Plexin B1 and induced detachment of 293/Plexin cells from Fibronectin coated plates. Thus, these results show that MAb 2503 was able to functionally neutralize human, mouse and monkey CD100.

Example 7

Anti-CD100 Antibody Inhibits Angiogenesis In Vivo

CD100 is a potent pro-angiogenic molecule and activation of Plexin B1 through CD100 binding transactivates c-Met and promotes the invasive ability of tumor cells and promotes angiogenesis.

To demonstrate the in vivo effect of the absence of CD100 on tumor growth, CT26 tumor cells were injected into the leg muscle of wild-type Balb/c or CD100–/– mice and the resulting tumor growth was measured. As shown in FIG. 10, the tumor volume in CD100–/– mice was decreased compared to wild-type Balb/c mice in this study. These results demonstrated that a mouse colon cancer cell line (CT26) has impaired growth in an environment lacking CD100.

Next, the ability of MAb 67 to reduce the growth of CT26 tumor cells in wild-type Balb/c mice was tested. CT26 tumor cells were injected into the leg muscle of wild-type Balb/c (n=48) or CD100–/– (n=9) mice. Following injection, the wild-type mice were split into 2 groups of 24 mice each. One group was treated starting on Day 1 by i.p. injection with 1 mg MAb 67, and the other group was treated by i.p. injection with 1 mg mouse IgG. Treatments were repeated every 7 days. The mice were analyzed for tumor growth. As shown in FIG. 11, treatment with MAb 67 reduced the growh of CT26 tumors in Balb/c mice compared to the mouse IgG control group.

Thus, these results show that an antibody having the structural and functional characteristics of MAb 67 reduced tumor growth in vivo.

Example 8

Anti-CD100 Antibody Inhibits Collagen Induced Arthritis In Vivo

MAb 67 was tested for its ability to reduce arthritis is the Collagen Induced Arthritis (CIA) mouse model. The collagen-induced arthritis (CIA) model is a preclinical animal inflammation model of rheumatoid arthritis (RA) that is widely used to address disease pathogenesis and validate therapeutic RA targets (Brand et al., *Nat. Protoc.* 2(5):1269-75 (2007)). The general CIA procedure is illustrated in FIG. 12 (any modifications to this general procedure are described below). Briefly, arthritis was induced at day 0 by intradermal tail injection of an emulsion comprising collagen and Complete Freund's Adjuvant (CFA). Thereafter, the control and test treatments were administered by subcutaneous (s.c.) or intraperitoneal (i.p.) injection twice weekly starting on day 20. The test groups for Study 1 are described below in Table 5.

TABLE 5

Collagen Induced Arthritis (CIA) Study 1 test groups

| Group # | # Animals | Treatment | Dose | Treatment Days |
|---|---|---|---|---|
| 1 | 10 | Mouse IgG Isotype control | 600 µg i.p. | 2X/week starting on Day 20 |
| 2 | 10 | MAb 67 | 600 µg i.p. | 2X/week starting on Day 20 |
| 3 | 10 | etanercept | 600 ug s.c. | 2X/week starting on Day 20 |

The disease severity was scored using the scale shown in Table 6. Each mouse paw received a score (macroscopic signs of arthritis were evaluated 3-times weekly). The Arthritic Index (AI) was calculated by addition of individual paw scores (maximum AI=16). Typically, the first signs of arthritis appear in the CIA model 21-28 days after immunization.

TABLE 6

| | CIA Scoring Method |
|---|---|
| Score | Description |
| 0 | no visible effects of arthritis |
| 1 | edema and/or erythema of 1 digit |
| 2 | edema and/or erythema of 2 digits |
| 3 | edema and/or erythema of more than 2 digit |
| 4 | severe arthritis of entire paw and digits |

Figure 13A:
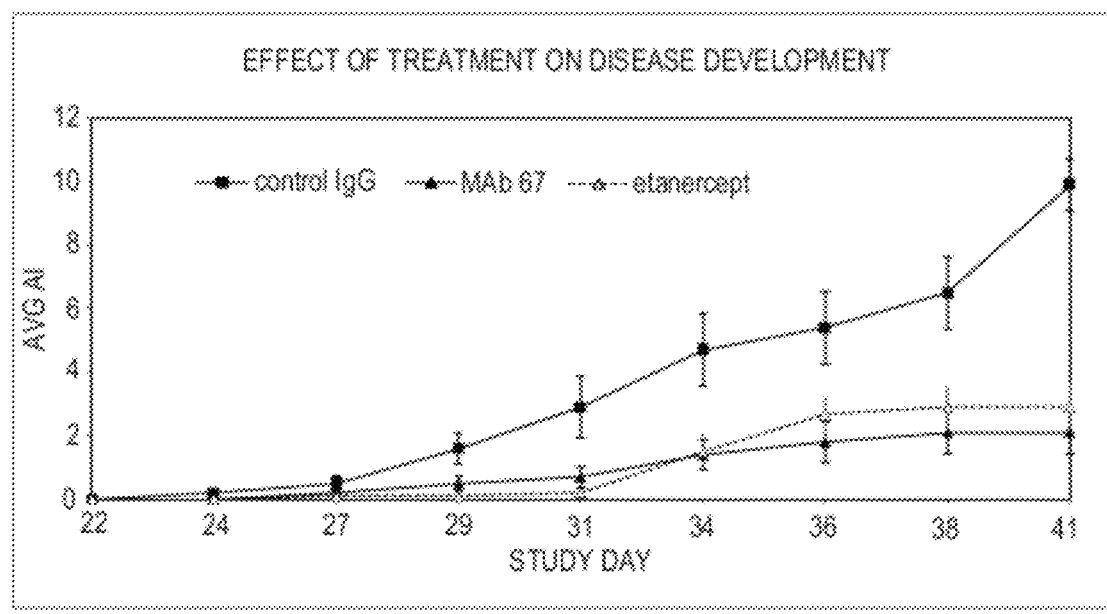

The results of Study 1 showed a reduction in arthritis disease development in the CIA model in groups treated with 600 μg MAb 67. Arthritic Index (AI) in mice treated with 600 μg MAb 67 was compared to AI in mice treated with 600 mg negative control (IgG1) and 600 μg positive control (etanercept) where treatment was started at day 20. Results are shown in FIG. 13A. These results show that MAb 67 was as good as or better than etanercept at reducing arthritis disease development in the CIA model.

A second study (Study 2) included MAb 67 and positive control treatments where the treatment was delayed, i.e., started when the Arthritis Index was ≥3. The test groups for Study 2 are described below in Table 7.

TABLE 7

| Collagen Induced Arthritis (CIA) Study 2 test groups | | | | |
|---|---|---|---|---|
| Group # | # Animals | Treatment | Dose | Treatment Days |
| 1 | 10 | Mouse IgG Isotype control | 600 μg i.p. | 2X/week starting on Day 20 |
| 2 | 10 | MAb 67 | 600 μg i.p. | 2X/week starting on Day 20 |
| 3 | 10 | MAb 67 | 600 μg i.p. | 2X/week starting when Arthritis Index is ≥3 |
| 4 | 10 | etanercept | 600 ug s.c. | 2X/week starting when Arthritis Index is ≥3 |

Figure 13B:
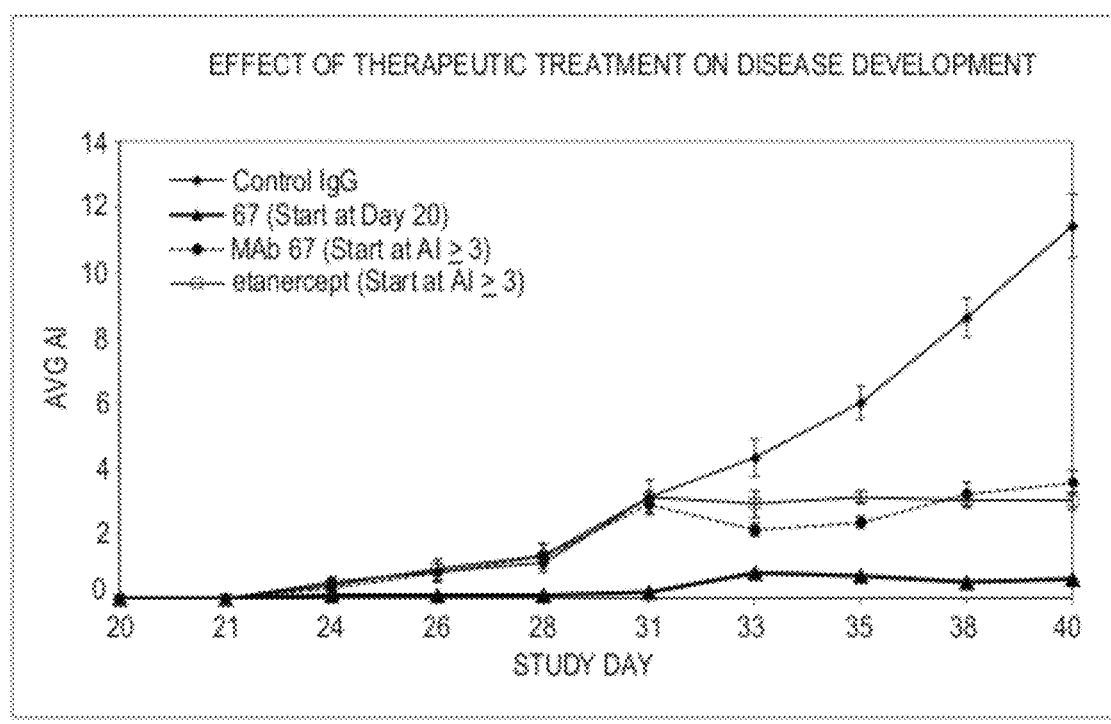

For Study 2, the AI results for treatment with MAb 67 (treatment started at day 20 or when the AI was ≥3) were compared to treatment with a negative control (IgG1) and positive control (etanercept; treatment started when the AI was ≥3). The results are shown in FIG. 13B. These results show that MAb 67 was as good as or better than etanercept at reducing arthritis disease development in the CIA model when treatment was started at day 20 or delayed to AI≥3. Thus, MAb 67 was shown to prevent arthritis disease development, as well as treat arthritis disease when administered once AI was ≥3 e CIA model.

Example 9

Anti-CD100 Antibody Blocks Primary and Memory B Cell Responses In Vivo

Balb/c and CD100−/− mice were immunized with (4-hydroxy-3-nitrophenyl)acetyl conjugated chicken gamma globulin precipitated with alum (aluminum-/magnesium-hydroxide) ("NP-CGG") followed by treatment with control IgG1 (Balb/c and CD100−/−) or MAb 67 (Balb/c only). The test groups are shown below in Table 8.

TABLE 8

| Primary and memory B-cell response test groups | | | | | | |
|---|---|---|---|---|---|---|
| Group | Strain | # animals | challenge | Ab treatment | dose | Ab Injection |
| 1 | CD100−/− | 6 | N/A | N/A | N/A | N/A |
| 2 | CD100−/− | 6 | NP-CGG/Alum | Control IgG1 | N/A | Day (−7), 0, 7, 14, 21, 28 |
| 3 | Balb/c | 6 | N/A | N/A | N/A | N/A |
| 4 | Balb/c | 6 | NP-CGG/Alum | Control IgG1 | 600 ug | Day (−7), 0, 7, 14, 21, 28 |
| 5 | Balb/c | 6 | NP-CGG/Alum | MAb 67 | 600 ug | Day (−7), 0, 7, 14, 21, 28 |

The mice were treated as described above in Table 8 starting on Day −7 and were immunized with NP-CGG on Day 0. Three mice per group were euthanized on Day 10, and the spleen and lymph nodes were analyzed for germinal center (GC) B cells ("B220+CD38lowPNA+"). Each spleen was analyzed separately, and the lymph nodes from all three mice were combined into one sample for analysis. Treatment of the remaining mice was continued as shown in Table 8. On Day 21 the mice were boosted with the same NP-CGG in Alum. On Day 31 the remaining mice were euthanized and the spleen and lymph nodes were analyzed for germinal center (GC) B cells ("B220+CD38lowPNA+"). Each spleen was analyzed separately, and the lymph nodes from all three mice were combined into one sample for analysis. The results in FIGS. 14A and B show that treatment with 600 μg MAb 67 decreased the number of GC B cells in spleen (SP) and lymph nodes (LN) after both primary immunization (14A) and secondary immunization (14B), respectively. Thus, MAb 67 was shown to block primary and memory B cell responses in vivo.

Example 10

Anti-CD100 Antibody Slows Growth In Vivo

Reduction of tumor growth by MAb 67 was tested in CT26 and BCA34 mouse xenograft tumor models. For these studies, tumor cells were injected intramuscularly into the legs of Balb/c mice. Starting 1 day post-graft, mice were treated by intraperitoneal (i.p.) injection 1× per week with 1 mg MAb 67 antibody or negative control (IgG) in 0.2 ml volume. Change in tumor volume ($mm^3$) and/or thigh volume ($mm^3$) was measured to determine tumor growth rates. The tumor growth rate for MAb 67 treated mice compared to the tumor growth rate in negative control mice was used to calculate tumor growth delay (TGD).

The ability of BCA34 and EMT6 tumor cells to grow in an environment lacking CD100 was also tested. For these studies, tumor cells were injected into the legs of Balb/c and CD100−/− (SEMA4D−/−) mice and tumor growth was measured.

CT26 Colon Tumor Cells

CT26 tumor cells are derived from murine colon tumors and express very low levels of CD100. 50,000 CT26 colon tumor cells were injected s.c. into wild-type Balb/c mice (20 mice/treatment group). The change in tumor volume (mm$^3$) was measured in mice treated with 1 mg MAb 67 weekly starting on Day 1 post-graft compared to mice injected with IgG control. The results (mean tumor volume over time) are shown in FIG. 15. The TGD for mice treated with MAb 67 was 17% (p=0.0317). These results show that CT26 tumor growth was reduced in MAb 67 treated mice.

BCA34 Fibroblastic Tumor Cells

Figure 16A:
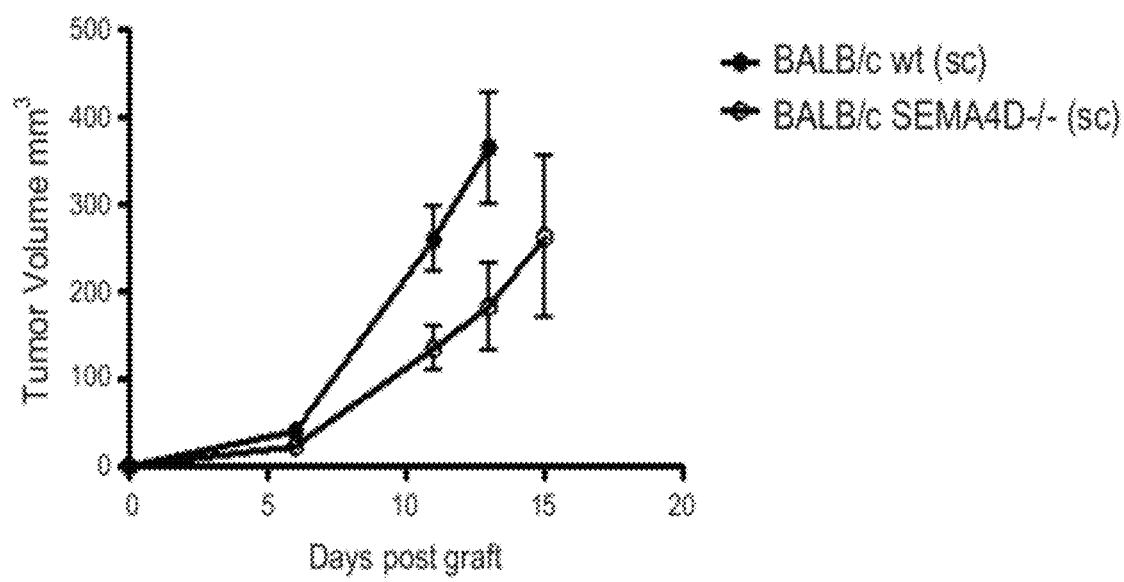

BCA34 tumor cells express low levels of CD100. First, 50,000 BCA34 tumor cells were s.c. injected into the abdominal region of wild-type Balb/c mice or CD100–/– ("SEMA4D–/–") mice. The change in tumor volume (mm$^3$) was measured in these mice, and the results are shown in FIG. 16A. These results showed that BCA34 tumor cells had impaired growth in an environment lacking CD100.

Figure 16B:
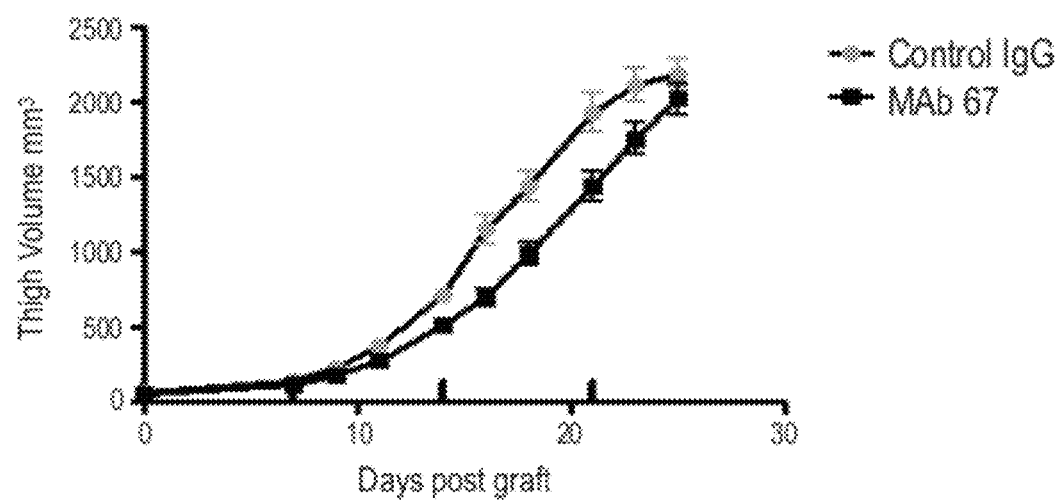

In a separate experiment, 50,000 BCA34 tumor cells were injected into the leg muscles of wild-type Balb/c mice (21 mice/treatment group). The change in tumor volume (mm$^3$) was measured in mice treated with 1 mg MAb 67 weekly starting on Day 1 post-graft compared to mice injected with IgG control. The results (mean thigh volume over time) are shown in FIG. 16B. The TGD for mice treated with MAb 67 was 18% (p=0.009). These results show that BCA34 tumor growth was reduced in MAb 67-treated mice.

EMT6 Mammary Carcinoma Tumor Cells

EMT6 tumor cells are derived from murine mammary carcinoma tumors and express moderate levels of CD100. 50,000 EMT6 tumor cells were injected into the leg muscles of wild-type Balb/c mice or CD100–/– ("SEMA4D–/–") mice. The change in tumor volume (mm$^3$) was measured in these mice, and the results are show in FIG. 17. Change in tumor volume (mm$^3$) is shown for wild-type Balb/c mice and CD100–/– mice ("SEMA4D–/–"). These results showed that EMT6 tumor cells had impaired growth in an environment lacking CD100.

Example 11

Anti-CD100 Antibody Slows Human Tumor Growth In Vivo

Reduction of tumor growth by MAb 2503 was tested in HN12 and HN6 HIF1a mODD human xenograft tumor models. HN12 and HN6 HIF1a mODD are derived from human head and neck tumors, and both xenografts express high levels of HIF1a and CD100. The HN6 HIF-1a mODD xenograft model is described in Sun et al., *J Biol Chem* 284(46):32066-74 (2009). For these experiments. 2 tumors/mouse were s.c. injected into athymic nude mice (10 mice/treatment group). Starting 1 day post-graft, mice were treated by i.p. injection 1× per week with 1 mg MAb 2503 antibody or negative control (IgG4) in 0.2 ml volume. Change in tumor volume (mm$^3$) was measured. The tumor growth rate for MAb 2503-treated HN6 HIF-1a mODD mice compared to the growth rate in negative control mice was used to calculate tumor growth delay (TGD).

Figure 19A:
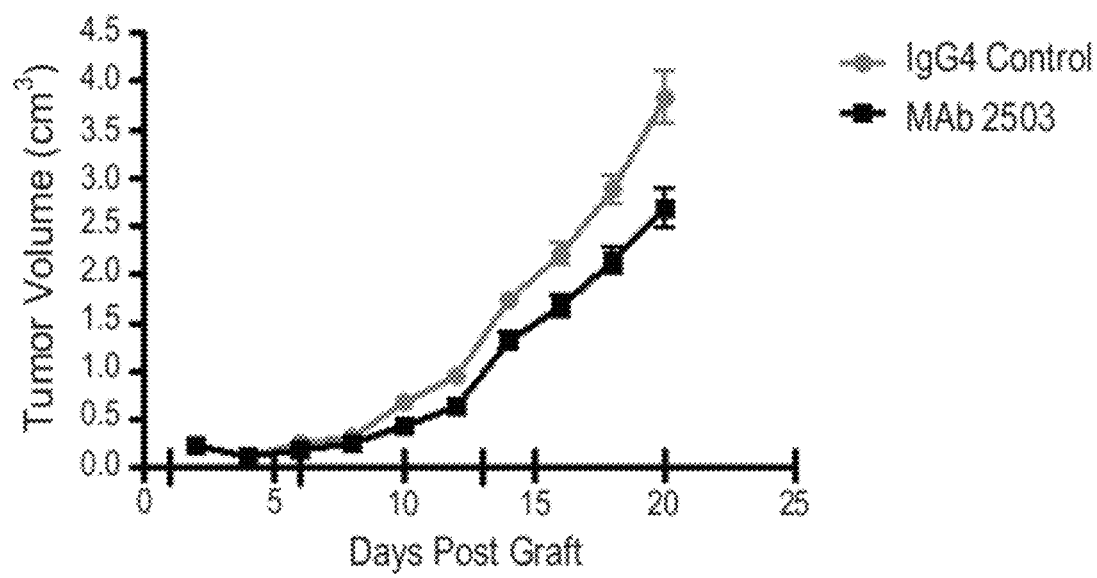
Figure 19B:
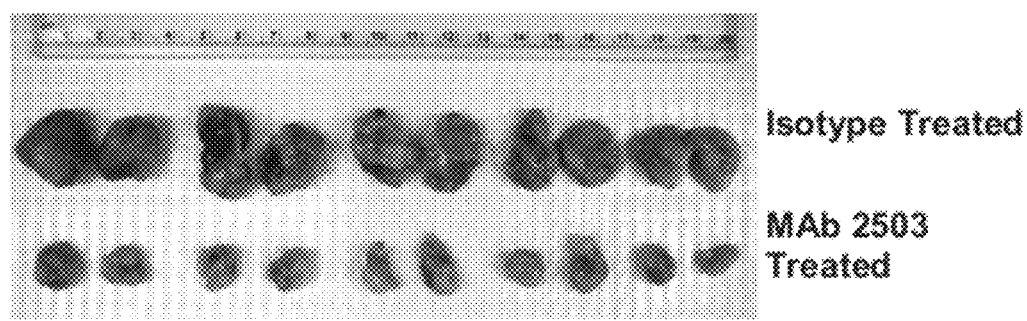

The endpoint for this experiment was TGD. Tumor growth results for MAb 2503 treatment in HN12 and HN6 HIF-1a mODD xenograft models are shown in FIGS. 18 and 19A, respectively. The TGD in HN6 HIF-1a mODD xenograft mice treated with MAb 2503 was 13% (p=0.0008). Furthermore, pictures of representative tumors from HN6 HIF-1a mODD xenograft mice treated with IgG4 control and MAb 2505 are shown in FIG. 19B. These results show that treatment with MAb 2503 reduced human head and neck tumor growth in vivo.

Example 12

Stable CHO-S Cell Line for Expressing High Titers of MAb 2503

A stable CHO-S cell line was derived for expressing high titers of MAb 2503. Complementary DNA (cDNA) for the heavy and light chains of the humanized anti-CD100 monoclonal antibody 2503 were used to produce several Chinese hamster ovary (CHO-S) expression cell lines constructed using GPEx™ technology (Catalent Pharma Solutions, Madison, Wis.) and progenitor CHO-S cells (see Bleck et al., "An Alternative Method for the Rapid Generation of Stable, High-Expressing Mammalian Cell Lines," BioProcessing Journal (September/October 2005)).

Following single cell cloning, one expression clone was selected based on growth in culture and antibody production, and a research bank of vialed expression cells was produced. The expressed antibody produced by this clone was characterized for potency and specificity using in vitro and in vivo functional assays (e.g. flow blocking and detachment assays). Subsequently, cells from the selected CHO expression clone were expanded in culture and a second (Parental Seed Stock) bank prepared and frozen. Cells from one vial from the parental seed stock bank were subsequently expanded in culture and used for cGMP production of the Master Cell Bank (MCB).

Example 13

Anti-CD100 Antibody Dosage and PK Studies in Rat and Cynomolgus Monkey

Single intravenous injection saturation analysis of MAb 2503 in rat and cymonolgus monkey was performed.

Figure 20A:
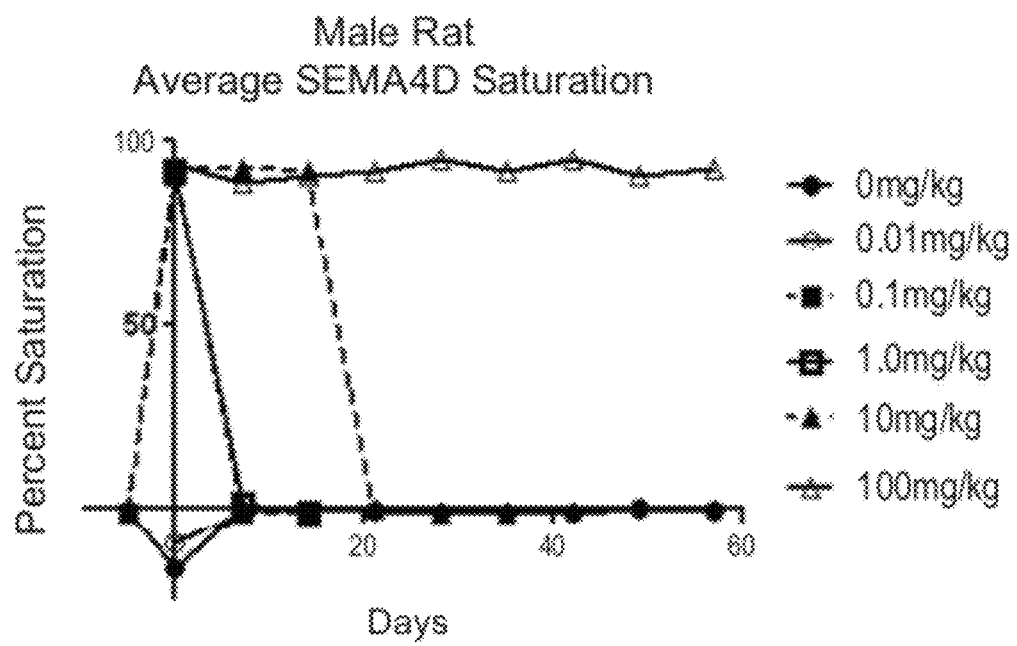
Figure 20B:
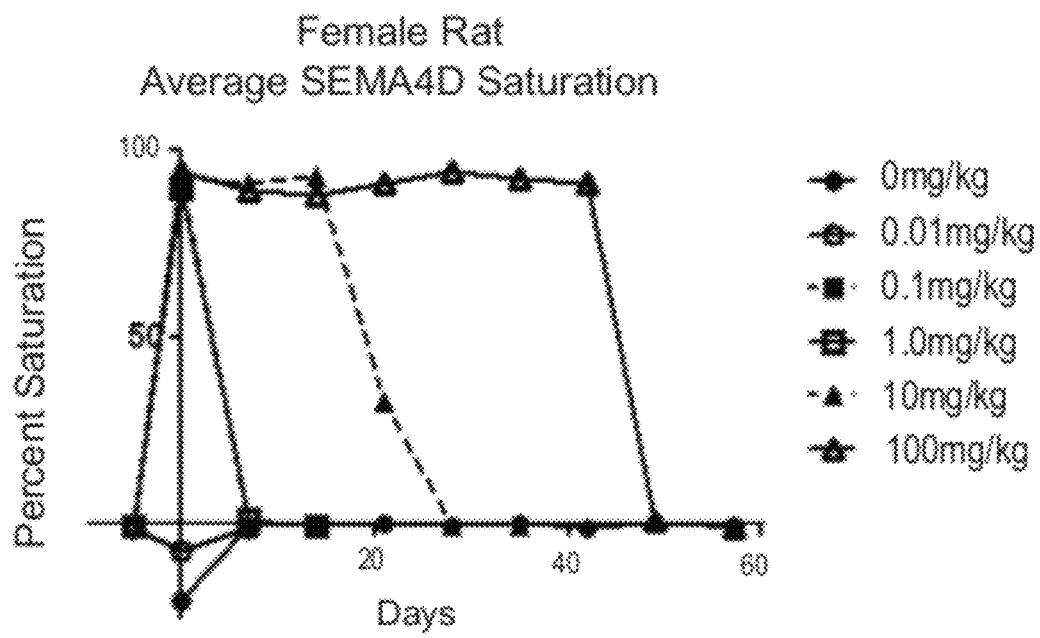

Rat Study: 36 Sprague-Dawley rats (3/sex/group) were administered a single intravenous injection of MAb 2503 ranging from 0.01 to 100 mg/kg. A flow cytometry-based saturation assay was performed on lysed whole blood at various time points to determine the percent of the cellular target (SEMA4D) that was saturated with MAb 2503. There was good data correlation with the amount of MAb detected in the serum, suggesting that saturation was dependent on the amount of free-drug in the serum, and that cells were saturated when approximately 1 to 5 ug/ml of free drug is detected in the serum. The percent saturation of SEMA4D at MAb 2503 doses of 0, 0.01, 0.1, 1.0, 10, and 100 mg/kg in male and female rats is shown in FIGS. 20A and 20B, respectively.

Primate Study: 28 cynomolgus monkeys (2/sex/group; 4/sex/control group) were administered a single intravenous injection of MAb 2503 ranging from 0.01 to 100 mg/kg. A flow cytometry-based saturation assay was performed on lysed whole blood at various time points to determine the percent of the cellular target (SEMA4D) that was saturated with MAb 2503. There was good data correlation with the amount of MAb detected in the serum, suggesting that saturation was dependent on the amount of free-drug in the serum, and that cells were saturated when approximately 1 to 5 ug/ml of free drug was detected in the serum. The percent saturation of SEMA4D at MAb 2503 doses of 0, 0.01, 0.1, 1.0, 10, and 100 mg/kg in male and female rats (combined) is shown in FIG. 21. The rat and primate saturation results were very similar.

Pharmacokinetic (PK) results including biological half-life (hours (days)), plasma antibody concentration at time zero following injection ($C_0$), and area under the plasma concentration curve from time zero to time t ($AUC_{0-t}$) for single intravenous injections of 0.01, 0.1, 1.0, 10, or 100 mg/kg MAb 2503 in rat and primate are shown in Table 9.

TABLE 9

| | PK Values for 2503 antibody in rat and primate (cynomolgus monkey) | | | | | |
|---|---|---|---|---|---|---|
| Dose | Half-life (hours (days)) | | $C_0$ (μg/mL) | | $AUC_{0-t}$ | |
| (mg/kg) | Cyno | Rat | Cyno | Rat | Cyno | Rat |
| 0.01 | | | 0.1051 | No data | 0.3573 | No data |
| Phase A | 0.1649 (0.01) | No data | | | | |
| Phase B | 43.21 (1.80) | No data | | | | |
| 0.1 | | | 3.356 | 1.99 | 23.09 | 11.40 |
| Phase A | 0.1659 (0.01) | 3.47 (0.14) | | | | |
| Phase B | 6.829 (0.28) | No data | | | | |
| 1.0 | | | 39.35 | 34.14 | 1,974 | 834.7 |
| Phase A | 3.175 (0.13) | 0.636 (0.026) | | | | |
| Phase B | 43.69 (1.82) | 27.77 (1.2) | | | | |
| 10 | | | 327.1 | 317.7 | 38,741 | 27,431 |
| Phase A | 3.075 (0.13) | 5.85 (0.24) | | | | |
| Phase B | 109.4 (4.56) | 105.7 (4.4) | | | | |
| 100 | | | 3,681 | 3,305 | 477,154 | 488,194 |
| Phase A | 6.978 (0.29) | 9.20 (0.38) | | | | |
| Phase B | 239.8 (9.99) | 246.2 (10.3) | | | | |

The MAb 2503 elimination phase half life was found to be similar between rat and cynomolgus monkey, and ranged from about 6 hours to about 10 days in a dose dependent fashion. Both the saturation and PK results appear to be dose dependent and suggest a remarkably similar profile between rat and cynomolgus monkey. Furthermore, no significant toxicity for MAb 2503 at doses ranging from 0.01 to 100 mg/kg was observed in rat or cynomolgus monkey.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. An isolated polynucleotide comprising a nucleotide sequence which encodes an antibody heavy chain variable region (VH) polypeptide comprising the amino acid sequence SEQ ID NO: 9; wherein an antibody comprising said VH polypeptide and a VL polypeptide comprising VL-CDR1, VL-CDR2, and VL-CDR3 amino acid sequences consisting of SEQ ID NOs: 14, 15, and 16, respectively, can specifically bind to CD100.

2. The polynucleotide of claim 1, wherein the nucleotide sequence encoding said VH polypeptide is optimized for increased expression without changing the amino acid sequence of said VH polypeptide.

3. The polynucleotide of claim 2, wherein said optimization comprises identification and removal of splice donor and splice acceptor sites.

4. The polynucleotide claim 2, wherein said optimization comprises optimization of codon usage for the cells expressing said polynucleotide.

5. The polynucleotide of claim 1, wherein the nucleotide sequence comprises SEQ ID NO: 19.

6. The polynucleotide of claim 5, wherein said nucleotide sequence consists of SEQ ID NO: 19.

7. An isolated polynucleotide comprising a nucleotide sequence which encodes an antibody light chain variable region (VL) polypeptide comprising the amino acid sequence SEQ ID NO: 17; wherein an antibody comprising said VL polypeptide and a VH polypeptide comprising VH-CDR1, VH-CDR2, and VH-CDR3 amino acid sequences consisting of SEQ ID NOs: 6, 7, and 8, respectively, can specifically bind to CD100.

8. The polynucleotide of claim 7, wherein the nucleotide sequence encoding said VL polypeptide is optimized for increased expression without changing the amino acid sequence of said VL polypeptide.

9. The polynucleotide of claim 8, wherein said optimization comprises identification and removal of splice donor and splice acceptor sites.

10. The polynucleotide of claim 8, wherein said optimization comprises optimization of codon usage for the cells expressing said polynucleotide.

11. The polynucleotide of claim 7, wherein the nucleotide sequence comprises SEQ ID NO: 21.

12. The polynucleotide of any claim 11, wherein said nucleotide sequence consists of SEQ ID NO: 21.

13. A composition comprising an isolated VH encoding polynucleotide and an isolated VL encoding polynucleotide, wherein said VH encoding polynucleotide comprises a cDNA that encodes a VH polypeptide comprising VH-CDR1, VH-CDR2, and VH-CDR3 amino acid sequences consisting of SEQ ID NOs: 6, 7, and 8, respectively; wherein said VL encoding polynucleotide comprises a cDNA that encodes a VL polypeptide comprising VL-CDR1, VL-CDR2, and VL-CDR3 amino acid sequences consisting of SEQ ID NOs: 14, 15, and 16, respectively; and wherein an antibody or fragment thereof encoded by said VH and VL encoding polynucleotides specifically binds CD100.

14. The composition of claim 13 wherein said VH encoding polynucleotide and said VL encoding polynucleotide are contained on a single vector or on separate vectors.

15. A host cell comprising the composition of claim 14.

16. A method of producing an antibody or fragment thereof which specifically binds CD100, comprising culturing the host cell of claim 15 and recovering said antibody or fragment thereof.

17. A vector comprising the polynucleotide of claim 1.

18. A host cell comprising the vector of claim 17.

19. A vector comprising the polynucleotide of claim 7.

20. A host cell comprising the vector of claim 19.

21. A recombinant host cell comprising a VH-encoding polynucleotide and a VL-encoding polynucleotide, wherein the VH-encoding polynucleotide encodes a VH polypeptide comprising VH-CDR1, VH-CDR2, and VH-CDR3 amino acid sequences consisting of SEQ ID NOs: 6, 7, and 8, respectively, wherein the VL-encoding polynucleotide encodes a VL polypeptide comprising VL-CDR1, VL-CDR2, and VL-CDR3 amino acid sequences consisting of SEQ ID NOs: 14, 15, and 16, respectively, wherein the VH encoding polynucleotide and the VL encoding polynucleotide are situated on separate vectors, and wherein an antibody or fragment thereof encoded by the VH and VL encoding polynucleotides specifically binds CD100.

22. The host cell of claim 21, wherein the VH polypeptide comprises the amino acid sequence SEQ ID NO:9 and the VL polypeptide comprises the amino acid sequence SEQ ID NO:17.

23. The host cell of claim 22, which produced from the CHO cell line.

24. A method of producing an antibody or fragment thereof which specifically binds CD100, comprising culturing the host cell of claim 22 and recovering the antibody or fragment thereof.

* * * * *